United States Patent
Bornarth et al.

(10) Patent No.: US 10,767,217 B2
(45) Date of Patent: Sep. 8, 2020

(54) COMPOSITIONS, METHODS AND KITS FOR REAL TIME POLYMERASE CHAIN REACTION (PCR)

(71) Applicant: LIFE TECHNOLOGIES CORPORATION, Carlsbad, CA (US)

(72) Inventors: Carole Bornarth, Fremont, CA (US); Michael Lau, Sunnyvale, CA (US); Junko Stevens, Menlo Park, CA (US)

(73) Assignee: Life Technologies Corporation, Carlsbad, CA (US)

( * ) Notice: Subject to any disclaimer, the term of this patent is extended or adjusted under 35 U.S.C. 154(b) by 142 days.

(21) Appl. No.: 15/927,572

(22) Filed: Mar. 21, 2018

(65) Prior Publication Data

US 2018/0282797 A1 Oct. 4, 2018

Related U.S. Application Data

(62) Division of application No. 13/918,768, filed on Jun. 14, 2013, now Pat. No. 9,951,378.

(60) Provisional application No. 61/659,587, filed on Jun. 14, 2012.

(51) Int. Cl.
  *C12Q 1/68* (2018.01)
  *C07K 16/00* (2006.01)
  *C12N 9/00* (2006.01)
  *C12Q 1/6848* (2018.01)
  *C12Q 1/686* (2018.01)

(52) U.S. Cl.
  CPC ............ *C12Q 1/6848* (2013.01); *C07K 16/00* (2013.01); *C12N 9/00* (2013.01); *C12Q 1/686* (2013.01)

(58) Field of Classification Search
  CPC ............ C12Q 1/6848; C12Q 2527/101; C12Q 2527/127; C12Q 2549/101
  See application file for complete search history.

(56) References Cited

U.S. PATENT DOCUMENTS

| | | | |
|---|---|---|---|
| 8,129,150 B2 | 3/2012 | Holger et al. | |
| 9,951,378 B2 | 4/2018 | Bornarth et al. | |
| 2006/0172312 A1 | 8/2006 | Bishop et al. | |
| 2009/0117622 A1 | 5/2009 | Engel et al. | |
| 2015/0044683 A1 | 2/2015 | Park et al. | |

FOREIGN PATENT DOCUMENTS

| | | |
|---|---|---|
| EP | 1920064 B1 | 12/2014 |
| JP | 2003535587 A | 12/2003 |
| JP | 2006-522582 | 10/2006 |
| JP | 4053363 B2 | 2/2008 |
| JP | 2009-532046 | 9/2009 |
| JP | 6450308 B2 | 1/2019 |

OTHER PUBLICATIONS

Applied Biosystems: "Fast Real-Time PCR", Dec. 21, 2011 (Dec. 21, 2011), XP055505245, Retrieved from the Internet: URL: http://www3.appliedbiosystems.com/cms/groups/mcb_marketing/documents/generaldocuments/cms_100372.pdf, [retrieved on Sep. 6, 2018].
Lebedev AV., et al., "Hot Start PCR with Heat-activatable Primers: A Novel Approach for Improved PCR Performance", Nucleic Acids Research, 2008, vol. 36, No. 20, e131, pp. 1-18.
Anonymous, "FQ dual core era has arrived", Beiing Sincelion Technology Co. Ltd., XP002707397, Retrieved from the Internet: URL:http://www.xllkj.com/News-Details.aspx?id=10 [retrieved on Jul. 30, 2013] Abstract, Nov. 2, 2011; 1 page.
Foster, et al. "Unbiased Quantitative Proteomics of Lipid Rafts Reveals High Specificity for Signaling Factors," *Proceedings of the National Academy of Sciences (PNAS)*, vol. 100, No. 10, May 13, 2003; pp. 5813-5818.
Maki, T et al., "PCR Tips—Hot Start PCR", *Cell Engineering Supplement: Tips Series Revised Chapter 1 Basics*, Nara Institute of Science and Technology Graduate School Bioscience Graduate Course, Dec. 10, 1999, 65-66.
Mizuguchi, H et al., "Characterization and Application to Hot Start PCR of Neutralizing Monoclonal Antibodies against KOD DNA Polymerase", *J. Biochem.*, vol. 126, 1999, 762-768.
Paul, N et al., "Hot Start PCR", *Methods in Molecular Biology (Clifton, N.J.)*, vol. 630, Jan. 1, 2010, 301-318.
PCT/US2013/046010, International Preliminary Report on Patentability dated Dec. 24, 2014, 6 Pages.
PCT/US2013/046010, International Search Report and Written Opinion dated Aug. 23, 2013, 11 pages.
Toyobo Co. Ltd., "High Fidelity PCR Enzyme", *KOD Plus Instruction Manual*, Feb. 2008, 5 pages.
EP19198094.5, Extended Search Report, Mar. 30, 2020, 11 pages.

*Primary Examiner* — David C Thomas

(57) ABSTRACT

The present disclosure is directed to compositions, methods and kits for amplifying target nucleic acids while reducing non-specific amplification and undesired amplification products using a dual hot start reaction mixture that comprise at least two different hot start mechanisms.

14 Claims, 57 Drawing Sheets

Comparison of mean Ct and ΔCt for Fast SYBR® & Platinum® SYBR®

A2M

| A2M | T0 | | T24 | | ΔCt (24H - 0H) | |
|---|---|---|---|---|---|---|
| | cDNA Mean | NTC Mean | cDNA Mean | NTC Mean | cDNA | NTC |
| Fast SYBR | 24.84 | 36.66 | 25.22 | 33.51 | 0.38 | -3.15 |
| Fast SYBR & Platinum SYBR | 25.77 | 39.16 | 25.72 | 39.95 | -0.05 | 0.78 |
| Platinum SYBR | 25.51 | 38.05 | 25.75 | 37.34 | 0.24 | -0.71 |

COL1A1

| COL1A1 | T0 | | T24 | | ΔCt (24H - 0H) | |
|---|---|---|---|---|---|---|
| | cDNA Mean | NTC Mean | cDNA Mean | NTC Mean | cDNA | NTC |
| Fast SYBR | 24.07 | 35.17 | 24.50 | 27.29 | 0.43 | -7.89 |
| Fast SYBR & Platinum SYBR | 24.52 | 40.00 | 24.59 | 40.00 | 0.07 | 0.00 |
| Platinum SYBR | 24.57 | 40.00 | 24.54 | 38.93 | -0.03 | -1.07 |

IL1R1

| IL1R1 | T0 | | T24 | | ΔCt (24H - 0H) | |
|---|---|---|---|---|---|---|
| | cDNA Mean | NTC Mean | cDNA Mean | NTC Mean | cDNA | NTC |
| Fast SYBR | 28.33 | 34.49 | 29.21 | 33.33 | 0.88 | -1.16 |
| Fast SYBR & Platinum SYBR | 29.09 | 40.00 | 29.00 | 39.28 | -0.09 | -0.72 |
| Platinum SYBR | 29.03 | 39.86 | 29.08 | 40.00 | 0.05 | 0.14 |

Fig. 2M

Melt Curve Analysis of Fast SYBR® and Platinum® SYBR®

| Master Mix | Fast SYBR | | Fast SYBR & Platinum SYBR | | Platinum SYBR | |
|---|---|---|---|---|---|---|
| Time | T0 | T24 | T0 | T24 | T0 | T24 |
| A2M | 4 | 4 | 1 | 0 | 1 | 3 |
| ABCC2 | 4 | 4 | 4 | 4 | 2 | 2 |
| ADAM10 | 3 | 1 | 2 | 1 | 0 | 0 |
| AOF1 | 0 | 4 | 0 | 1 | 1 | 0 |
| APOA1 | 4 | 4 | 1 | 1 | 1 | 0 |
| ARL1 | 4 | 4 | 1 | 3 | 0 | 0 |
| C11orf30 | 4 | 4 | 4 | 4 | 3 | 4 |
| CCNB1 | 4 | 4 | 1 | 1 | 1 | 1 |
| COL1A1 | 4 | 4 | 0 | 0 | 0 | 1 |
| CTGF | 4 | 4 | 2 | 4 | 1 | 0 |
| METTL3 | 4 | 3 | 0 | 0 | 0 | 0 |
| IL1R1 | 4 | 4 | 0 | 1 | 0 | 0 |
| MTIF2 | 4 | 4 | 4 | 4 | 4 | 0 |
| PDGFB | 4 | 4 | 1 | 3 | 0 | 1 |
| PRDX4 | 0 | 1 | 0 | 0 | 0 | 1 |
| SERPINE1 | 1 | 0 | 0 | 0 | 0 | 0 |
| SMAD4 | 2 | 4 | 2 | 0 | 0 | 0 |
| TCF25 | 0 | 0 | 0 | 0 | 0 | 0 |
| TCF3 | 1 | 0 | 1 | 0 | 0 | 0 |
| TCF4 | 4 | 4 | 4 | 3 | 0 | 2 |
| TIMP3 | 4 | 4 | 2 | 2 | 0 | 1 |
| VEGFC | 0 | 0 | 4 | 1 | 4 | 3 |
| GUSB | 2 | 0 | 0 | 0 | 1 | 0 |
| PGK1 | 0 | 0 | 0 | 1 | 0 | 0 |
| Total | 65 | 65 | 34 | 34 | 19 | 19 |

*Anomaly defined as any melt curve peak over 0.2 ΔRn

| | Fast SYBR | | Fast SYBR & Platinum SYBR | | Platinum SYBR | |
|---|---|---|---|---|---|---|
| | T0 | T24 | T0 | T24 | T0 | T24 |
| Number of non-40 NTCs | 68 | 66 | 39 | 39 | 23 | 18 |
| 0.2 Threshold | 68 | 66 | 42 | 42 | 25 | 26 |
| Auto-Threshold Threshold Value | 0.16736 | 0.18702 | 0.12552 | 0.10238 | 0.10509 | 0.08440 |
| | 9 | 7 | 2 | 9 | 1 | 7 |

Fig. 2N

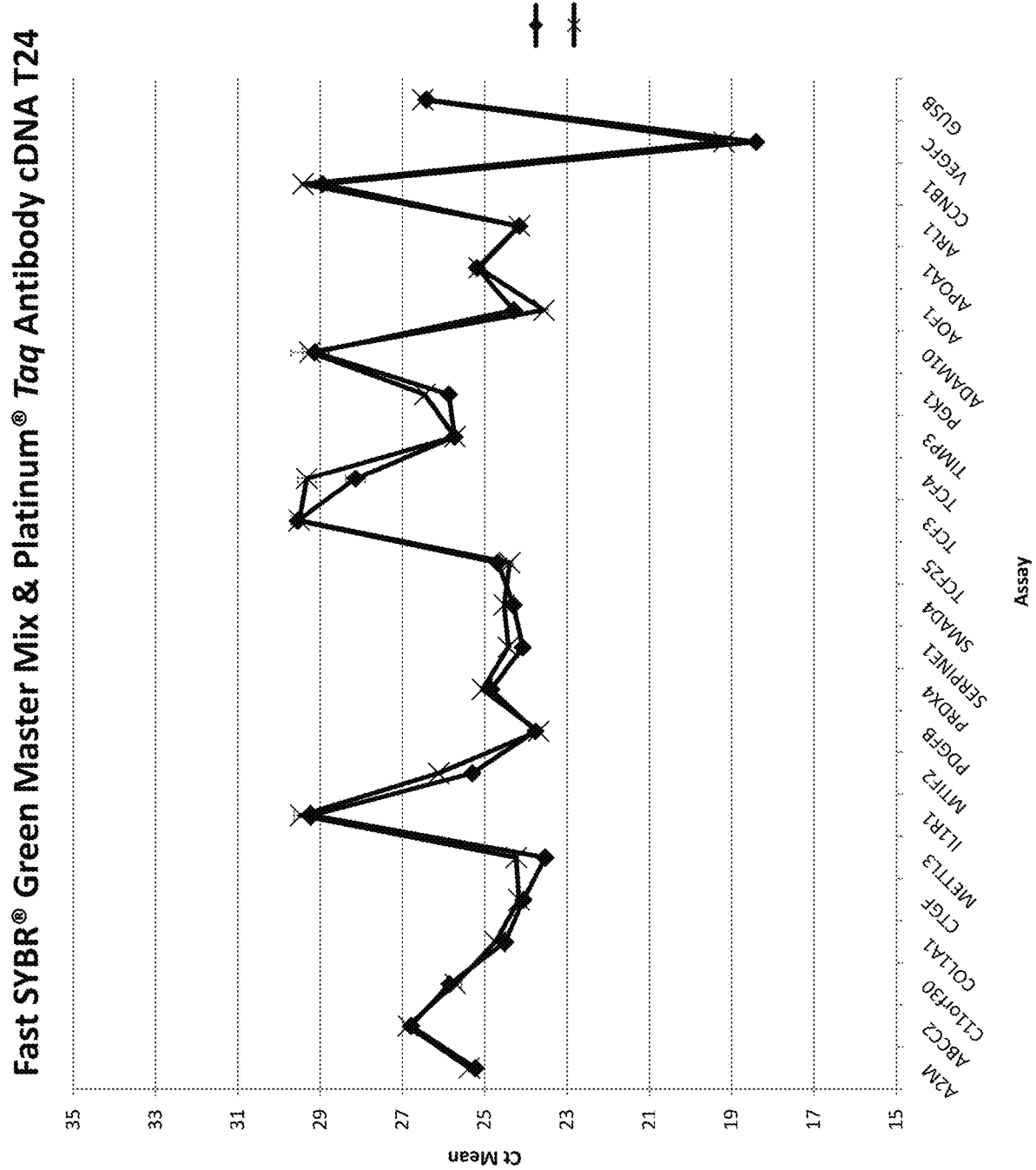

A2M Assay FastSYBR® Green Master Mix & Platinum®
*Taq* Antiboby Melt Curve Analysis

|  | T0 | | T24 | |
|---|---|---|---|---|
| A2M | CDNA Mean | NTC Mean | CDNA Mean | NTC Mean |
| Fast SYBR | 24.84 | 36.66 | 25.22 | 33.51 |
| Fast SYBR & Platinum Antibody | 25.25 | 39.69 | 25.37 | 40.00 |
| ΔCt | -0.41 | -0.42 | -0.15 | -6.49 |

FIG. 4E

Fast SYBR® Green Master Mix & Platinum® Taq Antibody
Melt Curve Analysis

| Master Mix | Fast SYBR | | Fast SYBR & Platinum Ab | |
|---|---|---|---|---|
| Time | T0 | T24 | T0 | T24 |
| A2M | 4 | 4 | 1 | 0 |
| ABCC2 | 4 | 4 | 4 | 4 |
| ADAM10 | 3 | 1 | 1 | 0 |
| AOF1 | 0 | 4 | 0 | 0 |
| APOA1 | 4 | 4 | 1 | 1 |
| ARL1 | 4 | 4 | 4 | 2 |
| C11orf30 | 4 | 4 | 4 | 4 |
| CCNB1 | 4 | 4 | 4 | 4 |
| CQ1A1 | 4 | 4 | 4 | 4 |
| CTGF | 4 | 4 | 4 | 4 |
| METTL3 | 4 | 3 | 0 | 0 |
| IL1R1 | 4 | 4 | 4 | 3 |
| MT1F2 | 4 | 4 | 4 | 4 |
| PDGFB | 4 | 4 | 4 | 3 |
| PRDX4 | 0 | 1 | 0 | 0 |
| SERPINE1 | 1 | 0 | 0 | 0 |
| SMAD4 | 2 | 4 | 0 | 1 |
| TCF25 | 0 | 0 | 0 | 0 |
| TCF3 | 1 | 0 | 0 | 1 |
| TCF4 | 4 | 4 | 4 | 4 |
| TIMP3 | 4 | 4 | 4 | 3 |
| VEGFC | 0 | 0 | 2 | 1 |
| GUSB | 2 | 0 | 0 | 0 |
| PGK1 | 0 | 0 | 0 | 1 |
| Total | 65 | 65 | 49 | 44 |

*Anomaly defined as any melt curve peak over 0.2 ΔRn

| | Fast SYBR | | | | Fast SYBR & Platinum | | | |
|---|---|---|---|---|---|---|---|---|
| | T0 | | T24 | | T0 | | T24 | |
| A2M | cDNA Mean | NTC Mean | cDNA Mean | NTC Mean | | | | |
| Fast SYBR | 24.84 | 36.66 | 25.22 | 33.51 | | | | |
| Fast SYBR & Platinum Antibody | | | | | 25.25 | 39.69 | 25.37 | 40.00 |
| SMAD4 | cDNA Mean | NTC Mean | cDNA Mean | NTC Mean | | | | |
| Fast SYBR | 23.90 | 39.48 | 24.30 | 32.91 | | | | |
| Fast SYBR & Platinum Antibody | | | | | 24.62 | 40.00 | 24.53 | 39.66 |
| METTL3 | cDNA Mean | NTC Mean | cDNA Mean | NTC Mean | | | | |
| Fast SYBR | 23.37 | 36.40 | 23.53 | 37.21 | | | | |
| Fast SYBR & Platinum Antibody | | | | | 24.21 | 40.00 | 24.23 | 40.00 |
| APOA1 | cDNA Mean | NTC Mean | cDNA Mean | NTC Mean | | | | |
| Fast SYBR | 24.70 | 36.54 | 25.18 | 30.08 | | | | |
| Fast SYBR & Platinum Antibody | | | | | 24.62 | 39.32 | 25.14 | 39.29 |

| | Fast SYBR | | Fast SYBR & Platinum Ab | |
|---|---|---|---|---|
| | T0 | T24 | T0 | T24 |
| Number of non-40 NTCs | 68 | 66 | 50 | 48 |
| 0.2 Threshold | 68 | 66 | 54 | 53 |
| Auto-Threshold | 0.167369 | 0.187027 | 0.106496 | 0.108216 |
| Threshold | | | | |

Fig. 4F

Gumby 1 Assay: Power SYBR® Green PCR Master Mix & Platinum® Taq Antibody: Melt Curve Analysis

| Master Mix | Power SYBR | | Power SYBR & Platinum Ab | |
|---|---|---|---|---|
| Time | T0 | T24 | T0 | T24 |
| A2M | 2 | 4 | 0 | 2 |
| ABCC2 | 4 | 4 | 2 | 4 |
| ADAM10 | 0 | 3 | 1 | 4 |
| AOF1 | 2 | 4 | 0 | 3 |
| APOA1 | 3 | 4 | 1 | 4 |
| ARL1 | 1 | 4 | 0 | 4 |
| C11orf30 | 4 | 4 | 0 | 4 |
| CCNB1 | 2 | 2 | 0 | 0 |
| COL1A1 | 3 | 4 | 0 | 2 |
| CTGF | 2 | 4 | 3 | 4 |
| METTL3 | 0 | 4 | 0 | 1 |
| IL1R1 | 1 | 4 | 0 | 2 |
| MTHF2 | 4 | 4 | 0 | 4 |
| PDGFB | 1 | 4 | 0 | 4 |
| PRDX4 | 0 | 0 | 0 | 3 |
| SERPINE1 | 0 | 0 | 1 | 0 |
| SMAD4 | 0 | 3 | 0 | 4 |
| TCF25 | 0 | 0 | 0 | 1 |
| TCF3 | 0 | 0 | 1 | 1 |
| TCF4 | 2 | 4 | 0 | 4 |
| TIMP3 | 3 | 2 | 1 | 3 |
| VEGFC | 0 | 1 | 0 | 0 |
| GUSB | 0 | 0 | 0 | 0 |
| PGK1 | 2 | 2 | 2 | 2 |
| Total | 36 | 65 | 12 | 60 |

*Anomaly defined as any melt curve peak over 0.2 ΔRn

| A2M | T0 | | T24 | |
|---|---|---|---|---|
|  | cDNA Mean | NTC Mean | cDNA Mean | NTC Mean |
| Power SYBR | 24.28 | 39.21 | 24.30 | 34.36 |
| Power SYBR & Platinum Antibody | 24.57 | 40.00 | 24.58 | 38.07 |

| METTL3 | T0 | | T24 | |
|---|---|---|---|---|
|  | cDNA Mean | NTC Mean | cDNA Mean | NTC Mean |
| Power SYBR | 23.05 | 40.00 | 23.11 | 31.79 |
| Power SYBR & Platinum Antibody | 24.04 | 40.00 | 24.07 | 38.83 |

| Number of non-40 NTCs | Power SYBR | | Power SYBR & Platinum Ab | |
|---|---|---|---|---|
|  | T0 | T24 | T0 | T24 |
| 0.2 Threshold | 34 | 64 | 10 | 56 |
| Auto-Threshold | 34 | 64 | 12 | 58 |
| Threshold | 0.207303 | 0.202486 | 0.122834 | 0.112996 |

Fig. 6E

COMPOSITIONS, METHODS AND KITS FOR REAL TIME POLYMERASE CHAIN REACTION (PCR)

CROSS-REFERENCE TO RELATED APPLICATIONS

This application is a divisional of U.S. application Ser. No. 13/918,768, filed Jun. 14, 2013, which claims a priority benefit under 35 U.S.C. § 119(e) to U.S. Provisional Patent Application No. 61/659,587, filed Jun. 14, 2012. The entire contents of the aforementioned applications are incorporated by reference in their entireties herein.

FIELD

This disclosure generally relates to compositions, methods and kits for amplifying nucleic acids while reducing non-specific amplification and/or undesired amplification products.

BACKGROUND

While the polymerase chain reaction (PCR) and related techniques are highly useful for a variety of applications, the amplification of non-target nucleic acids due to undesired side-reactions can present a significant problem. Such side reactions can occur as a result of mis-priming of non-target nucleic acids and/or primer oligomerization, sometimes referred to as primer-dimer formation, and the subsequent amplification of these priming artifacts. This is especially true in applications in which PCR is carried out using a mixture of nucleic acids with significant background nucleic acids while the target nucleic acid is present in low copy number (see, e.g., Chou et al., Nucl. Acids Res. 20:1717 (1992)). The generation of non-specifically amplified products has been attributed at least in part to DNA polymerase activity at ambient temperature that extends non-specifically annealed primers (see, e.g., Chou et al., supra; Li et al., Proc. Natl. Acad. Sci. USA 87:4580 (1990)). Accordingly, inhibition of DNA polymerase activity at ambient temperature is beneficial in controlling the generation of secondary amplicons.

Several "hot start" techniques have been described which reportedly decrease the formation of undesired secondary amplification products. According to certain "manual hot start" techniques, a component critical to DNA polymerase activity (e.g., divalent ions and/or the DNA polymerase itself) is not added to the reaction mixture until the temperature of the mixture is high enough to prevent non-specific primer annealing (see, e.g., Chou et al., supra; D'Aquila et al., Nucl. Acids Res. 19:3749 (1991)). Less labor-intensive techniques employ the physical separation or reversible inactivation of at least one component of the amplification reaction. For example, the magnesium or the DNA polymerase can be sequestered in a wax bead, which melts as the reaction temperature increases, releasing the sequestered component only at the elevated temperature. According to other techniques, the DNA polymerase is reversibly inactivated or modified, for example by a reversible chemical modification of the DNA polymerase, the binding of an antibody to the DNA polymerase, or oligonucleotide molecules that bind to the DNA polymerase (see, e.g., U.S. Pat. Nos. 5,677,152 and 5,338,671; and Dang et al., J. Mol. Biol. 264:268 (1996)). At an elevated reaction temperature, the chemical modification is reversed, or the antibody molecule or oligonucleotide molecule is denatured, releasing a functional DNA polymerase. However, some of these techniques appear to be less than optimal, in that some DNA polymerase activity is detectable at lower reaction temperatures despite the inactivation, or they require extended exposure of the reaction mixture at high temperatures to fully activate the DNA polymerase, which may result in permanent inactivation of some components of the reaction mixture.

Certain currently used nucleic acid amplification techniques include a step for detecting and/or quantifying amplification products that comprise a nucleic acid dye, for example, but not limited to, SYBR® Green I (Life Technologies, Carlsbad, Calif.), including certain real-time and/or end-point detection techniques (see, e.g., Ririe et al., Anal. Biochem. 245:154 (1997)). Typically the nucleic acid dye associates with double-stranded segments of the amplification products and/or primer-template duplexes and emits a detectable fluorescent signal at a wavelength that is characteristic of the particular nucleic acid dye. Certain amplification methods comprise a detection step for evaluating the purity of the amplification product(s) associated with the nucleic acid dye, for example but not limited to, post-PCR dissociation curve analysis, also known as melting curve analysis. Since the melting curve of an amplicon is dependent on its length and sequence (among other things), amplicons can generally be distinguished by their melting curves (see, e.g., Zhang et al., Hepatology 36:723 (2002)). A dissociation or melting curve can be obtained during certain amplification reactions by monitoring the nucleic acid dye fluorescence as the reaction temperatures pass through the melting temperature of the amplicon(s). The dissociation of a double-stranded amplicon is observed as a sudden decrease in fluorescence at the emission wavelength characteristic of the nucleic acid dye. According to certain dissociation curve analysis techniques, an amplification product is classified as "pure" when the melting curve shows a single, consistent melting temperature, sometimes graphically displayed as a peak on a plot of the negative derivative of fluorescent intensity versus temperature ($-dF/dt$ vs. T). In contrast, the appearance of multiple peaks in such a dissociation curve from a single-plex amplification typically indicates the presence of undesired side reaction products. When such nucleic acid dye-based amplification product detection techniques are employed, it is often desirable to: 1) at least decrease and preferably eliminate the formation of undesired side-reaction products, and 2) at least decrease and preferably eliminate fluorescence peaks resulting from the denaturing of double-stranded segments of other nucleic acids, i.e., non-amplification products (e.g., primer dimers) and/or non-specific amplification products (e.g., due to mis-priming events).

Certain other amplification techniques may also yield undesired amplification products due to, among other things, non-specific annealing of primers, ligation probes, cleavage probes, promoter-primers, and so forth, and subsequent enzyme activity at sub-optimal temperatures. For example, while reaction components are being combined, often at room temperature, or while the reaction composition is being heated to a desired reaction temperature. At least some of these techniques can benefit from a reduction in background fluorescence. Thus, there is a need for compositions and methods that decrease and/or eliminate 1) the formation of undesired side-reaction products and 2) the background fluorescence resulting from these undesired side-reaction products.

SUMMARY

The present teachings are directed to compositions, methods and kits for amplifying target nucleic acids while reducing non-specific amplification (e.g., fluorescence) and undesired amplification products, sometimes referred to in the art as secondary amplicons or spurious side-products.

In certain embodiments, compositions are provided that comprise a nucleic acid polymerase and a dual hot start reaction mixture that inhibits or substantially inhibits the polymerase activity of the nucleic acid polymerase at a first temperature (e.g., <40° C. temperature). The dual hot start reaction mixture comprises at least two different hot start mechanisms that are used to inhibit or substantially inhibit the polymerase activity of a nucleic acid polymerase at a first temperature. Such hot start mechanisms include, but are not limited to, antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers or modified dNTPs.

In certain embodiments, the dual hot start reaction mixture inhibits non-specific nucleic acid amplification and/or non-specific product formation for extended periods of time compared to conventional hot start mechanisms. For example, in some embodiments, the present dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, compositions are provided that comprise a thermostable nucleic acid polymerase and a dual hot start reaction mixture that inhibits or substantially inhibits the polymerase activity of the nucleic acid polymerase at a temperature less than about 40° C. and such that the dual hot start reaction mixture does not substantially inhibit the polymerase activity of the nucleic acid polymerase at a temperature greater than about 40° C. In certain embodiments, the nucleic acid polymerase may be a DNA-dependent DNA polymerase or an RNA-dependent DNA polymerase. In certain embodiments, the nucleic acid polymerase may be thermostable.

In certain embodiments, methods for inhibiting the polymerase activity of a nucleic acid polymerase are provided. In certain embodiments, these methods involve contacting the polymerase with a dual hot start reaction mixture, where the dual hot start reaction mixture inhibits or substantially inhibits the polymerase activity of the nucleic acid polymerase at a first temperature (e.g., <40° C. temperature). Polymerase inhibition may be reversible (e.g., by heating to a temperature greater than said first temperature, typically to a temperature of at least about 40° C.). The dual hot start reaction mixture comprises at least two different hot start mechanisms that are used to inhibit or substantially inhibit the polymerase activity of a nucleic acid polymerase at a first temperature (e.g., ambient temperature). Such hot start mechanisms include, but are not limited to, antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers, or modified dNTPs. In certain embodiments, the nucleic acid polymerase may be a DNA-dependent DNA polymerase or an RNA-dependent DNA polymerase. In certain embodiments, the nucleic acid polymerase may be thermostable.

In certain embodiments, methods for synthesizing a nucleic acid molecule are provided. Such methods involve contacting a template nucleic acid with a composition comprising a thermostable nucleic acid polymerase, a dual hot start reaction mixture, one or more nucleoside and/or deoxynucleoside triphosphates and at least one primer, wherein the dual hot start reaction mixture inhibits or substantially inhibits polymerase activity of the nucleic acid polymerase (compared polymerase activity in reaction mixtures without a dual hot start mechanism) at a lower temperature (e.g., ambient temperature), bringing the resulting mixture to a higher temperature sufficient to relieve polymerase inhibition, and polymerizing the template nucleic acid.

In certain embodiments, methods for reducing non-specific fluorescence using the dual hot start reaction mixture are provided. According to such methods, a nucleic acid polymerase is contacted with the dual hot start reaction mixture at a first temperature under conditions suitable for the dual hot start reaction mixture to substantially inhibit polymerase activity of the nucleic acid polymerase. When the resulting mixture is heated to a suitable second temperature, the dual hot start reaction mixture halts inhibition of the nucleic acid polymerase or nucleic acid polymerase activity.

In certain embodiments, the dual hot start reaction mixture inhibits non-specific nucleic acid amplification and/or non-specific product formation for extended periods of time compared to conventional hot start mechanisms. For example, in some embodiments, the present dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, methods for reducing non-specific fluorescence using a dual hot start reaction mixture are provided. According to such methods, a reaction composition is formed at a first temperature comprising a nucleic acid polymerase, a dual hot start reaction mixture, at least one NTP or dNTP, a target nucleic acid, at least one primer and at least one nucleic acid binding dye. In certain embodiments, the at least one primer comprises a primer pair. At the first temperature (e.g., <40° C. temperature, such as ambient or room temperature), the dual hot start reaction mixture inhibits or substantially inhibits polymerase activity of the nucleic acid polymerase. The reaction composition is subsequently heated to a second reaction temperature that causes the dual hot start reaction mixture to restore activity to the nucleic acid polymerase. The reaction composition is subjected to at least one cycle of amplification and at least one amplicon is generated. The double-stranded amplicons may be detected, either in "real time" or after the amplification reaction is completed due to the fluorescence of the nucleic acid binding dye associated with the amplicons.

In certain embodiments, the dual hot start reaction mixture inhibits non-specific nucleic acid amplification and/or non-specific product formation for extended periods of time compared to conventional hot start mechanisms. For example, in some embodiments, the present dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, methods for amplifying a target nucleic acid using the dual hot start reaction mixture are provided. According to certain such methods, a reaction composition is formed at a first temperature comprising a nucleic acid polymerase, a dual host start reaction mixture, at least one NTP or dNTP, a target nucleic acid, at least one primer and at least one nucleic acid binding dye. In certain embodiments, the at least one primer comprises a primer pair. At the first temperature, the dual hot start reaction mixture inhibits or substantially inhibits polymerase activity of the nucleic acid polymerase. The reaction composition is subsequently heated to a second reaction temperature that causes the dual hot start reaction mixture to halt inhibition of the nucleic acid polymerase or nucleic acid polymerase activity. The reaction composition is subjected to at least one cycle of amplification and a multiplicity of amplicons is generated. The double-stranded amplicons may be detected, either in "real time" or after the amplification reaction is completed due to the fluorescence of the nucleic acid binding dye associated with the amplicons.

In certain embodiments, kits for performing certain of the instant methods are also provided. In certain embodiments, the kits comprise a dual hot start reaction mixture. In certain embodiments, the kits further comprise at least one nucleic acid polymerase. In certain embodiments, the kits further comprise one or more of: at least one primer or a primer pair, a nucleic acid binding dye, a reporter probe, and a reverse transcriptase.

These and other features of the present teachings are provided herein.

BRIEF DESCRIPTION OF THE DRAWINGS

FIG. 1A: Amplification of cDNA at 0 h room temperature pre-incubation ("T0"); FIG. 1B: Amplification of NTC (non-specific products) at T0; C: Amplification of cDNA at 24 h room temperature pre-incubation ("T24"); and D: Amplification of NTC at T24.

FIGS. 2A-1 through 2N: Nucleic acid amplification using Fast SYBR® Green Master Mix and Platinum® SYBR® Green qPCR Master Mix, alone or in combination. FIG. 2A-1 through 2C-2: Melt curve analysis of A2M cDNA and NTC at T0; FIG. 2D-1 through 2F-2: Melt curve analysis of A2M cDNA and NTC at T24; FIG. 2G-1 through 2I-2: Melt curve analysis of COL1A1 cDNA and NTC at T0; FIG. 2J-1 through 2L-2: Melt curve analysis of COL1A1 cDNA and NTC at T24; FIG. 2M: Comparison of mean Ct and ΔCt for Fast SYBR® Green Master Mix and Platinum® SYBR® Green qPCR Master Mix, alone or in combination; FIG. 2N: Melt curve analysis of Fast SYBR® Green Master Mix and Platinum® SYBR® Green qPCR Master Mix, alone or in combination.

FIGS. 3A through 3D: Comparison of Fast SYBR® Green Master Mix alone ("diamond" line) and combination of Fast SYBR® Green Master Mix and Platinum® Taq Antibody ("cross" line). FIG. 3A: Amplification of cDNA at T0; FIG. 3B: Amplification of NTC at T0; FIG. 3C: Amplification of cDNA at T24; and FIG. 3D: Amplification of NTC at T24.

FIGS. 4A-1 through 3F: Nucleic acid amplification using Fast SYBR® Green Master Mix and Platinum® Taq Antibody, alone or in combination. FIG. 4A-1 through 4B-2: Melt curve analysis of A2M using Fast SYBR® Green Master Mix alone at T0 and T24; FIG. 4C-1 through 4E: Melt curve analysis of A2M using a combination of Fast SYBR® Green Master Mix and Platinum® Taq Antibody at T0 and T24; FIG. 4F: Melt curve analysis of Fast SYBR® Green Master Mix and Platinum® Taq Antibody, alone or in combination.

FIG. 5A: Amplification of cDNA at T0; FIG. 5B: Amplification of NTC at T0; FIG. 5C: Amplification of cDNA at T24; and FIG. 5D: Amplification of NTC at T24.

FIGS. 6A-1 through 6E: Nucleic acid amplification using Power SYBR® Green PCR Master Mix and Platinum® Taq Antibody, alone or in combination. FIG. 6A-1 through 6B-2: Melt curve analysis of A2M using Power SYBR® Green PCR Master Mix alone at T0 and T24; FIG. 6C-1 through 6D-2: Melt curve analysis of A2M using a combination of Power SYBR® Green PCR Master Mix and Platinum® Taq Antibody at T0 and T24; FIG. 6E: Melt curve analysis of Power SYBR® Green PCR Master Mix and Platinum® Taq Antibody, alone or in combination.

DETAILED DESCRIPTION

Figure 1A:
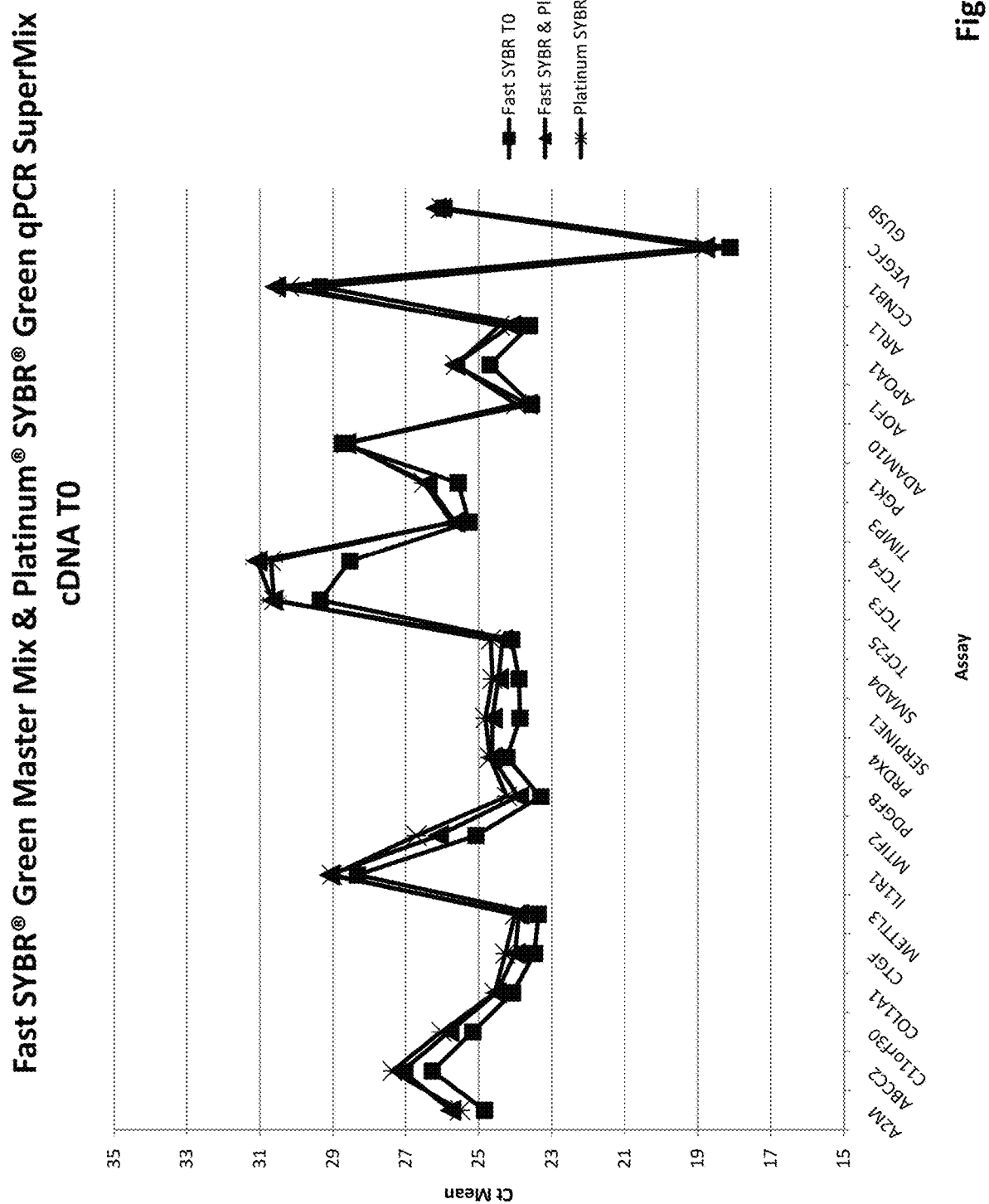
FIGS. 1A through 1D: Comparison of Fast SYBR® Green Master Mix alone ("square" line), Platinum® SYBR® Green qPCR Master Mix alone ("cross" line) and Fast SYBR® Green Master Mix in combination with Platinum® SYBR® Green qPCR Master Mix at a 1:1 ratio ("triangle" line).
Figure 1B:
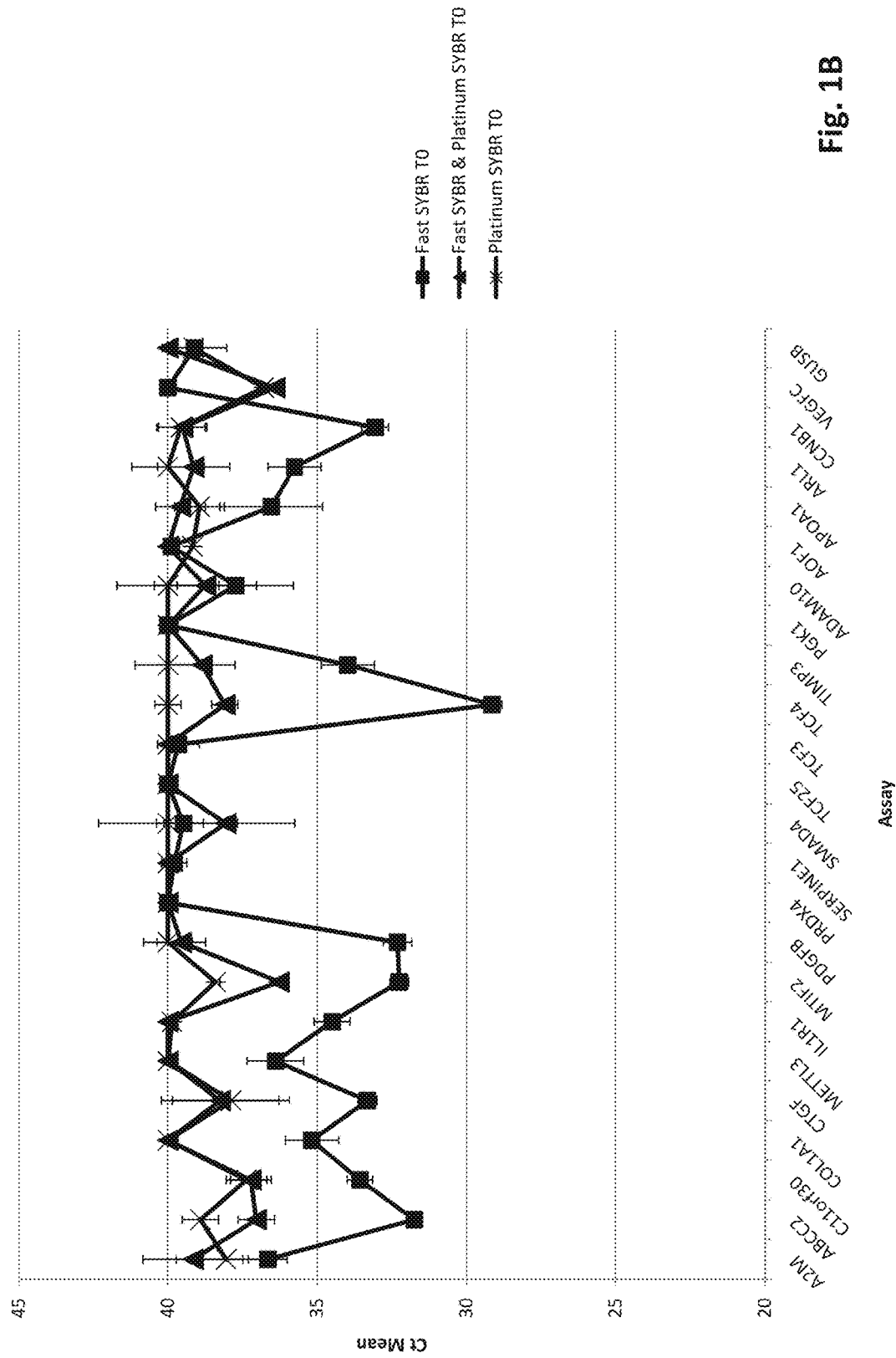
Figure 1C:
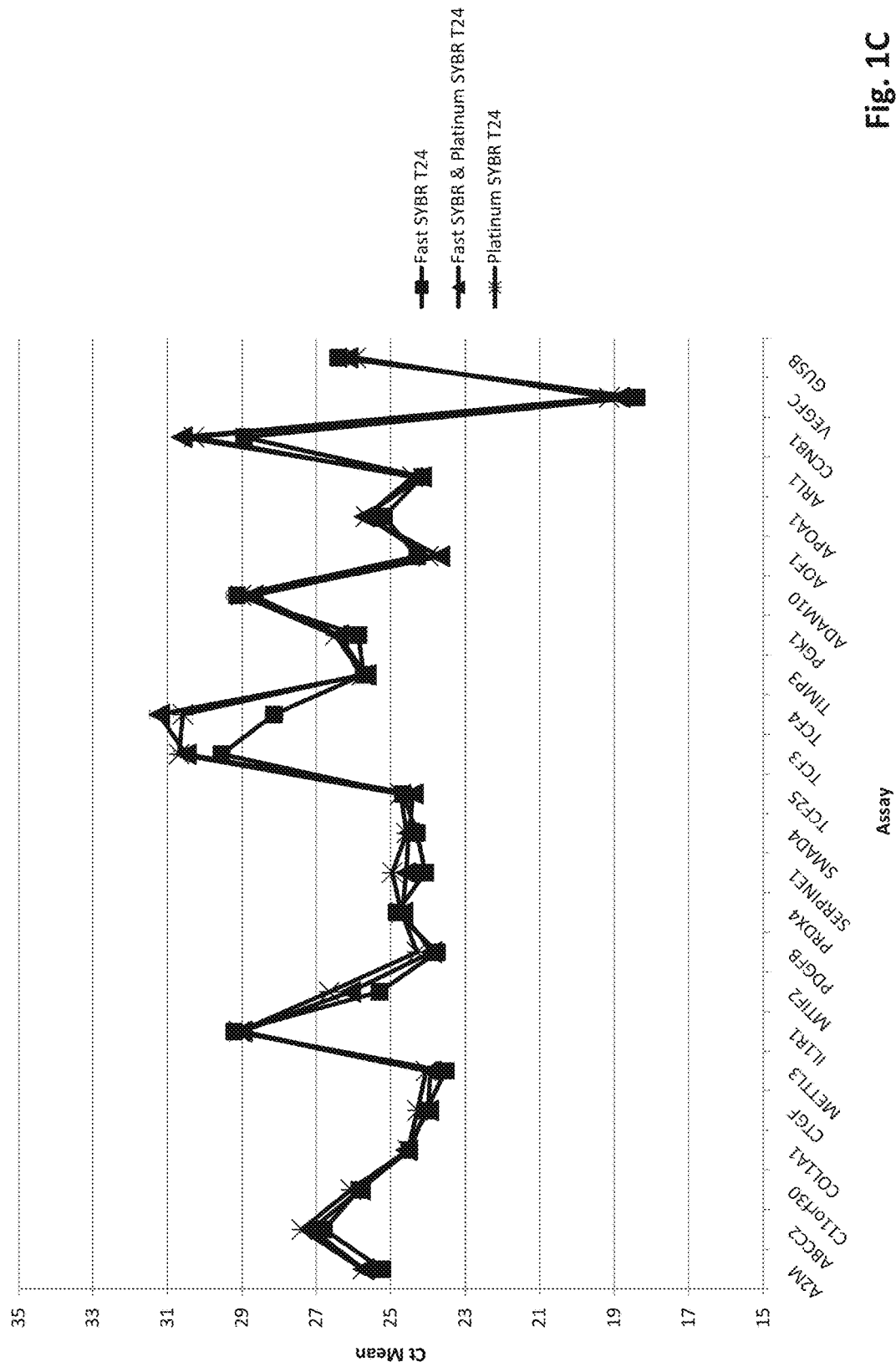
Figure 1D:
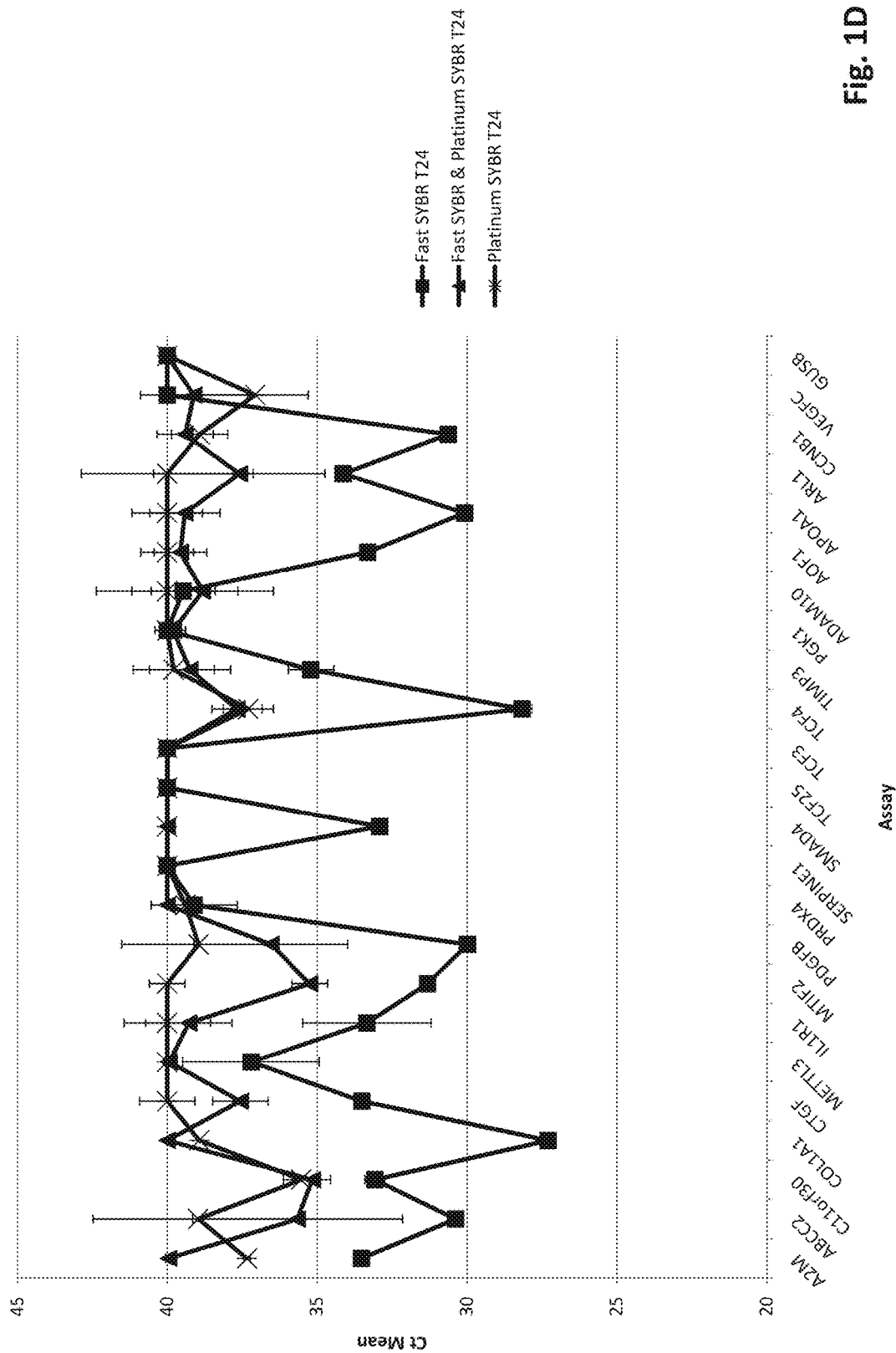

In certain embodiments, compositions are provided that comprise a nucleic acid polymerase and a dual hot start reaction mixture that inhibits or substantially inhibits the polymerase activity of the nucleic acid polymerase at a first temperature (e.g., <40° C. temperature). In some embodiments, the dual hot start reaction mixture comprises at least two different hot start mechanisms that are used to inhibit or substantially inhibit the polymerase activity of a nucleic acid polymerase at a first (e.g., lower) temperature. Such hot start mechanisms can include, for example, but are not limited to, antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers, or modified dNTPs.

In certain embodiments, the dual hot start reaction mixture inhibits non-specific nucleic acid amplification and/or non-specific product formation for extended periods of time compared to conventional hot start mechanisms. For example, in some embodiments, the present dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, compositions are provided that comprise a thermostable nucleic acid polymerase and a dual hot start reaction mixture that inhibits or substantially inhibits the polymerase activity of the nucleic acid polymerase at a temperature less than about 40° C. and such that the dual hot start reaction mixture does not substantially inhibit the polymerase activity of the nucleic acid polymerase at a temperature greater than about 40° C. In certain embodiments, the nucleic acid polymerase may be a DNA-dependent DNA polymerase or an RNA-dependent DNA polymerase. In certain embodiments, the nucleic acid polymerase may be thermostable.

In certain embodiments, methods for inhibiting the polymerase activity of a nucleic acid polymerase are provided. These methods involve contacting the polymerase with a dual hot start reaction mixture, where the dual hot start reaction mixture inhibits or substantially inhibits the polymerase activity of the nucleic acid polymerase at a first temperature (e.g., <40° C. temperature). Polymerase inhibition may be reversible (e.g., by heating to a second temperature of at least about 40° C.). The dual hot start reaction mixture comprises at least two different hot start mechanisms that are used to inhibit or substantially inhibit the polymerase activity of a nucleic acid polymerase at a first temperature. Such hot start mechanisms include, but are not limited to, antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers, or modified dNTPs. In certain embodiments, the nucleic acid polymerase may be a DNA-dependent DNA polymerase or an RNA-dependent DNA polymerase. In certain embodiments, the nucleic acid polymerase may be thermostable.

In certain embodiments, methods for synthesizing a nucleic acid molecule are provided. Such methods involve contacting a template nucleic acid with a composition comprising a thermostable nucleic acid polymerase, a dual hot start reaction mixture, one or more nucleoside and/or deoxynucleoside triphosphates and at least one primer, wherein the dual hot start reaction mixture inhibits or substantially inhibits polymerase activity of the nucleic acid polymerase at first temperature, bringing the resulting mixture to a second temperature sufficient to relieve polymerase inhibition, and polymerizing the template nucleic acid. In some embodiments, the first temperature is an ambient temperature (e.g., room temperature). In certain embodiments, the nucleic acid polymerase may be a DNA-dependent DNA polymerase or an RNA-dependent DNA polymerase. In certain embodiments, the nucleic acid polymerase may be thermostable.

In certain embodiments, methods for preventing or reducing mis-priming events comprising a dual hot start reaction mixture are provided. According to such methods, a nucleic acid polymerase is contacted with the dual hot start reaction mixture at a first temperature under conditions suitable for the dual hot start reaction mixture to substantially inhibit polymerase activity of the nucleic acid polymerase. When the resulting mixture is heated to a suitable second temperature, the dual hot start mechanism is halted from inhibiting the polymerase or polymerase activity and primer extension is allowed to occur.

In certain embodiments, methods for reducing non-specific amplification product formation comprising a dual hot start reaction mixture are provided. According to such methods, a target nucleic acid is contacted with a nucleic acid polymerase, a dual hot start reaction mixture, at least one primer and at least one dNTP. In certain embodiments, the at least one primer comprises a primer pair. At the first temperature, the dual hot start reaction mixture inhibits or substantially inhibits polymerase activity of the nucleic acid polymerase. The reaction composition is subsequently heated to a second temperature that prevents the dual hot start reaction from inhibiting the nucleic acid polymerase. The target nucleic acid in the reaction composition can then be subjected to at least one cycle of amplification. In certain embodiments the nucleic acid polymerase is thermostable. In certain other embodiments the nucleic acid polymerase is a DNA-dependent DNA polymerase or an RNA-dependent DNA polymerase. For example, the nucleic acid polymerase may be selected from the group consisting of, but not limited to, Taq DNA polymerase, Tfl DNA polymerase, Tfi DNA polymerase, Pfu DNA polymerase, and Vent™ DNA polymerase. In some other embodiments, the dual hot start reaction mixture comprises at least two different hot start mechanisms. In some embodiments, the at least two different hot start mechanisms can be selected from the group consisting of antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers, or modified dNTPs.

In certain embodiments, the dual hot start reaction mixture provides increased inhibition of non-specific nucleic acid amplification and/or non-specific product formation compared to conventional hot start mechanisms. In other embodiments, the dual hot start reaction mixture inhibits non-specific nucleic acid amplification and/or non-specific product formation for extended periods of time compared to conventional hot start mechanisms. For example, in some embodiments, the dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, methods for reducing non-specific fluorescence comprise a dual hot start reaction mixture are provided. According to such methods, a reaction composition is formed at a first temperature comprising a nucleic acid polymerase, a dual host start reaction mixture, at least one NTP or dNTP, a target nucleic acid, at least one primer and at least one nucleic acid binding dye. In certain embodiments, the at least one primer comprises a primer pair. At the first temperature, the dual hot start reaction mixture inhibits or substantially inhibits polymerase activity of the nucleic acid polymerase. The reaction composition is subsequently heated to a second reaction temperature that causes the dual hot start reaction mixture to allow nucleic acid polymerase activity to occur. The reaction composition is subjected to at least one cycle of amplification and a multiplicity of amplicons is generated. The double-stranded amplicons may be detected, either in "real time" or after the amplification reaction is completed due to the fluorescence of the nucleic acid binding dye associated with the amplicons.

In certain embodiments, the dual hot start reaction mixture inhibits non-specific nucleic acid amplification and/or non-specific product formation for extended periods of time compared to conventional hot start mechanisms. For example, in some embodiments, the present dual hot start reaction mixture inhibits non-specific nucleic acid amplification and/or non-specific product formation for at least 24 hours at ambient temperature. In certain embodiments, the dual hot start reaction mixture decreases non-specific amplification and/or non-specific product formation by about 20-100% as compared to a hot start reaction mixture having only a single hot start mechanism. In certain embodiments, the dual hot start reaction mixture decreases non-specific amplification and/or non-specific product formation by about 20, 25, 30, 35, 40, 45, 50, 55, 60, 65, 70, 75, 80, 85, 90, 95, or 100%. In certain embodiments, the dual hot start reaction mixture reduces non-specific product formation by about 2- to 4-fold as compared to a reaction mixture having only a single hot start mechanism. In certain embodiments, the dual hot start reaction mixture reduces non-specific product formation by about 2-, 2.5-, 3-, 3.5-, or 4-fold.

In certain embodiments, methods for amplifying a target nucleic acid using the dual hot start reaction mixture are provided. According to certain such methods, a reaction composition is formed at a first temperature comprising a nucleic acid polymerase, a dual host start reaction mixture, at least one NTP or dNTP, a target nucleic acid, at least one primer and at least one nucleic acid binding dye. In certain embodiments, the at least one primer comprises a primer pair. At the first temperature, the dual hot start reaction mixture inhibits or substantially inhibits polymerase activity of the nucleic acid polymerase. The reaction composition is subsequently heated to a second reaction temperature that causes the dual hot start reaction mixture to halt inhibition of the nucleic acid polymerase or nucleic acid polymerase activity. The reaction composition is subjected to at least one cycle of amplification and a multiplicity of amplicons is generated. The double-stranded amplicons may be detected, either in "real time" or after the amplification reaction is completed due to the fluorescence of the nucleic acid binding dye associated with the amplicons.

In certain embodiments, kits for performing certain of the instant methods are also provided. In certain embodiments, the kits comprise a dual hot start reaction mixture. In certain embodiments, the kits further comprise at least one nucleic acid polymerase. In certain embodiments, the kits further comprise one or more of: at least one primer or a primer pair, a nucleic acid binding dye, a reporter probe, and a reverse transcriptase.

To more clearly and concisely describe and point out the subject matter of the present disclosure, the following definitions are provided for specific terms, which are used in the following description and the appended claims. Throughout the specification, exemplification of specific terms should be considered as non-limiting examples.

As used in this specification, the words "a" or "an" means at least one, unless specifically stated otherwise. In this specification, the use of the singular includes the plural unless specifically stated otherwise. For example, but not as a limitation, "a target nucleic acid" means that more than one target nucleic acid can be present; for example, one or more copies of a particular target nucleic acid species, as well as two or more different species of target nucleic acid. The term "and/or" means that the terms before and after the slash can be taken together or separately. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. All literature cited in the specification, including but not limited to, patent, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The terms "amplicon" and "amplification product" as used herein generally refer to the product of an amplification reaction. An amplicon may be double-stranded or single-stranded, and may include the separated component strands obtained by denaturing a double-stranded amplification product. In certain embodiments, the amplicon of one amplification cycle can serve as a template in a subsequent amplification cycle.

The terms "annealing" and "hybridizing", including, without limitation, variations of the root words "hybridize" and "anneal", are used interchangeably and mean the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in *Nucleic Acid Hybridization, A Practical Approach*, Hames and Higgins, eds., IRL Press, Washington, D.C. (1985) and Wetmur and Davidson, *Mol. Biol.* 31:349 (1968).

In general, whether such annealing takes place is influenced by, among other things, the length of the complementary portions of the complementary portions of the primers and their corresponding binding sites in the target flanking sequences and/or amplicons, or the corresponding complementary portions of a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "selectively hybridize" and variations thereof, means that, under appropriate stringency conditions, a given sequence (for example, but not limited to a primer) anneals with a second sequence comprising a complementary string of nucleotides (for example, but not limited to a target flanking sequence or primer binding site of an amplicon), but does not anneal to undesired sequences, such as non-target nucleic acids, probes, or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize or selectively hybridize to one another, and situations where only a portion of one or both of the sequences hybridizes or selectively hybridizes to the entire other sequence or to a portion of the other sequence.

As used herein, the term "stringency" is used to define the temperature and solvent composition existing during hybridization and the subsequent processing steps at which a hybrid comprised of two complementary nucleotide sequences will form. Stringency also defines the amount of homology, the conditions necessary, and the stability of hybrids formed between two nucleotide sequences. As the stringency conditions increase, selective hybridization is favored and non-specific cross-hybridization is disfavored. Increased stringency conditions typically correspond to higher incubation temperature, lower salt concentrations, and/or higher pH, relative to lower stringency conditions at which mis-priming is more likely to occur. Those in the art understand that appropriate stringency conditions to enable the selective hybridization of a primer or primer pair to a corresponding target flanking sequence and/or amplicon can be routinely determined using well known techniques and without undue experimentation (see, e.g., *PCR: The Basics from Background to Bench*, McPherson and Moller, Bios Scientific Publishers, 2000).

As used herein, dual hot start reaction mixtures or mechanisms that "substantially inhibit" polymerase activity refers to reaction mixtures that provide less than about 30%, less than about 25%, less than about 20%, more preferably less than about 15%, less than about 10%, less than about 7.5%, or less than about 5%, and most preferably less than about 5%, less than about 2%, less than about 1%, less than about 0.5%, less than about 0.25% polymerase activity, or which lack polymerase activity altogether. Polymerase activity that is "substantially inhibited" as used herein refers to polymerase activity that is at least about 70%, 75%, 80%, 85%, 90%, 95%, 97.5%, 99%, 99.75%, 100% or >100% inhibited in the presence of said hot start mechanisms or hot start reaction mixtures.

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The terms "denaturing" and "denaturation" as used herein refer to any process in which a double-stranded polynucleotide, including without limitation, a genomic DNA (gDNA) fragment comprising at least one target nucleic acid, a double-stranded amplicon, or a polynucleotide comprising at least one double-stranded segment is converted to two single-stranded polynucleotides or to a single-stranded or substantially single-stranded polynucleotide, as appropriate. Denaturing a double-stranded polynucleotide includes, without limitation, a variety of thermal and chemical techniques which render a double-stranded nucleic acid single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction, or in certain methods, the detection of a fluorescent signal.

As used herein, the term "Tm" is used in reference to melting temperature. The melting temperature is the temperature at which a population of double-stranded nucleic acid molecules becomes half dissociated into single strands.

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example, but not limited to, furan, benzene, or pyrrole rings.

"Mis-priming" or "mis-primed" as used herein, refer to the hybridization of a primer or a probe to a non-target nucleic acid. As is known in the art, primers (excluding random primers) are generally designed to hybridize to a selected sequence that flanks a target nucleic acid or to a primer binding site of an amplicon and to direct DNA synthesis or primer extension starting at that site. Mis-priming may occur when a primer or a probe hybridizes to a non-target nucleic acid, oftentimes at low or decreased stringency conditions, and then serves as the initiation point for primer extension from that non-target site, giving rise to synthesis of certain undesired secondary amplification products.

The terms "non-specific" or "background" when used in reference to fluorescence refers to the detectable signal emitted from nucleic acid binding dye molecules associated with double-stranded nucleic acids other than desired amplicons. Desired amplicons comprise the amplification products of target nucleic acids, including in some embodiments, internal standard or control sequences that may be included in certain reaction compositions of the current teachings for, among other things, normalization and/or quantitation purposes. Thus, the fluorescent signal resulting from the association of nucleic acid dye molecules with spurious, secondary amplicons, often the result of mis-priming, mis-ligation, and/or primer-dimer formation, is one source of non-specific fluorescence.

The term "nucleic acid binding dye" as used herein refers to a fluorescent molecule that is specific for a double-stranded polynucleotide or that at least shows a substantially greater fluorescent enhancement when associated with double-stranded polynucleotides than with a single stranded polynucleotide. Typically, nucleic acid binding dye molecules associate with double-stranded segments of polynucleotides by intercalating between the base pairs of the double-stranded segment, but binding in the major or minor grooves of the double-stranded segment, or both. Non-limiting examples of nucleic acid binding dyes include ethidium bromide, DAPI, Hoechst derivatives including without limitation Hoechst 33258 and Hoechst 33342, intercalators comprising a lanthanide chelate (for example, but not limited to, a naphthalene diimide derivative carrying two fluorescent tetradentate β-diketone-$Eu^{3+}$ chelates (NDI-(BHHCT-$Eu^{3+}$)$_2$), see e.g., Nojima et al., *Nucl. Acids Res. Suppl. No. 1* 105 (2001), and certain unsymmetrical cyanine dyes such as SYBR® Green and PicoGreen®.

As used herein, the terms "polynucleotide", "oligonucleotide," and "nucleic acid" are used interchangeably and refer to single-stranded and double-stranded polymers of nucleotide monomers, including without limitation, 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and may include nucleotide analogs. The nucleotide monomer units may comprise any of the nucleotides described herein, including, but not limited to, nucleotides and/or nucleotide analogs. Polynucleotides typically range in size from a few monomeric units, e.g., 5-40 when they are sometimes referred to in the art as oligonucleotides, to several thousands of monomeric nucleotide units. Unless denoted otherwise, whenever a polynucleotide sequence is represented, it will be understood that the nucleotides are in the 5'-to-3' order from left to right and that "A" denotes deoxyadenosine, "C" denotes deoxycytosine, "G" denotes deoxyguanosine, "T" denotes deoxythymidine, and "U" denotes deoxyuridine, unless otherwise noted.

The term "nucleotide" refers to a phosphate ester of a nucleoside, e.g., triphosphate esters, wherein the most common site of esterification is the hydroxyl group attached at the C-5 position of the pentose.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms. When the nucleoside base is purine or 7-deazapurine, the pentose is attached to the nucleobase at the 9-position of the purine or deazapurine, and when the nucleobase is purimidine, the pentose is attached to the nucleobase at the 1-position of the pyrimidine.

The term "analog" includes synthetic analogs having modified base moieties, modified sugar moieties, and/or modified phosphate ester moieties. Phosphate analogs generally comprise analogs of phosphate wherein the phosphorous atom is in the +5 oxidation state and one or more of the oxygen atoms is replaced with a non-oxygen moiety, e.g. sulfur. Exemplary phosphate analogs include: phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$. Exemplary base analogs include: 2,6-diaminopurine, hypoxanthine, pseudouridine, C-5-propyne, isocytosine, isoguanine, 2-thiopyrimidine. Exemplary sugar analogs include: 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, and bromo.

As used herein, the term "reaction vessel" generally refers to any container, chamber, device, or assembly, in which a reaction can occur in accordance with the present teachings. In some embodiments, a reaction vessel may be a microtube, for example, but not limited to, a 0.2 mL or a 0.5 mL reaction tube such as a MicroAmp® Optical tube (Life Technologies Corp., Carslbad, Calif.) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation a TaqMan® Low Density Array or a TaqMan® Open Array Real-Time PCR plate (both from Life Technologies Corp.). For example, but not as a limitation, a plurality of reaction vessels can reside on the same support. In some embodiments, lab-on-α-chip-like devices available, for example, from Caliper, Fluidigm and Life Technologies Corp., including the Ion 316™ and Ion 318™ Chip, may serve as reaction vessels in the disclosed methods. It will be recognized that a variety of reaction vessels are commercially available or can be designed for use in the context of the present teachings.

As used herein, the term "hot start" generally refers to a means of limiting the availability of an essential reaction component (e.g., a polymerase) when the reaction mixture is maintained at a first temperature (typically a lower temperature) until a second temperature (typically a higher temperature) is reached which allows the essential component to participate in the reaction. Hot start reactions typically involve incubation at a first (e.g., lower) temperature and subsequent elevation to a second (e.g., higher) temperature which allows the desired reaction to take place. Activation of the hot start reaction is preferably achieved by an incubation at a temperature which is equal to or higher than the primer hybridization (annealing) temperature used in the amplification reaction to ensure primer binding specificity. The length of incubation required to recover enzyme activity depends on the temperature and pH of the reaction mixture and on the stability of the enzyme. A wide range of incubation conditions are usable; optimal conditions may be determined empirically for each reaction. In general, a dual hot start reaction mixture is incubated at a first temperature to inhibit nucleic acid synthesis (e.g., polymerase activity) and then elevated to a second temperature for inhibition to be relieved or halted. Optimization of incubation conditions for the reactivation of nucleic acid polymerases not exemplified, or for reaction mixtures not exemplified, can be determined by routine experimentation following the guidance provided herein.

In certain embodiments the first temperature is lower than said second temperature. In some embodiments the first temperature is <40° C. In certain embodiments the first temperature is about equal to or less than about 40° C., 35° C., 30° C., 25° C., 20° C., 15° C., 10° C., 5° C., or less. In some embodiments, the first temperature is ambient temperature. In some other embodiments, the first temperature is room temperature. In some embodiments the second temperature is >40° C. In certain embodiments the first temperature is about equal to or greater than about 40° C., 45° C., 50° C., 55° C., 60, 65° C., 70° C., 75° C., 80° C., 85° C., 90° C., 95° C., 100° C., or more. Several methods exist for performing hot start reactions including, but not limited to, the use of manual techniques, barriers, chemical modifications and/or structural modifications of one or more of the essential reaction components. Suitable reaction conditions for such hot start methods are know in the art and further described herein and in the Examples.

As used herein, the term "dual hot start reaction mixture" refers to the combination of reagents or reagent solutions which are used to block nucleic acid polymerase extension at low temperatures (e.g., ambient temperature) until the hot start conditions of the initial denaturation temperature in an amplification reaction (e.g., PCR) are reached. At the elevated amplification temperature, the nucleic acid polymerase is no longer inhibited and allows for primer extension. As used herein, the dual hot start reaction mixture is meant to include an reaction mixture that comprises at least two different mechanisms for hot start. Accordingly, "dual hot start reaction mixtures" may include more than two hot start mechanisms (e.g., "triple hot start reaction mixture", "quadruple hot start reaction mixture", "quintuple hot start reaction mixture", and so on). Possible hot start mechanisms may include, but are not limited to, antibodies or combinations of antibodies that block nucleic acid polymerase activity at lower temperatures and which dissociate from the polymerase at elevated temperatures (see, e.g., Eastlund et al., *LifeSci. Quarterly* 2:2 (2001), Mizuguchi et al., *J. Biochem.* (Tokyo) 126:762 (1999)); oligonucleotides that block nucleic acid polymerase activity at lower temperatures and which dissociate from the polymerase at elevated temperatures (see, e.g., Dang et al., *J. Mol. Biol.* 264:268 (1996)); reversibly chemical modification of the nucleic acid polymerase such that the nucleic acid polymerase activity is blocked at lower temperatures and the modifications reverse or dissociate at elevated temperatures (see, e.g., U.S. Pat. No. 5,773,258 and Moretti et al., *Biotechniques* 25:716 (1998)); amino acid mutations of the nucleic acid polymerase that provide reduced activity at lower temperatures (see, e.g., Kermekchiev et al., *Nucl. Acids Res.* 31:6139 (2003)); nucleic acid polymerase fusion proteins including hyperstable DNA binding domains and topoisomerases (see, e.g., Pavlov et al., *Proc. Natl. Acad. Sci. USA* 99:13510 (2002)); ligands that inhibit the nucleic acid polymerase in a temperature-dependent manner (for example, HotMaster™ Taq DNA polymerase from Eppendorf (Hauppauge, N.Y.) and 5 PRIME (Gaithersburg, Md.)); single-stranded binding proteins that sequester primers at low temperatures (see, e.g., U.S. Patent Application Publication No. 2008/0138878); thermostable pyrophosphatase which hydrolyzes inorganic pyrophosphate at elevated temperatures (see, e.g., U.S. Patent Application Publication No. 2006/0057617); thermolabile blockers, such as a polymerase blocking protein (see, e.g., U.S. Patent Application Publication No. 2007/0009922); primer competitor sequences (see, e.g., Puskas et al., *Genome Res.* 5:309 (1995) and Vestheim et al., *Front. Zool.* 5:12 (2008)); modified primer constructs (see, e.g., Ailenberg et al., *Biotechniques* 29:22 (2000) and Kaboev et al., *Nucl. Acids Res.* 28:E94 (2000)); modified primers that improve hybridization selectivity (see, e.g., U.S. Pat. Nos. 6,794,142 and 6,001,611); primers with 3' modifications that are removable by 3'-5' exonuclease activity (see, e.g., U.S. Patent Application Publication No. 2003/0119150 and U.S. Pat. No. 6,482,590); primers with modified nucleobases that are removable by UV irradiation (see, e.g., Young et al., *Chem. Commun.* (Camb 28:462 (2008)); primer modifications that are removable by thermal deprotection (see, e.g., U.S. Patent Application Publication No. 2003/0162199 and Lebedev et al., *Nucl. Acids Res.* 36:e131 (2008)); or modification of the dNTPs with thermolabile modification groups (see, e.g., U.S. Patent Application Publication No. 2003/0162199 and Koukhareva et al., *Nucl. Acids Symp. Ser.* (Oxford), 259 (2008)). All references cited herein are incorporated by reference in their entirety for all purposes.

As used herein, dual hot start reaction mixtures comprising "at least two different mechanisms" encompass those reaction mixtures that may comprise at least two different hot start mechanisms that function similarly or use similar components. For example, dual hot start reaction mixtures can comprise reagents or reagent solutions designed for two different antibody-based hot start mechanisms, or two different oligonucleotide-based hot start mechanisms, or one antibody-based and one oligonucleotide-based hot start mechanism, or one antibody-based and one chemical modification-based hot start mechanism, or any such combination available.

The term "reporter group" is used in a broad sense herein and refers to any identifiable tag, label, or moiety.

The term "target nucleic acid" or "target" refers to the nucleic acid sequence that is specifically amplified and/or detected using the compositions, methods and kits of the present teachings (in contrast to a secondary amplification product, which is the result of a spurious side-reaction, typically due to mis-priming). In certain embodiments, a target nucleic acid serves as a template in a primer extension reaction. In some embodiments, a target nucleic acid serves as an amplification template. In some embodiments, a target nucleic acid serves as a template strand in a nucleic acid cleavage structure. In certain embodiments, the target nucleic acid comprises DNA and is present in genomic DNA (gDNA) or mitochondrial DNA (mtDNA). In certain embodiments, the target nucleic acid comprises RNA, for example but not limited to, ribosomal RNA (rRNA), messenger RNA (mRNA), transfer RNA (tRNA), or an RNA molecule such as a micro RNA (miRNA) precursor, including without limitation, a pri-miRNA, a pre-miRNA, or a pri-miRNA and a pre-miRNA. In some embodiments, the target nucleic acid comprises a small RNA molecule including without limitation, a miRNA, a sRNA, a stRNA, a snoRNA, or other ncRNA. The target nucleic acid need not constitute the entirety of a nucleic acid molecule. For example, but not as a limitation, a large nucleic acid, for example, a gDNA fragment, may comprise a multiplicity of different target nucleic acids. Typically, a target nucleic acid has at least one defined end. In many nucleic acid amplification reactions, the nucleic acid target has two defined ends.

The term "thermostable" when used in reference to an enzyme, refers to an enzyme (such as a polypeptide having nucleic acid polymerase activity) that is resistant to inactivation by heat. A "thermostable" enzyme is in contrast to a "thermolabile" polymerase, which can be inactivated by heat treatment. Thermolabile proteins can be inactivated at physiological temperatures, and can be categorized as mesothermostable (inactivation at about 45° C. to about 65° C.), and thermostable (inactivation at greater than about 65° C.). For example, the activities of the thermolabile T5 and T7 DNA polymerases can be totally inactivated by exposing the enzymes to a temperature of about 90° C. for about 30 seconds. A thermostable polymerase activity is more resistant to heat inactivation than a thermolabile polymerase. However, a thermostable polymerase does not mean to refer to an enzyme that is totally resistant to heat inactivation; thus heat treatment may reduce the polymerase activity to some extent. A thermostable polymerase typically will also have a higher optimum temperature than thermolabile DNA polymerases.

Working concentration refers to the concentration of a reagent that is at or near the optimal concentration used in a solution to perform a particular function (such as amplification or digestion of a nucleic acid molecule). The working concentration of a reagent is also described equivalently as a "1× concentration" or a "1× solution" (if the reagent is in solution) of the reagent. Accordingly, higher concentrations of the reagent may also be described based on the working concentration; for example, a "2× concentration" or a "2× solution" of a reagent is defined as a concentration or solution that is twice as high as the working concentration of the reagent; a "5× concentration" or a "5× solution" is five times as high as the working concentration, and so on.

As used herein, "nucleic acid polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" as used herein generally refers to any polypeptide that can catalyze the 5'-to-3' extension of a hybridized primer by the addition of catalyzes the polymerization of deoxynucleotides dideoxyribonucleotides, and/or certain nucleotide analogs in a template-dependent manner. For example, but not limited to, the sequential addition of deoxyribonucleotides to the 3'-end of a primer that is annealed to a nucleic acid template during a primer extension reaction. Non-limiting examples of DNA polymerases include RNA-dependent DNA polymerases, including without limitation, reverse transcriptases, and DNA-dependent DNA polymerases. Known DNA polymerases include, for example, *Pyrococcus furiosus* (Pfu) DNA polymerase (Lundberg et al., 1991, Gene, 108:1), *E. coli* DNA polymerase I (Lecomte and Doubleday, 1983, Nucleic Acids Res. 11:7505), T7 DNA polymerase (Nordstrom et al., 1981, J. Biol. Chem. 256:3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475: 32), *Thermococcus litoralis* (Tli) DNA polymerase (also referred to as Vent DNA polymerase, Cariello et al., 1991, Nucleic Acids Res, 19: 4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). The polymerase activity of any of the above enzyme can be determined by means well known in the art. One unit of DNA polymerase activity, according to the subject invention, is defined as the amount of enzyme which catalyzes the incorporation of 10 nmoles of total dNTPs into polymeric form in 30 minutes at optimal temperature (e.g., 72° C. for Pfu DNA polymerase). It is to be appreciated that certain DNA polymerases (for example, but not limited to certain eubacterial Type A DNA polymerases and Taq DNA polymerase) may further comprise a structure-specific nuclease activity. Reverse transcriptase enzymes suitable for the practice of the present invention are also well known in the art and can be derived from a number of sources. Such enzymes include, but are not limited to, M-MLV, HIV, ASLV and variants and mutants thereof.

As used herein, the terms "amplification", "nucleic acid amplification", or "amplifying" refer to the production of multiple copies of a nucleic acid template, or the production of multiple nucleic acid sequence copies that are complementary to the nucleic acid template. The terms (including the term "polymerizing") may also refer to extending a nucleic acid template (e.g., by polymerization). The amplification reaction may be a polymerase-mediated extension reaction such as, for example, a polymerase chain reaction (PCR). However, any of the known amplification reactions may be suitable for use as described herein. The term "amplifying" that typically refers to an "exponential" increase in target nucleic acid may be used herein to describe both linear and exponential increases in the numbers of a select target sequence of nucleic acid.

The term "amplification reaction mixture" and/or "master mix" may refer to an aqueous solution comprising the various (some or all) reagents used to amplify a target nucleic acid. Such reactions may also be performed using solid supports (e.g., an array). The reactions may also be performed in single or multiplex format as desired by the user. These reactions typically include enzymes, aqueous buffers, salts, amplification primers, target nucleic acid, and nucleoside triphosphates. Depending upon the context, the mixture can be either a complete or incomplete amplification reaction mixture. The method used to amplify the target nucleic acid may be any available to one of skill in the art. Any in vitro means for multiplying the copies of a target sequence of nucleic acid may be utilized. These include linear, logarithmic, and/or any other amplification method. While this disclosure may generally discuss PCR as the nucleic acid amplification reaction, it is expected that the modified detergents describe herein should be effective in other types of nucleic acid amplification reactions, including both polymerase-mediated amplification reactions (such as helicase-dependent amplification (HDA), recombinase-polymerase amplification (RPA), and rolling circle amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). For example, the modified detergents may be used in, for example, various ligation-mediated reactions, where for example ligation probes are employed as opposed to PCR primers. Additional exemplary methods include polymerase chain reaction (PCR; see, e.g., U.S. Pat. Nos. 4,683,202; 4,683,195; 4,965,188; and/or 5,035,996), isothermal procedures (using one or more RNA polymerases (see, e.g., PCT Publication No. WO 2006/081222), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., *Genomics* 4: 560-569 (1990)), and/or Barany, et al. *Proc. Natl. Acad. Sci. USA* 88:189-193 (1991)), Qβ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. *Nat. Genet.* 19: 225-232 (1998); and/or Bailer et al. *Nucleic Acid Res.*, 26: 5073-5078 (1998)), and strand displacement amplification (SDA) (Little, et al. *Clin. Chem.* 45:777-784 (1999)), among others. These systems, along with the many other systems available to the skilled artisan, may be suitable for use in polymerizing and/or amplifying target nucleic acids for use as described herein.

"Amplification efficiency" may refer to any product that may be quantified to determine copy number (e.g., the term may refer to a PCR amplicon, an LCR ligation product, and/or similar product). The amplification and/or polymerization efficiency may be determined by various methods known in the art, including, but not limited to, determination of calibration dilution curves and slope calculation, determination using qBase software as described in Hellemans et al., Genome Biology 8:R19 (2007), determination using the delta delta Cq (ΔΔCq) calculation as described by Livak and Schmittgen, *Methods* 25:402 (2001), or by the method as described by Pfaffl, *Nucl. Acids Res.* 29:e45 (2001), all of which are herein incorporated by reference in their entirety.

In general, PCR thermal cycling includes an initial denaturing step at high temperature, followed by a repetitive series of temperature cycles designed to allow template denaturation, primer annealing, and extension of the annealed primers by the polymerase. Generally, the samples are heated initially for about 2 to 10 minutes at a temperature of about 95° C. to denature the double stranded DNA sample. Then, in the beginning of each cycle, the samples are denatured for about 10 to 60 seconds, depending on the samples and the type of instrument used. After denaturing, the primers are allowed to anneal to the target DNA at a lower temperature, from about 40° C. to about 60° C. for about 20 to 60 seconds. Extension of the primers by the polymerase is often carried out at a temperature ranging from about 60° C. to about 72° C. The amount of time used for extension will depend on the size of the amplicon and the type of enzymes used for amplification and is readily determined by routine experimentation. Additionally, the annealing step can be combined with the extension step, resulting in a two step cycling. Thermal cycling may also include additional temperature shifts in PCR assays. The number of cycles used in the assay depends on many factors, including the primers used, the amount of sample DNA present, and the thermal cycling conditions. The number of cycles to be used in any assay may be readily determined by one skilled in the art using routine experimentation. Optionally, a final extension step may be added after the completion of thermal cycling to ensure synthesis of all amplification products.

PCR with the disclosed compositions can be performed on "standard" PCR instrumentation, e.g., Applied Biosystems 7900HT, 7500, and 7300 standard PCR systems, or on "fast" PCR instrumentation, e.g., Applied Biosystems StepOne™, StepOne Plus™, 7500 and 7900HT Fast Real-time PCR systems, or ViiA™ 7 or QuantStudio™ 12K Flex Real-Time PCR systems.

In some embodiments, exemplary thermal cycling conditions for PCR amplification using the compositions and methods disclosed herein are as follows:
  UNG Step (Optional): 50° C. for 2 minutes
  Activation: 95° C. for 2 minutes
  Denaturation: 95-97° C. for 15 seconds
  Annealing/Extension: 60-62° C. for 1 minute (× up to 40 cycles)

In some embodiments, exemplary thermal cycling conditions for PCR amplification using the compositions and methods disclosed herein are as follows:
  UNG Step (Optional): 50° C. for 2 minutes
  Activation: 95° C. for 2 minutes
  Denaturation: 95-97° C. for 15 seconds
  Annealing: 55-60° C. for 15 seconds
  Extension: 72° C. for 1 minute (× up to 40 cycles)

In some embodiments, the compositions disclosed herein are used for fast PCR thermal cycling. In one embodiment, fast thermal cycling conditions for PCR amplification using the composition and methods disclosed herein are as follows:

UNG Step (Optional): 50° C. for 2 minutes
Activation: 95° C. for 2 minutes
Denaturation: 95-97° C. for 1-3 seconds
Extension: 60-62° C. for 20-30 seconds (× up to 40 cycles)

In some embodiments, when fast PCR thermal cycling is performed a primer concentration of about 400 nM is recommended.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. The cycle may or may not be repeated. In certain embodiments, a cycle of amplification comprises a multiplicity of amplification cycles, for example, but not limited to 20 cycles, 25 cycles, 30 cycles, 35 cycles, 40 cycles, 45 cycles or more than 45 cycles of amplification.

In some embodiments, amplifying comprises thermal cycling using an instrument, such as, but not limited to, a GeneAmp® PCR System 9700, 9600, 2700 or 2400 thermocycler, a QuantStudio™ 12K Flex Real-Time PCR System, an Applied Biosystems® ViiA™ 7 Real-Time PCR System, an Applied Biosystems® 7500 Fast Real-Time PCR System, a 7900HT Fast Real-Time PCR System, and the like (all available from Life Technologies Corp., Carlsbad, Calif.). In certain embodiments, single-stranded amplicons are generated in an amplification reaction, for example, but not limited to asymmetric PCR or A-PCR.

Devices have been developed that can perform a thermal cycling reaction with and detection of reaction compositions containing a nucleic acid binding dye, by emitting a light beam of a specified wavelength, reading the intensity of the fluorescent signal emitted from the nucleic acid binding dye molecules associated with double-stranded nucleic acids, and displaying the intensity of fluorescence after each cycle. Devices comprising a thermal cycler, light beam emitter, and a fluorescent signal detector have been described in, e.g., U.S. Pat. Nos. 5,928,907; 6,015,674; and 6,174,670, and include without limitation, the ABI Prism® 7700 Sequence Detection System, the GeneAmp® PCR System 9700, 9600, 2700 or 2400 thermocycler, the Applied Biosystems® ViiA™ 7 Real-Time PCR System, the Applied Biosystems® 7500 Fast Real-Time PCR System, the 7900HT Fast Real-Time PCR System, and the like (all available from Life Technologies Corp., Carlsbad, Calif.).

In some embodiments, amplification comprises a two-step reaction including without limitation, a pre-amplification step wherein a limited number of cycles of amplification occur (for example, but not limited to, 2, 3, 4, or 5 cycles of amplification), then the resulting amplicon is generally diluted and portions of the diluted amplicon are subjected to additional cycles of amplification in a subsequent amplification step (see, e.g., U.S. Pat. No. 6,605,451 and U.S. Patent Application Publication No. 2004/0175733). In some embodiments, a pre-amplification step, a subsequent amplification step, or both, includes a dual hot start reaction mixture.

In certain embodiments, an amplification reaction comprises multiplex amplification, in which a multiplicity of different target nucleic acids and/or a multiplicity of different amplification product species are simultaneously amplified using a multiplicity of different primer sets. In certain embodiments, a multiplex amplification reaction and a single-plex amplification reaction, including a multiplicity of single-plex or lower-plexy reactions (for example, but not limited to a two-plex, a three-plex, a four-plex, a five-plex or a six-plex reaction) are performed in parallel.

Exemplary methods for polymerizing and/or amplifying nucleic acids include, for example, polymerase-mediated extension reactions. For instance, the polymerase-mediated extension reaction can be the polymerase chain reaction (PCR). In other embodiments, the nucleic acid amplification reaction is a multiplex reaction. For instance, exemplary methods for polymerizing and/or amplifying and detecting nucleic acids suitable for use as described herein are commercially available as TaqMan® (see, e.g., U.S. Pat. Nos. 4,889,818; 5,079,352; 5,210,015; 5,436,134; 5,487,972; 5,658,751; 5,210,015; 5,487,972; 5,538,848; 5,618,711; 5,677,152; 5,723,591; 5,773,258; 5,789,224; 5,801,155; 5,804,375; 5,876,930; 5,994,056; 6,030,787; 6,084,102; 6,127,155; 6,171,785; 6,214,979; 6,258,569; 6,814,934; 6,821,727; 7,141,377; and/or 7,445,900, all of which are hereby incorporated herein by reference in their entirety). TaqMan® assays are typically carried out by performing nucleic acid amplification on a target polynucleotide using a nucleic acid polymerase having 5'-to-3' nuclease activity, a primer capable of hybridizing to said target polynucleotide, and an oligonucleotide probe capable of hybridizing to said target polynucleotide 3' relative to said primer. The oligonucleotide probe typically includes a detectable label (e.g., a fluorescent reporter molecule) and a quencher molecule capable of quenching the fluorescence of said reporter molecule. Typically, the detectable label and quencher molecule are part of a single probe. As amplification proceeds, the polymerase digests the probe to separate the detectable label from the quencher molecule. The detectable label (e.g., fluorescence) is monitored during the reaction, where detection of the label corresponds to the occurrence of nucleic acid amplification (e.g., the higher the signal the greater the amount of amplification). Variations of TaqMan® assays (e.g., LNA™ spiked TaqMan® assay) are known in the art and would be suitable for use in the methods described herein.

Another exemplary system suitable for use as described herein utilizes double-stranded probes in displacement hybridization methods (see, e.g., Morrison et al. *Anal. Biochem.*, 18:231-244 (1989); and/or Li, et al. *Nucleic Acids Res.*, 30(2,e5) (2002)). In such methods, the probe typically includes two complementary oligonucleotides of different lengths where one includes a detectable label and the other includes a quencher molecule. When not bound to a target nucleic acid, the quencher suppresses the signal from the detectable label. The probe becomes detectable upon displacement hybridization with a target nucleic acid. Multiple probes may be used, each containing different detectable labels, such that multiple target nucleic acids may be queried in a single reaction.

Additional exemplary methods for polymerizing and/or amplifying and detecting target nucleic acids suitable for use as described herein involve "molecular beacons", which are single-stranded hairpin shaped oligonucleotide probes. In the presence of the target sequence, the probe unfolds, binds and emits a signal (e.g., fluoresces). A molecular beacon typically includes at least four components: 1) the "loop", an 18-30 nucleotide region which is complementary to the target sequence; 2) two 5-7 nucleotide "stems" found on either end of the loop and being complementary to one another; 3) at the 5' end, a detectable label; and 4) at the 3' end, a quencher moiety that prevents the detectable label from emitting a single when the probe is in the closed loop shape (e.g., not bound to a target nucleic acid). Thus, in the presence of a complementary target, the "stem" portion of the beacon separates out resulting in the probe hybridizing to the target. Other types of molecular beacons are also known and may be suitable for use in the methods described herein. Molecular beacons may be used in a variety of assay systems. One such system is nucleic acid sequence-based amplification (NASBA®), a single step isothermal process for polymerizing and/or amplifying RNA to double stranded DNA without temperature cycling. A NASBA reaction typically requires avian myeloblastosis virus (AMV), reverse transcriptase (RT), T7 RNA polymerase, RNase H, and two oligonucleotide primers. After amplification, the amplified target nucleic acid may be detected using a molecular beacon. Other uses for molecular beacons are known in the art and would be suitable for use in the methods described herein.

The Scorpions™ system is another exemplary assay format that may be used in the methods described herein. Scorpions™ primers are bi-functional molecules in which a primer is covalently linked to the probe, along with a detectable label (e.g., a fluorophore) and a non-detectable quencher moiety that quenches the fluorescence of the detectable label. In the presence of a target nucleic acid, the detectable label and the quencher separate which leads to an increase in signal emitted from the detectable label. Typically, a primer used in the amplification reaction includes a probe element at the 5' end along with a "PCR blocker" element (e.g., a hexaethylene glycol (HEG) monomer (Whitcombe, et al. *Nat. Biotech.* 17: 804-807 (1999)) at the start of the hairpin loop. The probe typically includes a self-complementary stem sequence with a detectable label at one end and a quencher at the other. In the initial amplification cycles (e.g., PCR), the primer hybridizes to the target and extension occurs due to the action of polymerase. The Scorpions™ system may be used to examine and identify point mutations using multiple probes that may be differently tagged to distinguish between the probes. Using PCR as an example, after one extension cycle is complete, the newly synthesized target region will be attached to the same strand as the probe. Following the second cycle of denaturation and annealing, the probe and the target hybridize. The hairpin sequence then hybridizes to a part of the newly produced PCR product. This results in the separation of the detectable label from the quencher and causes emission of the signal. Other uses for such labeled probes are known in the art and would be suitable for use in the methods described herein.

In some embodiments, the methods are performed before or in conjunction with a sequencing reaction. The term "sequencing" is used in a broad sense herein and refers to any technique known in the art that allows the order of at least some consecutive nucleotides in at least part of a polynucleotide, for example but not limited to a target nucleic acid or an amplicon, to be identified. Some non-limiting examples of sequencing techniques include Sanger's dideoxy terminator method and the chemical cleavage method of Maxam and Gilbert, including variations of those methods; sequencing by hybridization; sequencing by synthesis; and restriction mapping. Some sequencing methods comprise electrophoresis, including capillary electrophoresis and gel electrophoresis; sequencing by hybridization including microarray hybridization; mass spectrometry; single molecule detection; and ion/proton detection. In some embodiments, sequencing comprises direct sequencing, duplex sequencing, cycle sequencing, single base extension sequencing (SBE), solid-phase sequencing, or combinations thereof. In some embodiments, sequencing comprises detecting the sequencing product using an instrument, for example but not limited to an ABI Prism® 377 DNA Sequencer, an ABI Prism® 310, 3100, 3100-Avant, 3730 or 3730xl Genetic Analyzer, an ABI Prism® 3700 DNA Analyzer, an Ion PGM™ sequencer, or an Ion Proton™ sequencer (all available from Life Technologies Corp., Carlsbad, Calif.), or a mass spectrometer. In some embodiments, sequencing comprises incorporating a dNTP, including a dATP, a dCTP, a dGTP, a dTTP, a dUTP, a dITP, or combinations thereof, and including dideoxyribonucleotide analogs of dNTPs, into an amplification product.

The nucleic acid polymerases that may be employed in the disclosed nucleic acid amplification reactions may be any that function to carry out the desired reaction including, for example, a prokaryotic, fungal, viral, bacteriophage, plant, and/or eukaryotic nucleic acid polymerase. As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'-to-3' direction. Since DNA polymerase can only add a nucleotide onto a pre-existing 3'-OH group, to begin a DNA synthesis reaction, the DNA polymerase needs a primer to which it can add the first nucleotide. Suitable primers may comprise oligonucleotides of RNA or DNA, or chimeras thereof (e.g., RNA/DNA chimerical primers). The DNA polymerases may be a naturally occurring DNA polymerases or a variant of natural enzyme having the above-mentioned activity. For example, it may include a DNA polymerase having a strand displacement activity, a DNA polymerase lacking 5'-to-3' exonuclease activity, a DNA polymerase having a reverse transcriptase activity, or a DNA polymerase having an endonuclease activity.

Suitable nucleic acid polymerases may also comprise holoenzymes, functional portions of the holoenzymes, chimeric polymerase, or any modified polymerase that can effectuate the synthesis of a nucleic acid molecule. Within this disclosure, a DNA polymerase may also include a polymerase, terminal transferase, reverse transcriptase, telomerase, and/or polynucleotide phosphorylase. Non-limiting examples of polymerases may include, for example, T7 DNA polymerase, eukaryotic mitochondrial DNA Polymerase γ, prokaryotic DNA polymerase I, II, III, IV, and/or V; eukaryotic polymerase α, β, γ, δ, ε, η, ξ, ι, and/or κc; *E. coli* DNA polymerase I; *E. coli* DNA polymerase III alpha and/or epsilon subunits; *E. coli* polymerase IV, *E. coli* polymerase V; *T. aquaticus* DNA polymerase I; *B. stearothermophilus* DNA polymerase I; *Euryarchaeota polymerases*; terminal deoxynucleotidyl transferase (TdT); *S. cerevisiae* polymerase 4; translesion synthesis polymerases; reverse transcriptase; and/or telomerase. Non-limiting examples of suitable thermostable DNA polymerases that may be used include Taq, Tfl, Tfi, Pfu, and Vent™ DNA polymerases, any genetically engineered DNA polymerases, any having reduced or insignificant 3'-to-5' exonuclease activity (e.g., SuperScript™ DNA polymerase), and/or genetically engineered DNA polymerases (e.g., those having the active site mutation F667Y or the equivalent of F667Y (e.g., in Tth), AmpliTaq®FS, ThermoSequenase™), AmpliTaq® Gold, Platinum® Taq DNA Polymerase, Therminator I, Therminator II, Therminator III, Therminator Gamma (all available from New England Biolabs, Beverly, Mass.), and/or any derivatives and fragments thereof. Other nucleic acid polymerases may also be suitable as would be understood by one of skill in the art.

In another aspect, the present disclosure provides reaction mixtures for polymerizing and/or amplifying a nucleic acid sequence of interest (e.g., a target sequence). In some embodiments, the reaction mixture may further comprise a detectable label. The methods may also include one or more steps for detecting the detectable label to quantitate the amplified nucleic acid. As used herein, the term "detectable label" refers to any of a variety of signaling molecules indicative of amplification. For example, SYBR® Green and other DNA-binding dyes are detectable labels. Such detectable labels may comprise or may be, for example, nucleic acid intercalating agents or non-intercalating agents. As used herein, an intercalating agent is an agent or moiety capable of non-covalent insertion between stacked base pairs of a double-stranded nucleic acid molecule. A non-intercalating agent is one that does not insert into the double-stranded nucleic acid molecule. The nucleic acid binding agent may produce a detectable signal directly or indirectly. The signal may be detectable directly using, for example, fluorescence and/or absorbance, or indirectly using, for example, any moiety or ligand that is detectably affected by proximity to double-stranded nucleic acid is suitable such as a substituted label moiety or binding ligand attached to the nucleic acid binding agent. It is typically necessary for the nucleic acid binding agent to produce a detectable signal when bound to a double-stranded nucleic acid that is distinguishable from the signal produced when that same agent is in solution or bound to a single-stranded nucleic acid. For example, intercalating agents such as ethidium bromide fluoresce more intensely when intercalated into double-stranded DNA than when bound to single-stranded DNA, RNA, or in solution (see, e.g., U.S. Pat. Nos. 5,994,056; 6,171,785; and/or 6,814,934). Similarly, actinomycin D fluoresces in the red portion of the UV/VIS spectrum when bound to single-stranded nucleic acids, and fluoresces in the green portion of the UV/VIS spectrum when bound to double-stranded nucleic acids. And in another example, the photoreactive psoralen 4-aminomethyl-4-5',8-trimethylpsoralen (AMT) has been reported to exhibit decreased absorption at long wavelengths and fluorescence upon intercalation into double-stranded DNA (Johnson et al. *Photochem. & Photobiol.*, 33:785-791 (1981). For example, U.S. Pat. No. 4,257,774 describes the direct binding of fluorescent intercalators to DNA (e.g., ethidium salts, daunomycin, mepacrine and acridine orange, 4',6-diamidino-α-phenylindole). Non-intercalating agents (e.g., minor groove binders as described herein such as Hoechst 33258, distamycin, netropsin) may also be suitable for use. For example, Hoechst 33258 (Searle, et al. *Nucl. Acids Res.* 18(13):3753-3762 (1990)) exhibits altered fluorescence with an increasing amount of target. Minor groove binders are described in more detail elsewhere herein.

Other DNA binding dyes are available to one of skill in the art and may be used alone or in combination with other agents and/or components of an assay system. Exemplary DNA binding dyes may include, for example, acridines (e.g., acridine orange, acriflavine), actinomycin D (Jain, et al. *J. Mol. Biol.* 68:21 (1972)), anthramycin, BOBO™-1, BOBO™-3, BO-PRO™-1, cbromomycin, DAPI (Kapuseinski, et al. *Nucl. Acids Res.* 6(112): 3519 (1979)), daunomycin, distamycin (e.g., distamycin D), dyes described in U.S. Pat. No. 7,387,887, ellipticine, ethidium salts (e.g., ethidium bromide), fluorcoumanin, fluorescent intercalators as described in U.S. Pat. No. 4,257,774, GelStar® (Cambrex Bio Science Rockland Inc., Rockland, Me.), Hoechst 33258 (Searle and Embrey, *Nucl. Acids Res.* 18:3753-3762 (1990)), Hoechst 33342, homidium, JO-PRO™-1, LIZ dyes, LO-PRO™-1, mepacrine, mithramycin, NED dyes, netropsin, 4',6-diamidino-α-phenylindole, proflavine, POPO™-1, POPO™-3, PO-PRO™-1, propidium iodide, ruthenium polypyridyls, S5, SYBR® Gold, SYBR® Green I (U.S. Pat. Nos. 5,436,134 and 5,658,751), SYBR® Green II, SYTOX® blue, SYTOX® green, SYTO® 43, SYTO® 44, SYTO® 45, SYTOX® Blue, TO-PRO®-1, SYTO® 11, SYTO® 13, SYTO® 15, SYTO® 16, SYTO® 20, SYTO® 23, thiazole orange (Aldrich Chemical Co., Milwaukee, Wis.), TOTO™-3, YO-PRO®-1, and YOYO®-3 (Molecular Probes, Inc., Eugene, Oreg.), among others. SYBR® Green I (see, e.g., U.S. Pat. Nos. 5,436,134; 5,658,751; and/or 6,569,927), for example, has been used to monitor a PCR reactions. Other DNA binding dyes may also be suitable as would be understood by one of skill in the art.

For use as described herein, one or more detectable labels and/or quenching agents may be attached to one or more primers and/or probes (e.g., detectable label). The detectable label may emit a signal when free or when bound to one of the target nucleic acids. The detectable label may also emit a signal when in proximity to another detectable label. Detectable labels may also be used with quencher molecules such that the signal is only detectable when not in sufficiently close proximity to the quencher molecule. For instance, in some embodiments, the assay system may cause the detectable label to be liberated from the quenching molecule. Any of several detectable labels may be used to label the primers and probes used in the methods described herein. As mentioned above, in some embodiments the detectable label may be attached to a probe, which may be incorporated into a primer, or may otherwise bind to amplified target nucleic acid (e.g., a detectable nucleic acid binding agent such as an intercalating or non-intercalating dye). When using more than one detectable label, each should differ in their spectral properties such that the labels may be distinguished from each other, or such that together the detectable labels emit a signal that is not emitted by either detectable label alone. Exemplary detectable labels include, for instance, a fluorescent dye or fluorphore (e.g., a chemical group that can be excited by light to emit fluorescence or phosphorescence), "acceptor dyes" capable of quenching a fluorescent signal from a fluorescent donor dye, and the like. Suitable detectable labels may include, for example, fluoresceins (e.g., 5-carboxy-2,7-dichlorofluorescein; 5-Carboxyfluorescein (5-FAM); 5-Hydroxy Tryptamine (5-HAT); 6-JOE; 6-carboxyfluorescein (6-FAM); FITC; 6-carboxy-1,4-dichloro-2',7'-dichloro-fluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa Fluor® fluorophores (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxycoumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (Fi-CRhR), fluorescent proteins (e.g., green fluorescent protein (e.g., GFP. EGFP), blue fluorescent protein (e.g., BFP, EBFP, EBFP2, Azurite, mKalamal), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker® and LysoSensor™ (e.g., LysoTracker® Blue DND-22, LysoTracker® Blue-White DPX, LysoTracker® Yellow HCK-123, LysoTracker® Green DND-26, LysoTracker® Red DND-99, LysoSensor™ Blue DND-167, LysoSensor™ Green DND-189, LysoSensor™ Green DND-153, LysoSensor™ Yellow/Blue DND-160, LysoSensor™ Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethylrhodamine), Tetramethylrhodamine (TRITC), WT), Texas Red, Texas Red-X, VIC and other labels described in, e.g., U.S. Patent Application Publication No. 2009/0197254 (incorporated herein by reference in its entirety), among others as would be known to those of skill in the art. Other detectable labels may also be used (see, e.g., U.S. Patent Application Publication No. 2009/0197254 (incorporated herein by reference in its entirety)), as would be known to those of skill in the art. Any of these systems and detectable labels, as well as many others, may be used to detect amplified target nucleic acids.

Some detectable labels may be sequence-based (also referred to herein as "locus-specific detectable label"), for example 5'-nuclease probes. Such probes may comprise one or more detectable labels. Various detectable labels are known in the art, for example (TaqMan® probes described herein (See also U.S. Pat. No. 5,538,848 (incorporated herein by reference in its entirety)) various stem-loop molecular beacons (See, e.g., U.S. Pat. Nos. 6,103,476 and 5,925,517 and Tyagi and Kramer, *Nature Biotechnology* 14:303-308 (1996)), stemless or linear beacons (See, e.g., PCT Publication No. WO 99/21881; U.S. Pat. No. 6,485, 901), PNA Molecular Beacons™ (See, e.g., U.S. Pat. Nos. 6,355,421 and 6,593,091), linear PNA beacons (See, e.g., Kubista et al., SPIE 4264:53-58 (2001)), non-FRET probes (See, e.g., U.S. Pat. No. 6,150,097), Sunrise®/Amplifluor® probes (U.S. Pat. No. 6,548,250), stem-loop and duplex Scorpions™ probes (Solinas et al., *Nucleic Acids Research* 29:E96 (2001) and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes (Svanvik, et al. *Anal Biochem* 281:26-35 (2001)), self-assembled nanoparticle probes, ferrocene-modified probes described, for example, in U.S. Pat. No. 6,485,901; Mhlanga et al., *Methods* 25:463-471 (2001); Whitcombe et al., *Nature Biotechnology.* 17:804-807 (1999); Isacsson et al., *Molecular Cell Probes.* 14:321-328 (2000); Svanvik et al., *Anal Biochem.* 281:26-35 (2000); Wolffs et al., *Biotechniques* 766:769-771 (2001); Tsourkas et al., *Nucleic Acids Research.* 30:4208-4215 (2002); Riccelli et al., *Nucleic Acids Research* 30:4088-4093 (2002); Zhang et al., *Acta Biochimica et Biophysica Sinica (Shanghai).* 34:329-332 (2002); Maxwell et al., *J. Am. Chem. Soc.* 124:9606-9612 (2002); Broude et al., *Trends Biotechnol.* 20:249-56 (2002); Huang et al., *Chem Res. Toxicol.* 15:118-126 (2002); and Yu et al., *J. Am. Chem. Soc.* 14:11155-11161 (2001); QuantiProbes® (www.qiagen.com), HyBeacons® (French, et al. *Mol. Cell. Probes* 15:363-374 (2001)), displacement probes (Li, et al. *Nucl. Acids Res.* 30:e5 (2002)), HybProbes (Cardullo, et al. *Proc. Natl. Acad. Sci. USA* 85:8790-8794 (1988)), MGB Alert (www.nanogen.com), Q-PNA (Fiandaca, et al. *Genome Res.* 11:609-611 (2001)), Plexor® (www.Promega.com), LUX™ primers (Nazarenko, et al. *Nucleic Acids Res.* 30:e37 (2002)), DzyNA primers (Todd, et al. *Clin. Chem.* 46:625-630 (2000)). Detectable labels may also comprise non-detectable quencher moieties that quench the fluorescence of the detectable label, inlcuding, for example, black hole quenchers (Biosearch), Iowa Black® quenchers (IDT), QSY quencher (Molecular Probes), and Dabsyl and Dabcyl sulfonate/carboxylate Quenchers (Epoch). Detectable labels may also comprise two probes, wherein for example a fluorophore is on one probe, and a quencher is on the other, wherein hybridization of the two probes together on a target quenches the signal, or wherein hybridization on a target alters the signal signature via a change in fluorescence. Exemplary systems may also include FRET, salicylate/DTPA ligand systems (see, e.g., Oser et al. *Angew. Chem. Int. Engl.* 29(10):1167 (1990)), displacement hybridization, homologous probes, and/or assays described in European Patent No. EP 070685 and/or U.S. Pat. No. 6,238,927. Detectable labels can also comprise sulfonate derivatives of fluorescein dyes with $SO_3$ instead of the carboxylate group, phosphoramidite forms of fluorescein, phosphoramidite forms of Cy5 (available for example from Amersham). All references cited above are hereby incorporated herein by reference in their entirety.

The compositions and methods described herein may be useful for detecting and/or quantifying a variety of target nucleic acids from a test sample. A target nucleic acid is any nucleic acid for which an assay system is designed to identify or detect as present (or not), and/or quantify in a test sample. Such nucleic acids may include, for example, those of infectious agents (e.g., virus, bacteria, parasite, and the like), a disease process such as cancer, diabetes, or the like, or to measure an immune response. Exemplary "test samples" include various types of samples, such as biological samples. Exemplary biological samples include, for instance, a bodily fluid (e.g., blood, saliva, spinal fluid), a tissue sample, a food (e.g., meat) or beverage (e.g., milk) product, or the like. Expressed nucleic acids may include, for example, genes for which expression (or lack thereof) is associated with medical conditions such as infectious disease (e.g., bacterial, viral, fungal, protozoal infections) or cancer. The methods described herein may also be used to detect contaminants (e.g., bacteria, virus, fungus, and/or protozoan) in pharmaceutical, food, or beverage products. The methods described herein may be also be used to detect rare alleles in the presence of wild type alleles (e.g., one mutant allele in the presence of $10^6$-$10^9$ wild type alleles). The methods are useful to, for example, detect minimal residual disease (e.g., rare remaining cancer cells during remission, especially mutations in the p53 gene or other tumor suppressor genes previously identified within the tumors), and/or measure mutation load (e.g., the frequency of specific somatic mutations present in normal tissues, such as blood or urine).

Kits for performing the methods described herein are also provided. As used herein, the term "kit" refers to a packaged set of related components, typically one or more compounds or compositions. The kit may comprise a pair of oligonucleotides for polymerizing and/or amplifying at least one target nucleic acid from a sample, one or more detergents, a nucleic acid polymerase), a dual hot start reaction mixture, and/or corresponding one or more probes labeled with a detectable label. The kit may also include samples containing pre-defined target nucleic acids to be used in control reactions. The kit may also optionally include stock solutions, buffers, enzymes, detectable labels or reagents required for detection, tubes, membranes, and the like that may be used to complete the amplification reaction. In some embodiments, multiple primer sets are included. In one embodiment, the kit may include one or more of, for example, a buffer (e.g., Tris), one or more salts (e.g., KCl), glycerol, dNTPs (dA, dT, dG, dC, dU), recombinant BSA (bovine serum albumin), a dye (e.g., ROX passive reference dye), one or more detergents, polyethylene glycol (PEG), polyvinyl pyrrolidone (PVP), and/or gelatin (e.g., fish or bovine source). Other embodiments of particular systems and kits are also contemplated which would be understood by one of skill in the art.

EXAMPLES

Commercially available master mixes with different hot start mechanisms were combined and tested to demonstrate the effectiveness of a dual hot start reaction mixture. The experimental setup is outlined in Table 1:

TABLE 1

| Experimental Setup | Reaction Conditions |
| --- | --- |
| Set 1 | Fast SYBR ® Green Master Mix (alone) |
|  | Fast SYBR ® Green Master Mix + Platinum ® SYBR ® Green qPCR SuperMix (1:1 ratio) |
| Set 2 | Fast SYBR ® Green Master Mix (alone) |
|  | Fast SYBR ® Green Master Mix + Platinum ® Taq Antibody |
| Set 3 | Power SYBR ® Green PCR Master Mix (alone) |
|  | Power SYBR ® Green PCR Master Mix + Platinum ® Taq Antibody |

All reactions were performed with 2 ng Universal Human Reference (UHR) (Agilent Technologies, Santa Clara, Calif.) cDNA and 200 nM primers (24 targets tested) in a final volume of 10 μl. Four replicates were performed for each reaction. Amplification was performed on a ViiA™ 7 Real-Time PCR System (Life Technologies Corp., Carlsbad, Calif.) after incubation at room temperature for either 0 hours or 24 hours (T0 and T24, respectively). After incubation at room temperature, amplification was carried out according to the manufacturer's instructions. Briefly, thermal cycling conditions were set as follows:

| Standard Cycling Mode (Primer $T_m$ ≥ 60° C.) | | | |
| --- | --- | --- | --- |
| Step | Temperature | Duration | Cycles |
| UDG Activation | 50° C. | 2 min | Hold |
| AmpliTaq ®DNA Polymerase, UP Activation | 95° C. | 2 min | Hold |
| Denature | 95° C. | 15 sec | 40 |
| Anneal/Extend | 60° C. | 1 min | |

| Standard Cycling Mode (Primer $T_m$ ≥ 60° C.) | | | |
| --- | --- | --- | --- |
| Step | Temperature | Duration | Cycles |
| UDG Activation | 50° C. | 2 min | Hold |
| AmpliTaq ®DNA Polymerase, UP Activation | 95° C. | 2 min | Hold |
| Denature | 95° C. | 15 sec | 40 |
| Anneal | 55-60° C.* | 15 sec | |
| Extend | 72° C. | 1 min | |

In some instances, Power SYBR® Green qPCR SuperMix or Fast SYBR® Green Master Mix was incubated overnight (16-20 hours) with Platinum® Taq Antibody. All components tested are commercially available and were purchased from Life Technologies Corporation.

In FIGS. 1A-1D, the target nucleic acid was amplified with 24 primer sets using either a single or a dual hot start reaction mixture. The single hot start reaction mixtures used either Fast SYBR® Green Master Mix alone ("square" line) or Platinum® SYBR® Green qPCR SuperMix alone ("cross" line). The dual hot start reaction mixture used a 1:1 combination of Fast SYBR® Green Master Mix and Platinum® SYBR® Green qPCR SuperMix ("triangle" line). All three reaction sets were incubated at room temperature for either 0 hours ("T0") or 24 hours ("T24") before amplification. In many of the assays, the combination of the two different hot start mechanisms resulted in a decrease in the formation of non-specific products (see, FIGS. 1A (T0, cDNA), 1B (T0, non-specific product ("NTC")), 1C (T24, cDNA), and 1D (T24, NTC)).

In FIGS. 2A-1 through 2L-2, individual amplicons were selected and analyzed by melt curve analysis. FIG. 2A-1 through 2C-2 demonstrates that the dual hot start reaction mixture gives a 4-fold reduction in the formation of non-specific products when compared to the single hot start reaction mixture (Fast SYBR® Green Master Mix) and a 2-fold reduction when compared to the other single hot start reaction mixture (Platinum® SYBR® Green qPCR SuperMix) after 0 hours at room temperature. FIG. 2D-1 through 2F-2 demonstrates that the dual hot start reaction mixture gives a 2-fold reduction in the formation of non-specific products when compared to each of the single hot start reaction mixtures after 24 hour pre-incubation at room temperature. FIGS. 2G-1 through 2I-2 and 2J-1 through 2L-2 show that the dual hot start reaction mixture gives at least at 50% reduction in non-specific products at 0 hours pre-incubation at room temperature (FIG. 2G-1 through 2I-2) and a 100% reduction in non-specific products after 24 hours pre-incubation at room temperature (FIG. 2J-1 through 2L-2). FIG. 2M compares the mean Ct and the ΔCt analysis of amplification reactions of the single and dual hot start reaction mixtures effect on reduction of non-specific product formation. FIG. 2N shows a comparison of the melt curve analyses of the single and dual hot start reaction mixtures demonstrating that the dual hot start reaction mixture significantly reduces the formation of non-specific products at both 0 and 24 hours pre-incubation at room temperature (as shown by a reduction in the NTC ARn signal).

In FIGS. 3A-3D, the target nucleic acid was amplified with 24 primer sets using either a single or a dual hot start reaction mixture. The single hot start reaction mixtures used either Fast SYBR® Green Master Mix alone ("diamond" line) or in combination with Platinum® Taq Antibody ("cross" line). Both reaction sets were incubated at room temperature for either 0 hours ("T0") or 24 hours ("T24") before amplification. In many of the assays, the combination of the two different hot start mechanisms resulted in a decrease in the formation of non-specific products (see, FIGS. 3A (T0, cDNA), 3B (T0, non-specific product ("NTC")), 3C (T24, cDNA), and 3D (T24, NTC)).

Figures 1, 2A:
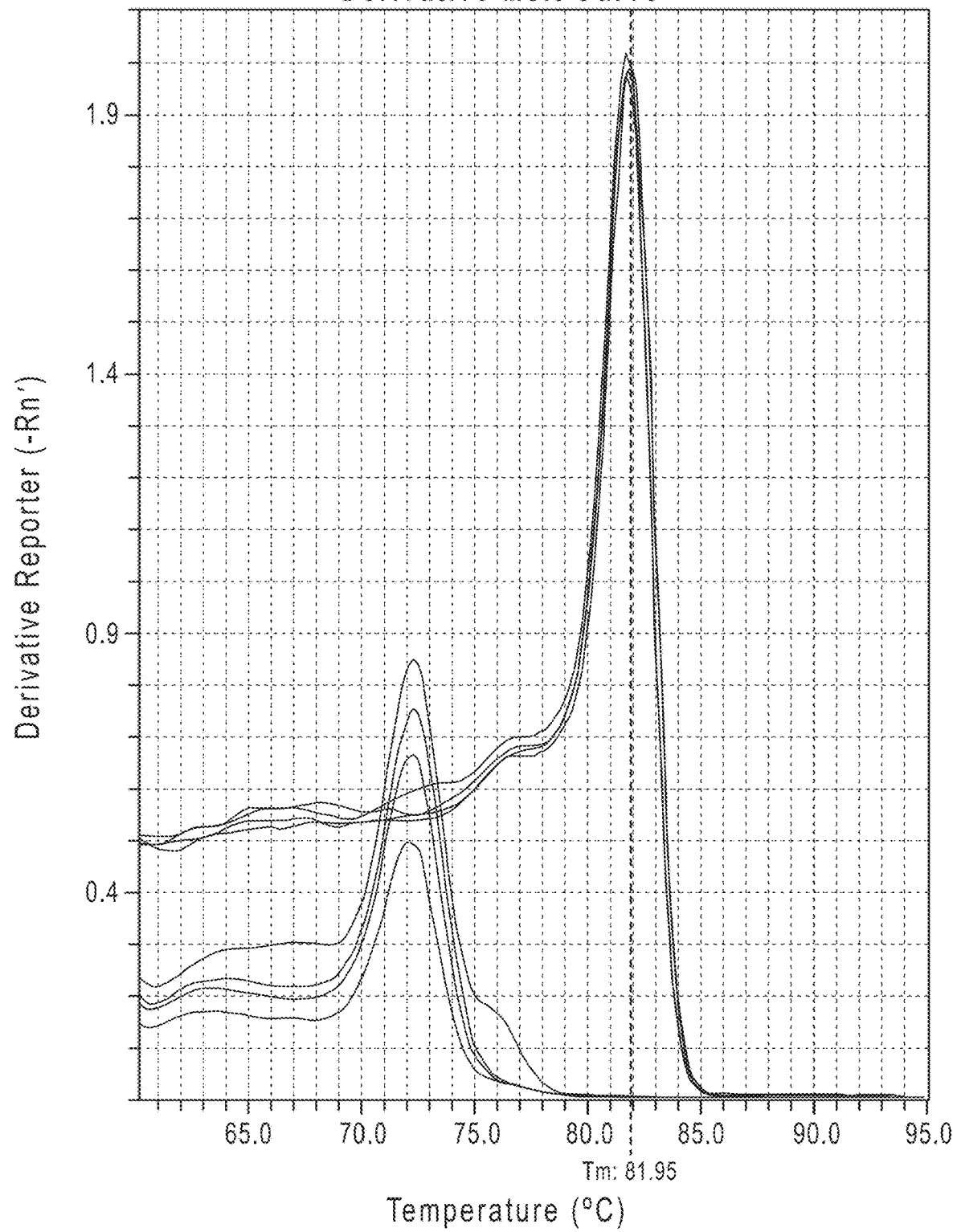
Figures 2, 2A:
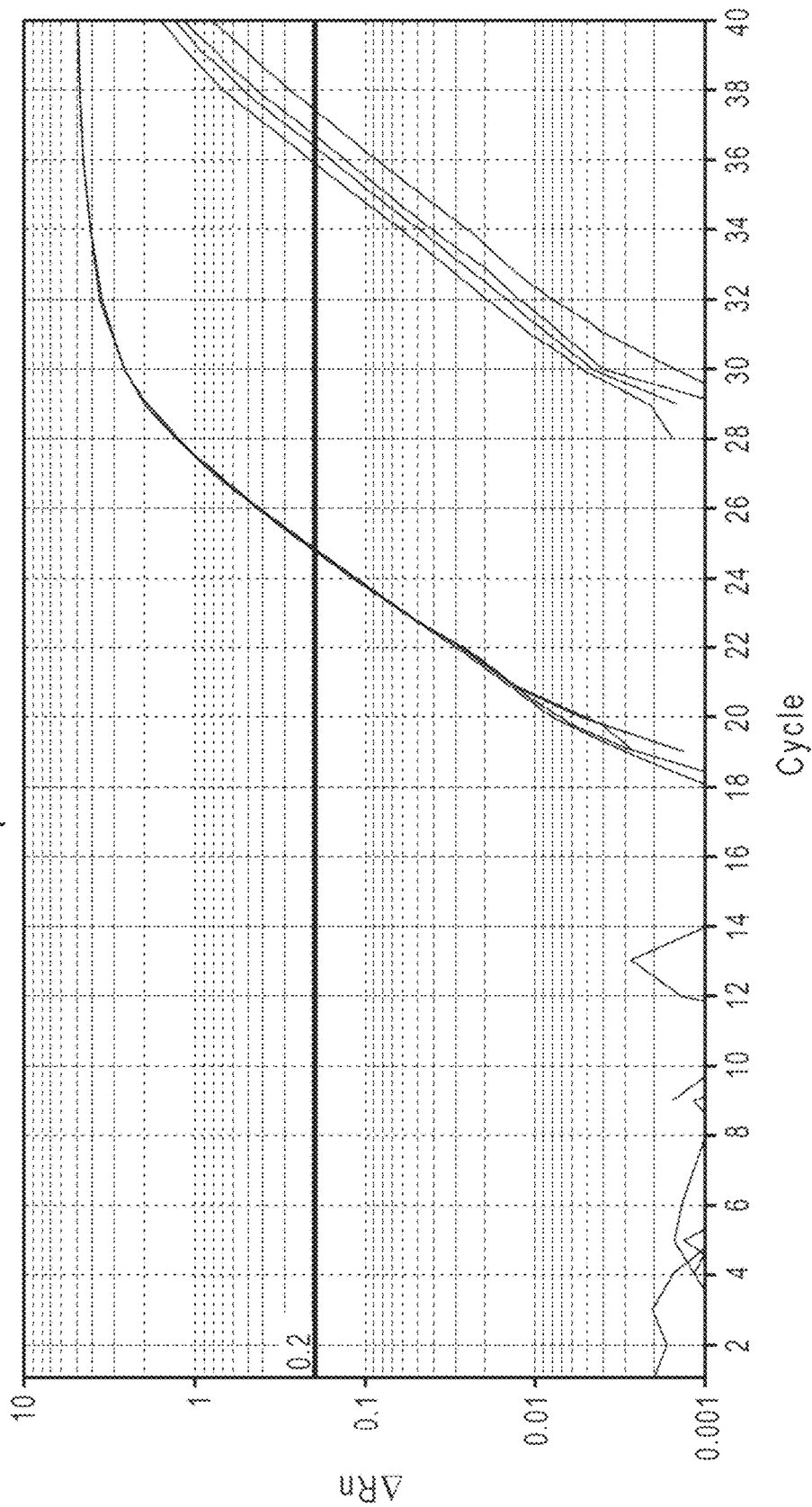
Figures 1, 2B:
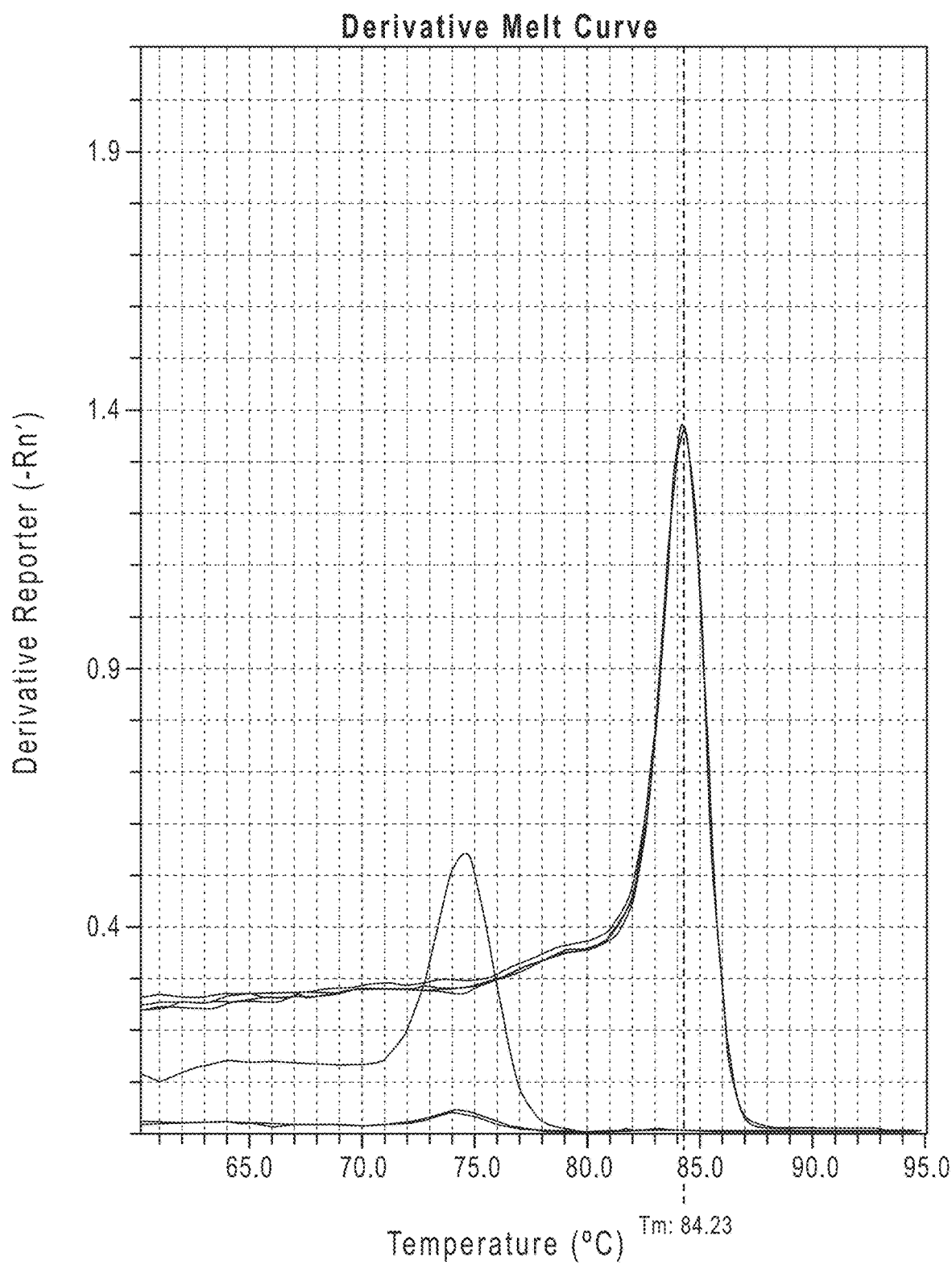
Figures 2, 2B:
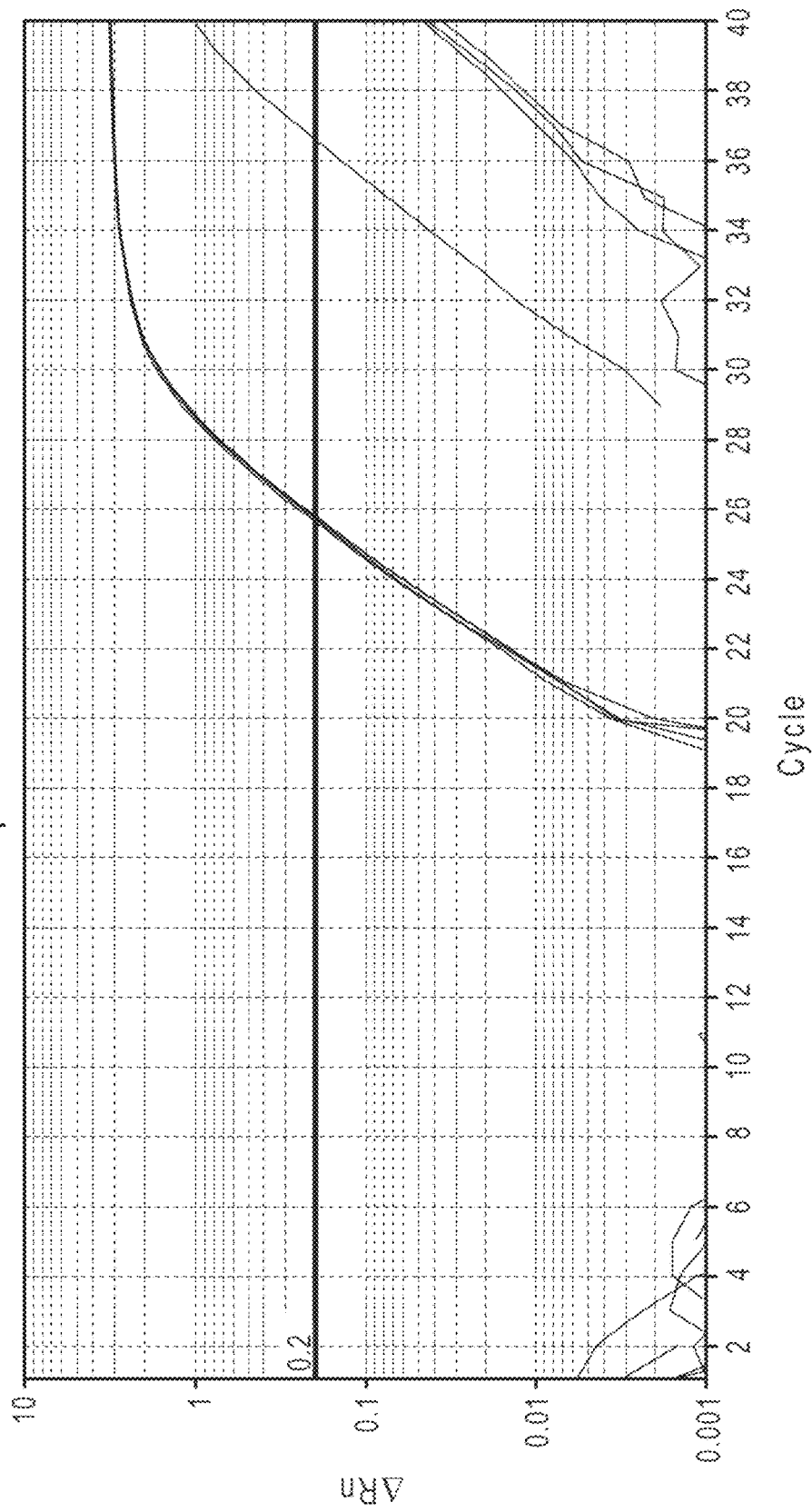
Figures 1, 2C:
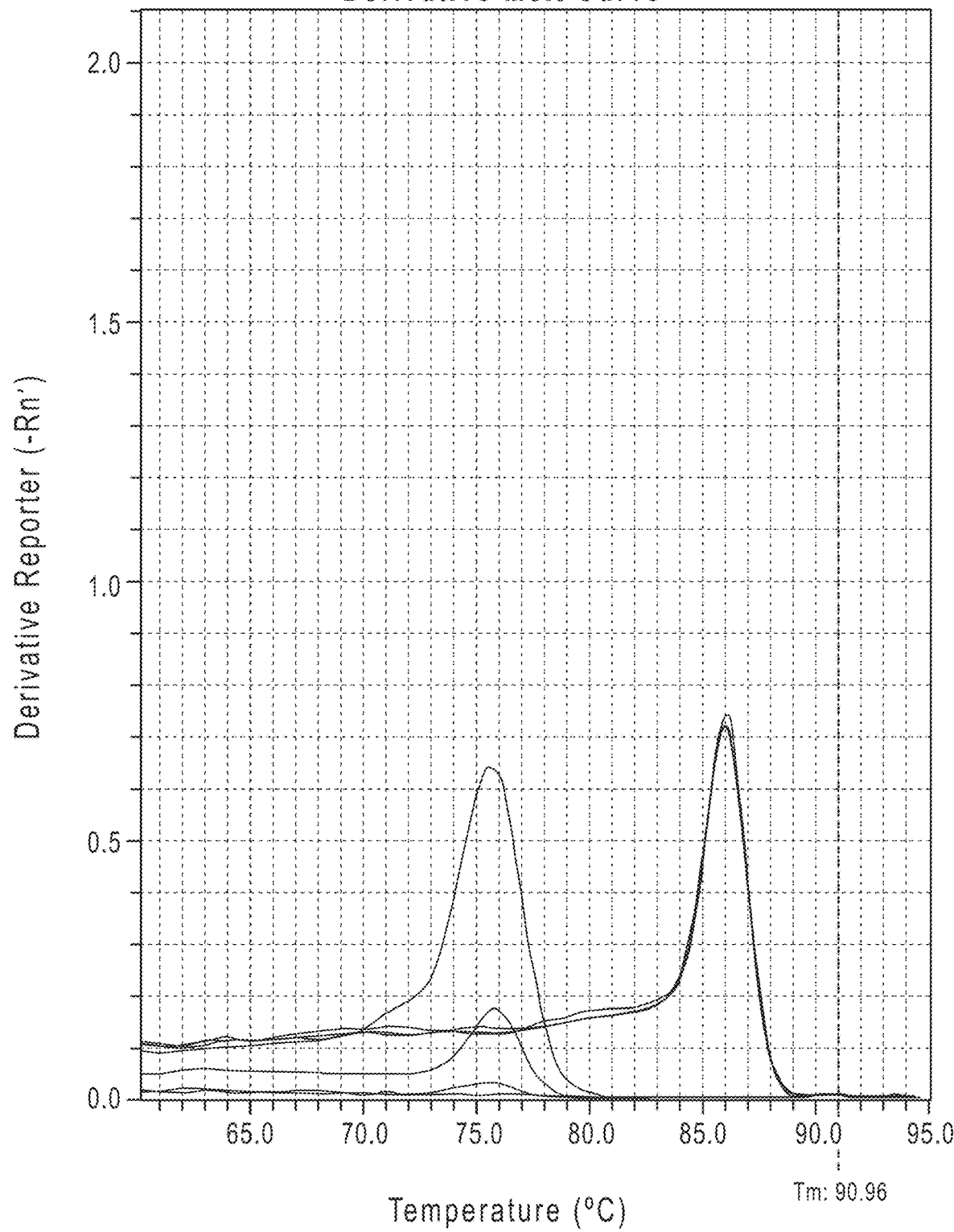
Figures 2, 2C:
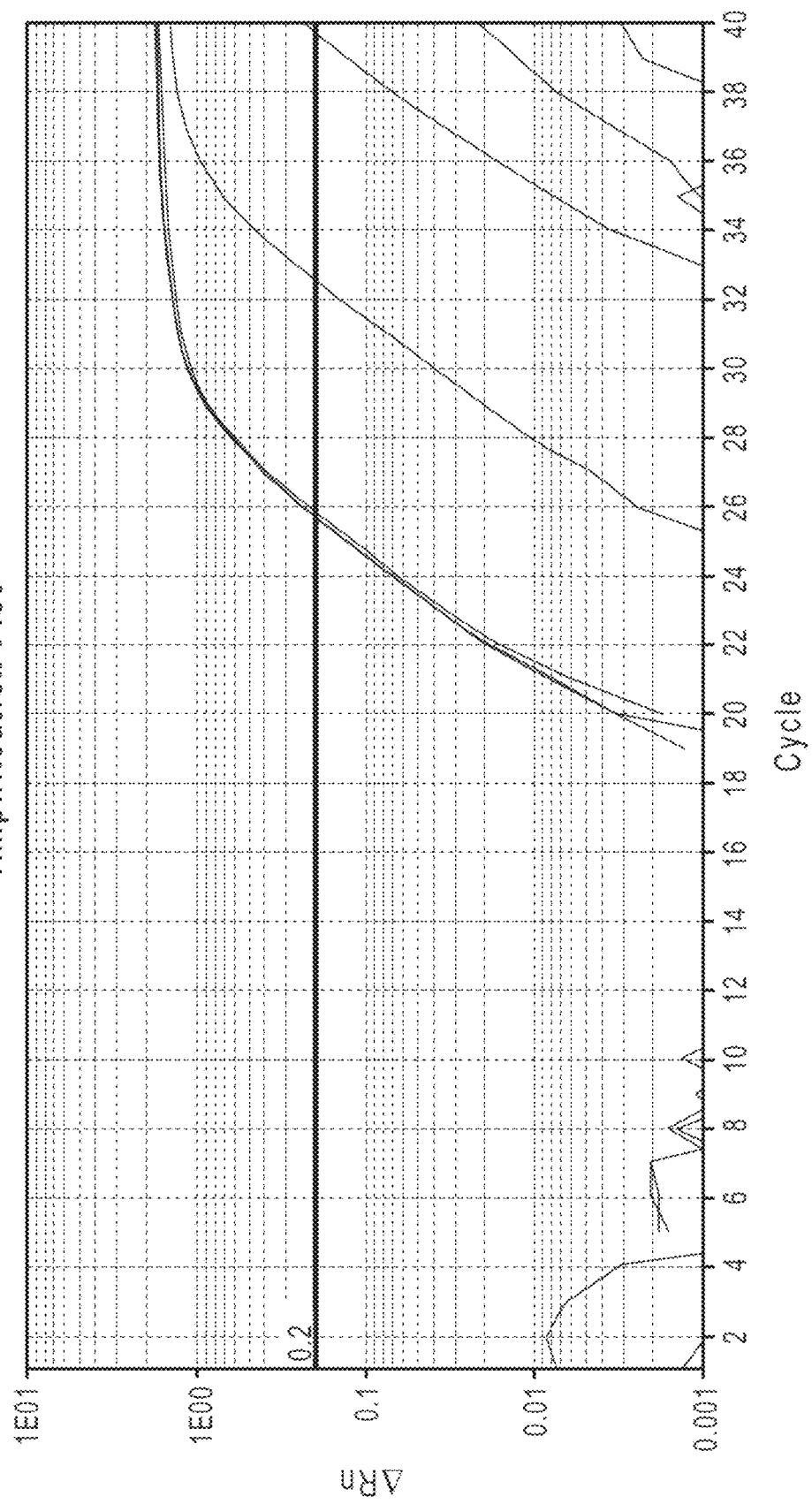
Figures 1, 2D:
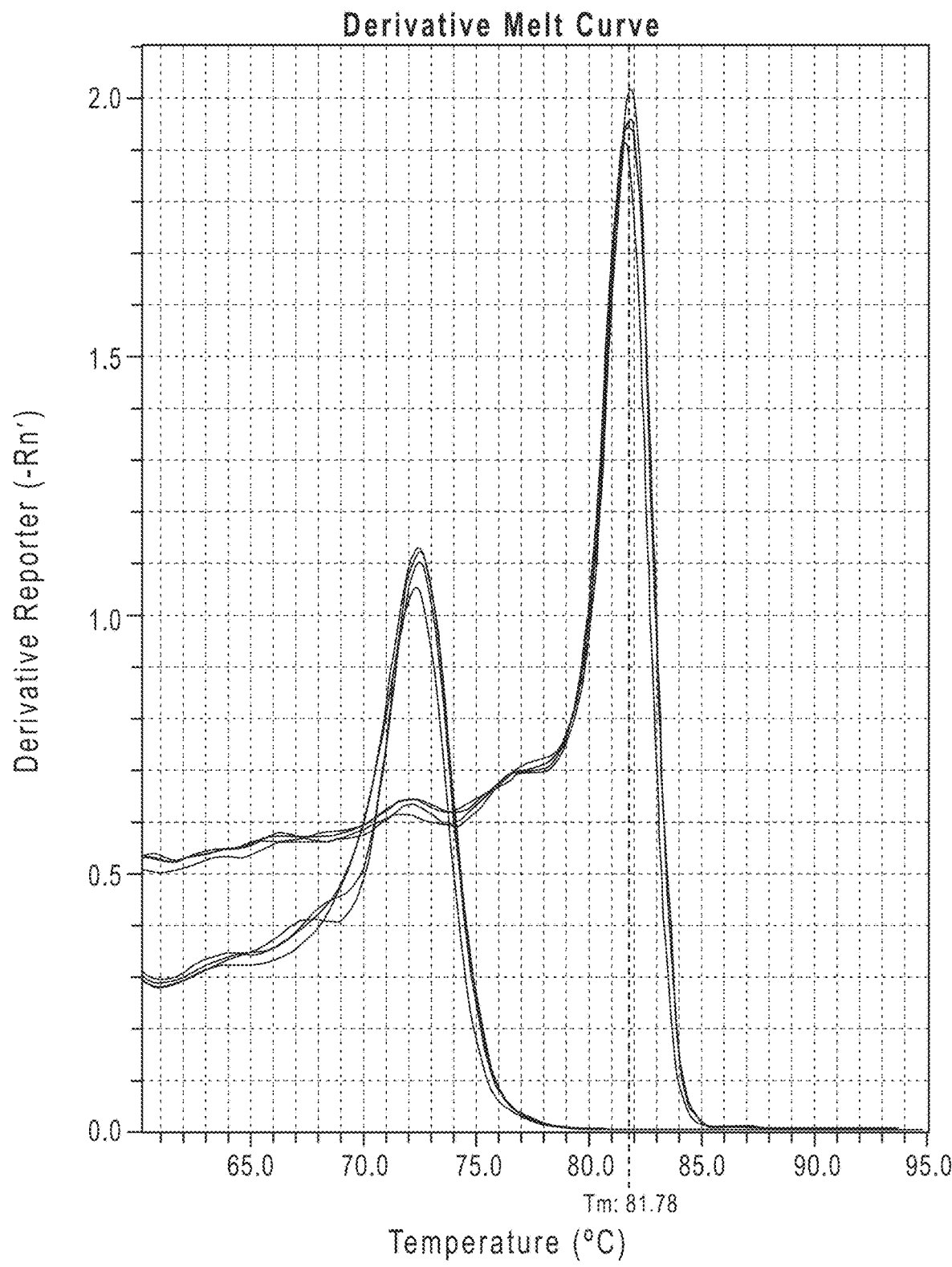
Figures 2, 2D:
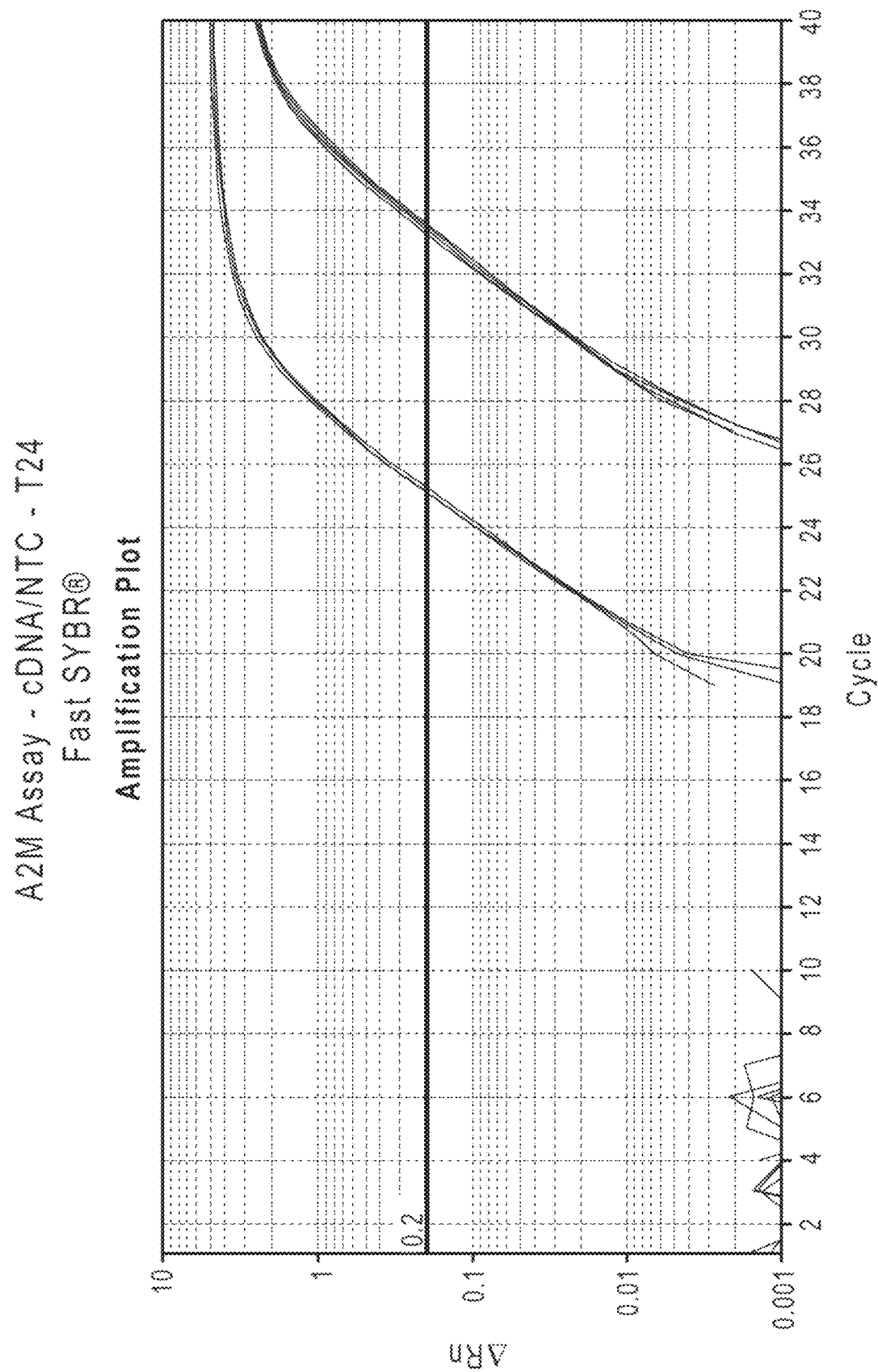
Figures 1, 2E:
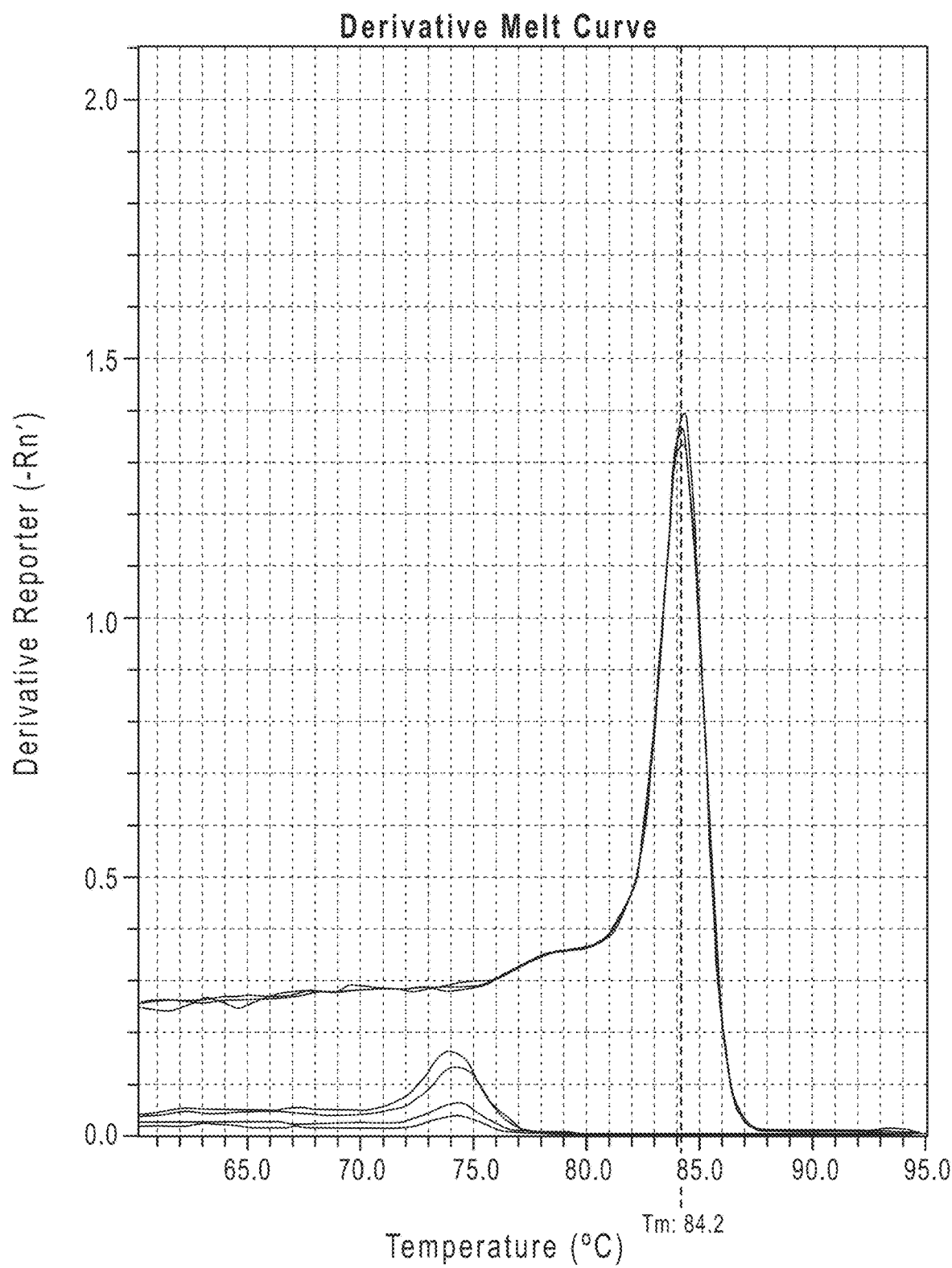
Figures 2, 2E:
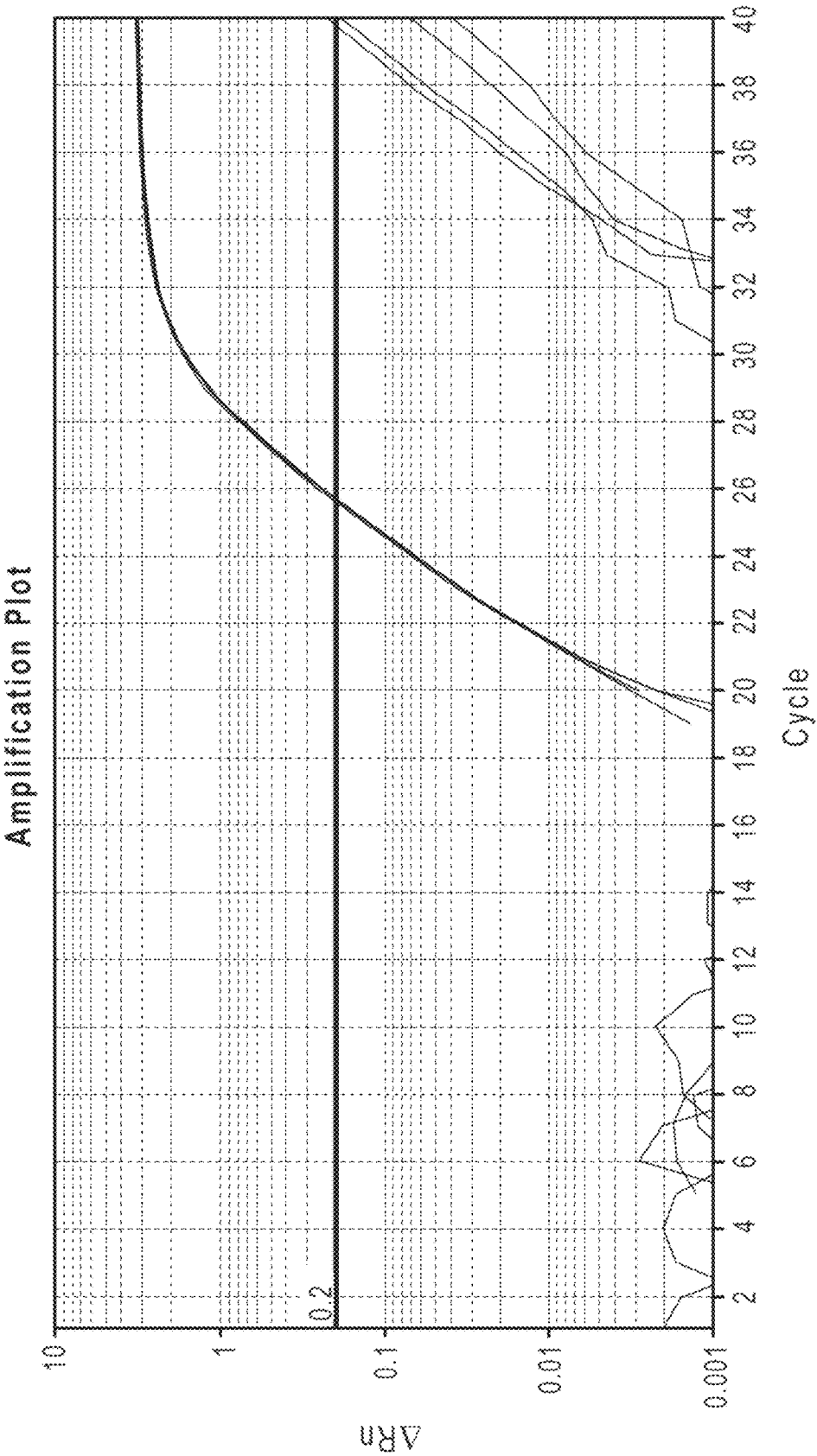
Figures 1, 2F:
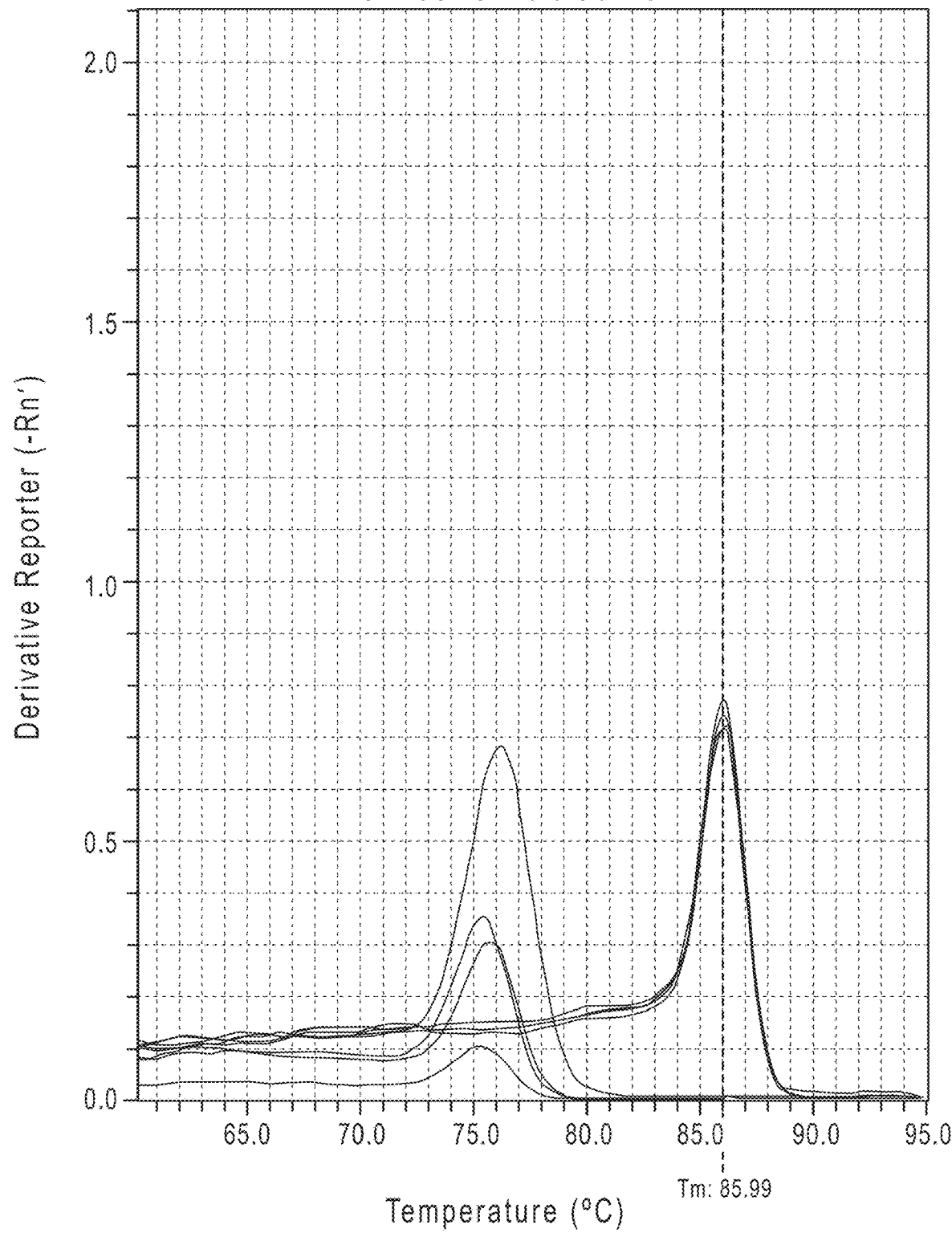
Figures 2, 2F:
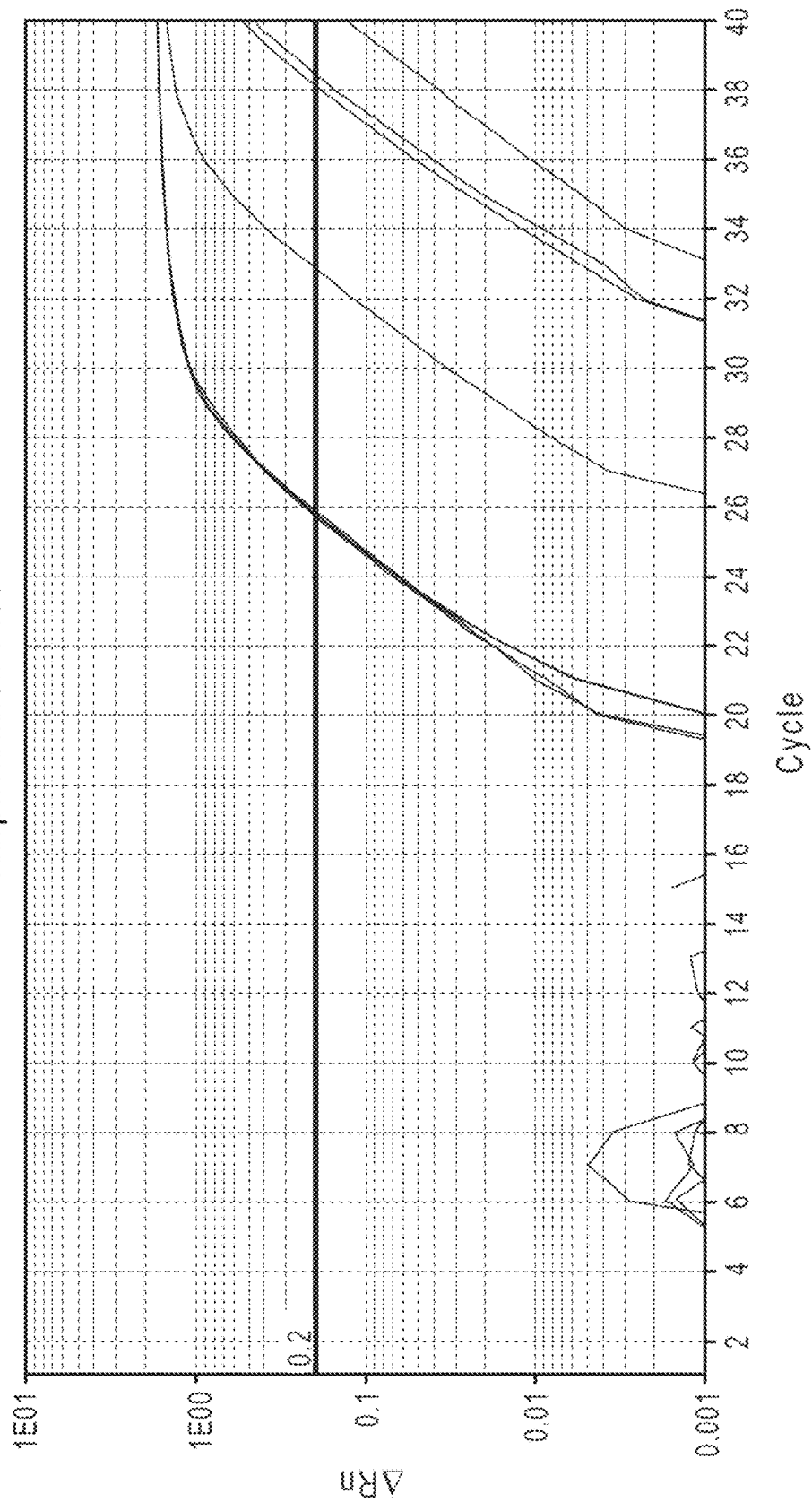
Figures 1, 2G:
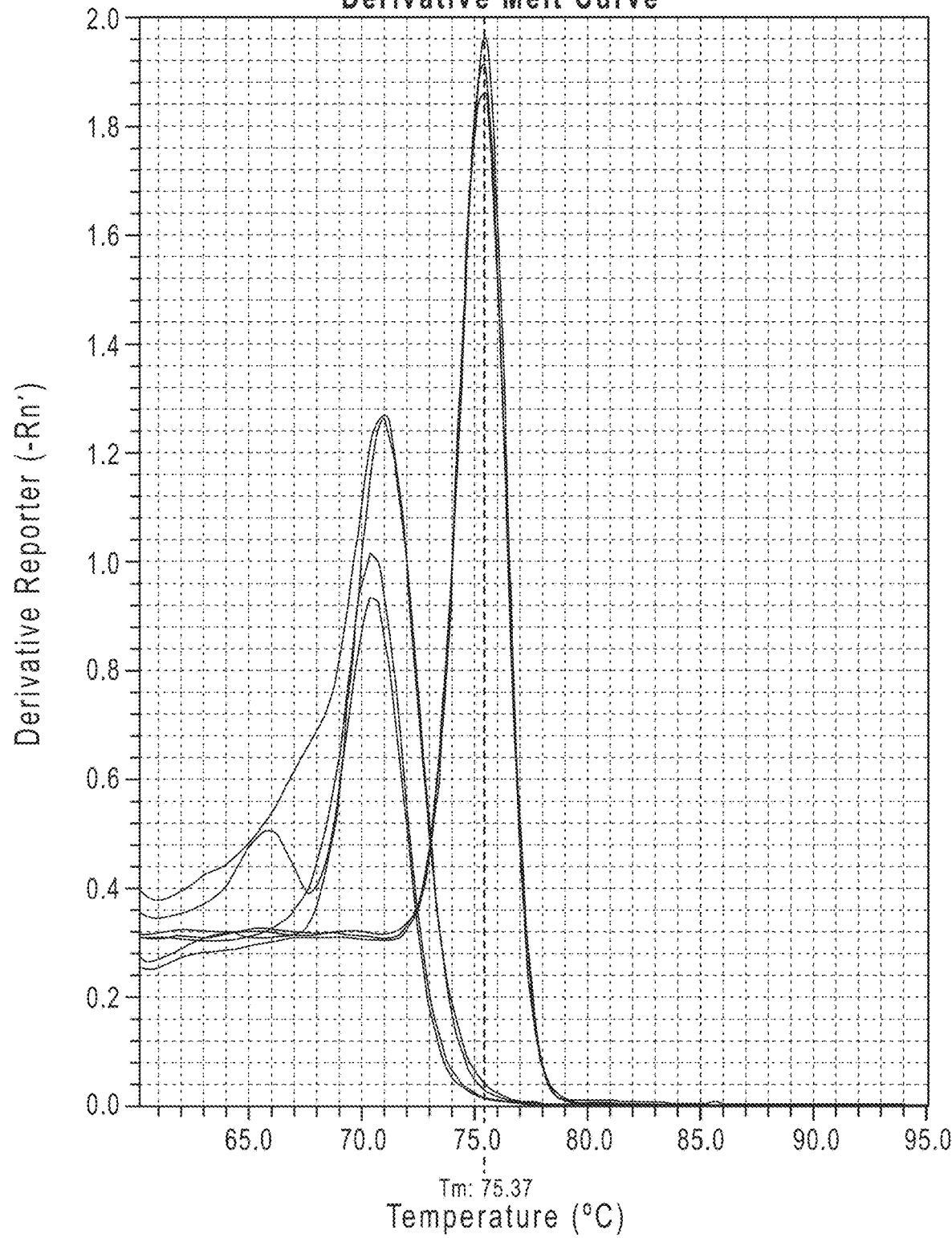
Figures 2, 2G:
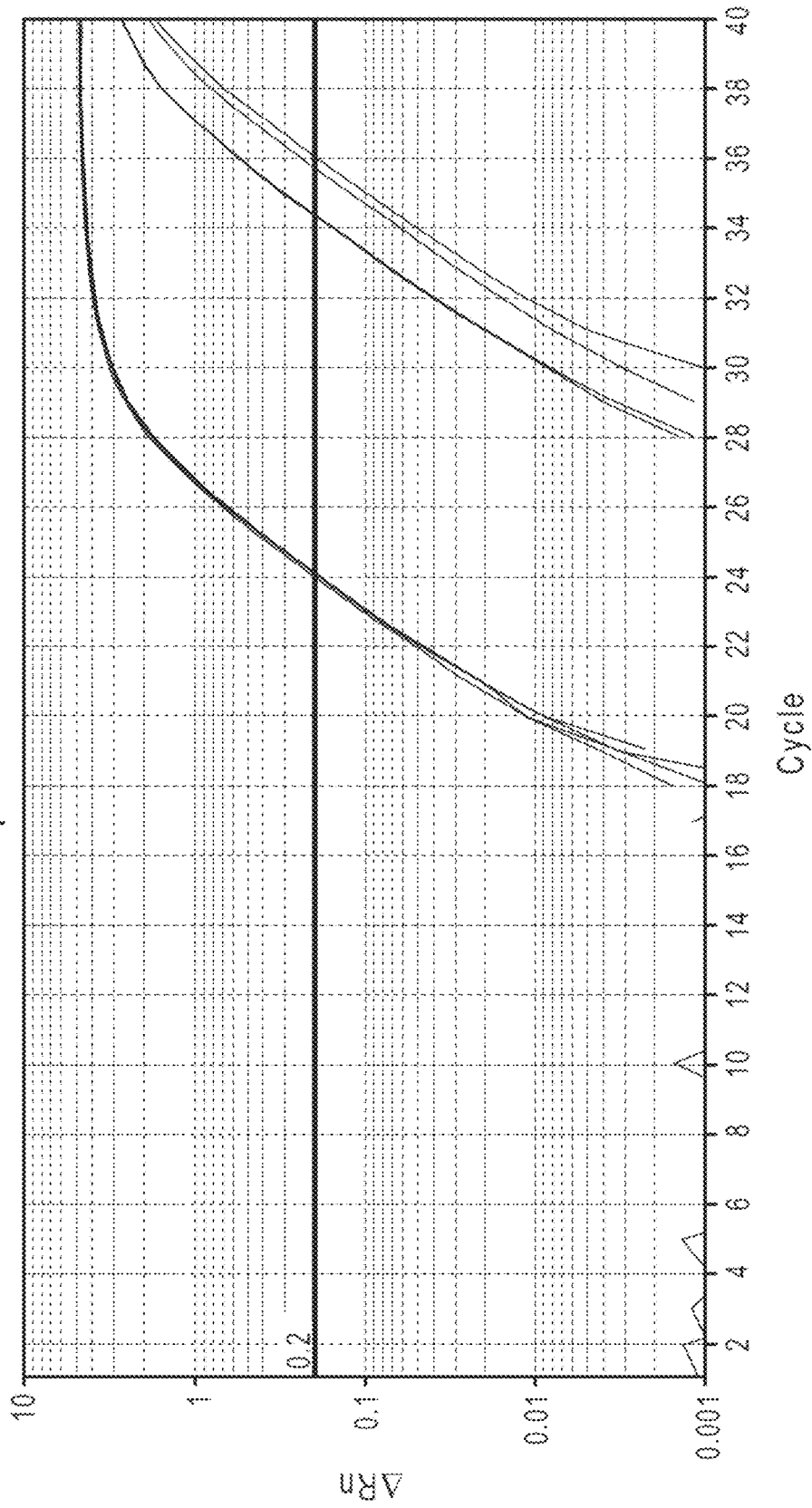
Figures 1, 2H:
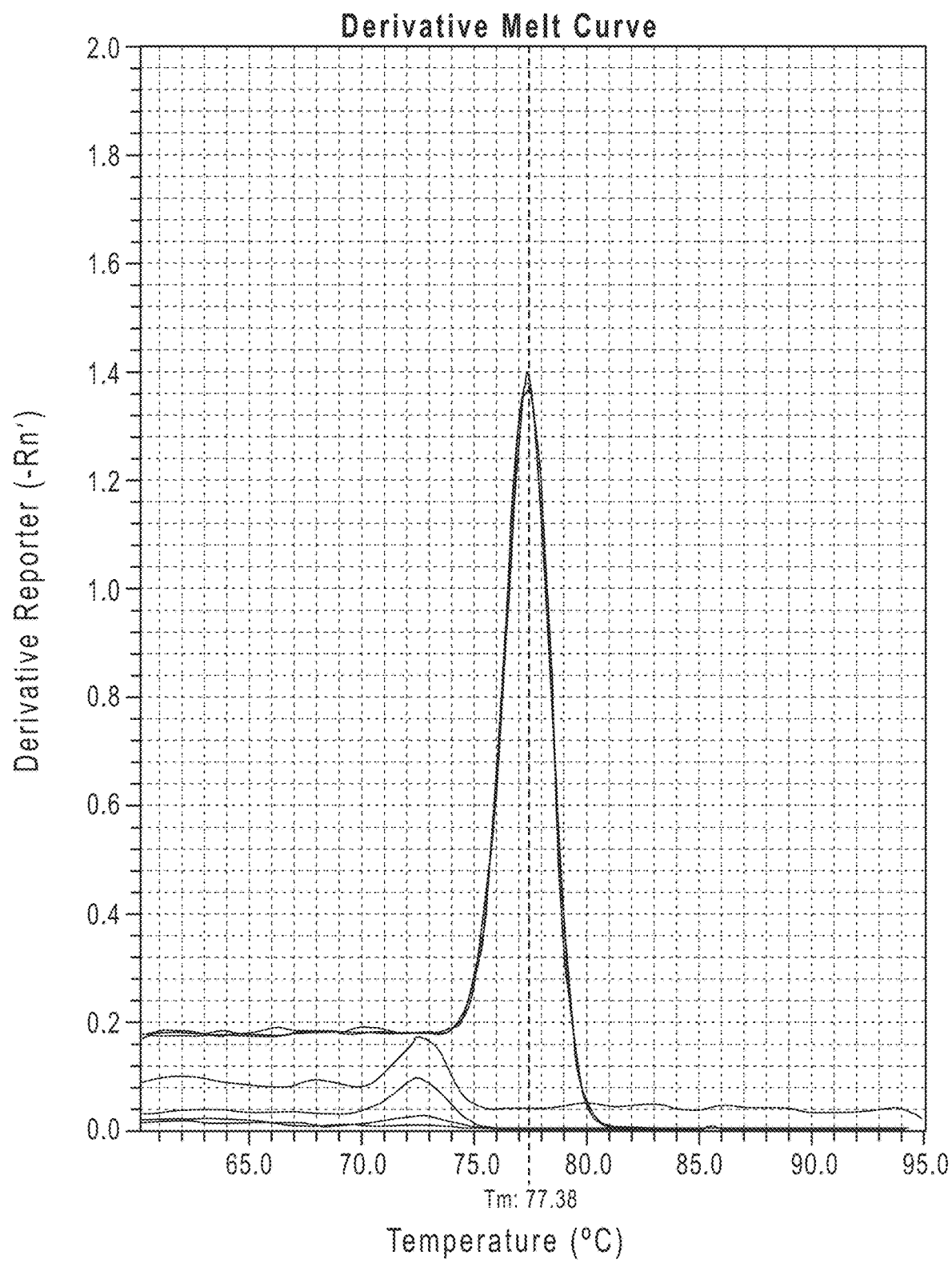
Figures 2, 2H:
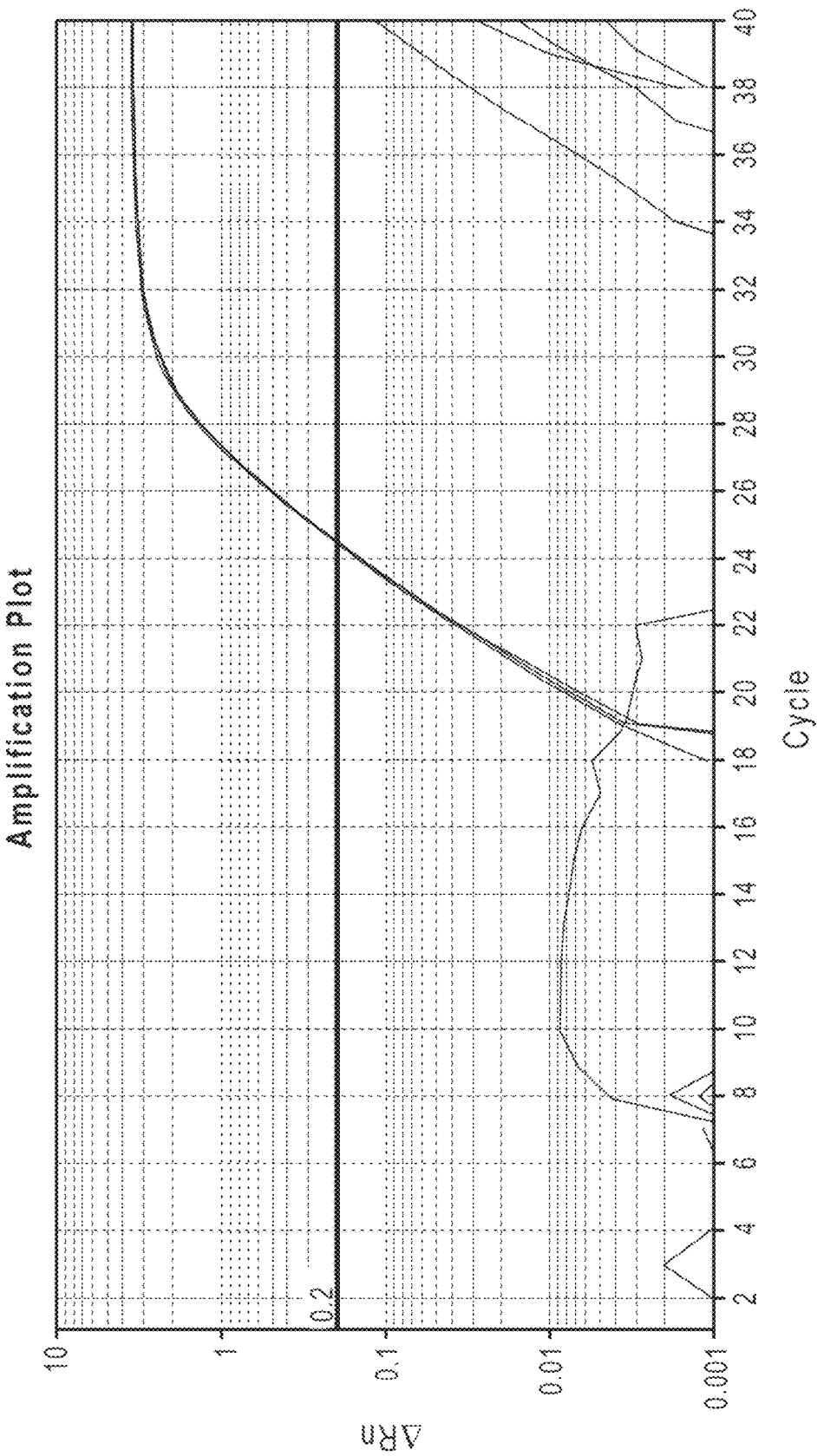
Figures 1, 2I:
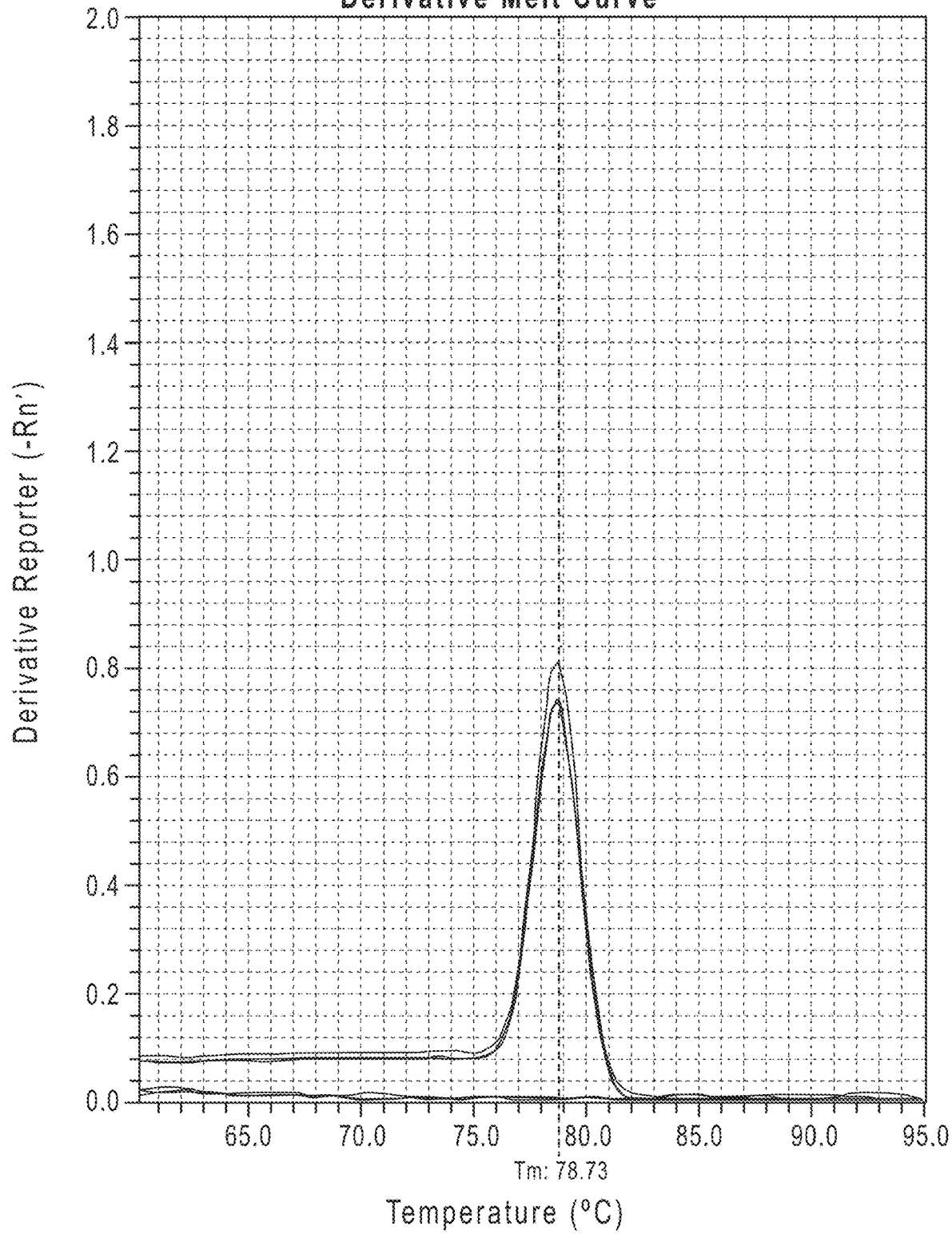
Figures 2, 2I:
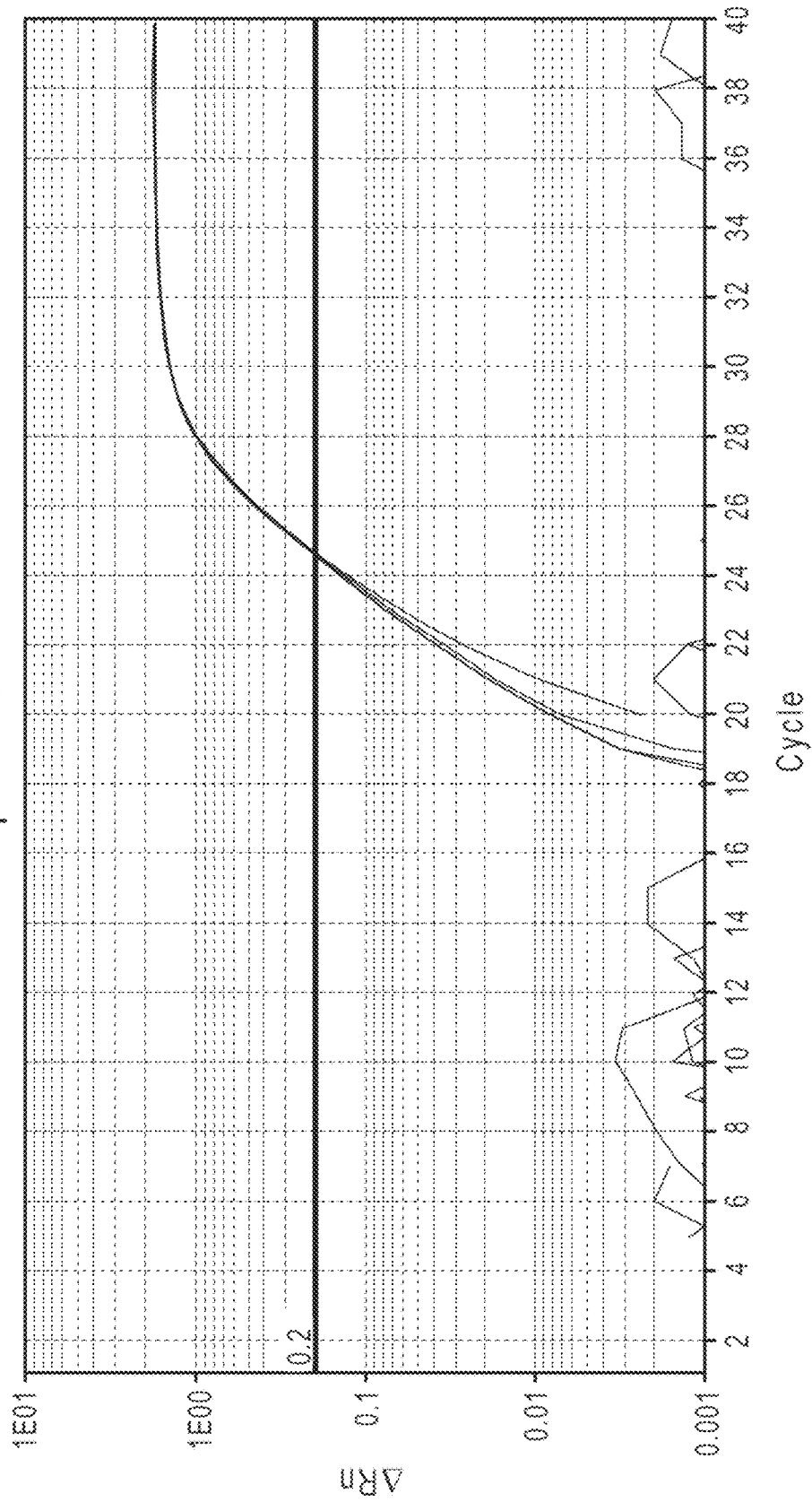
Figures 1, 2J:
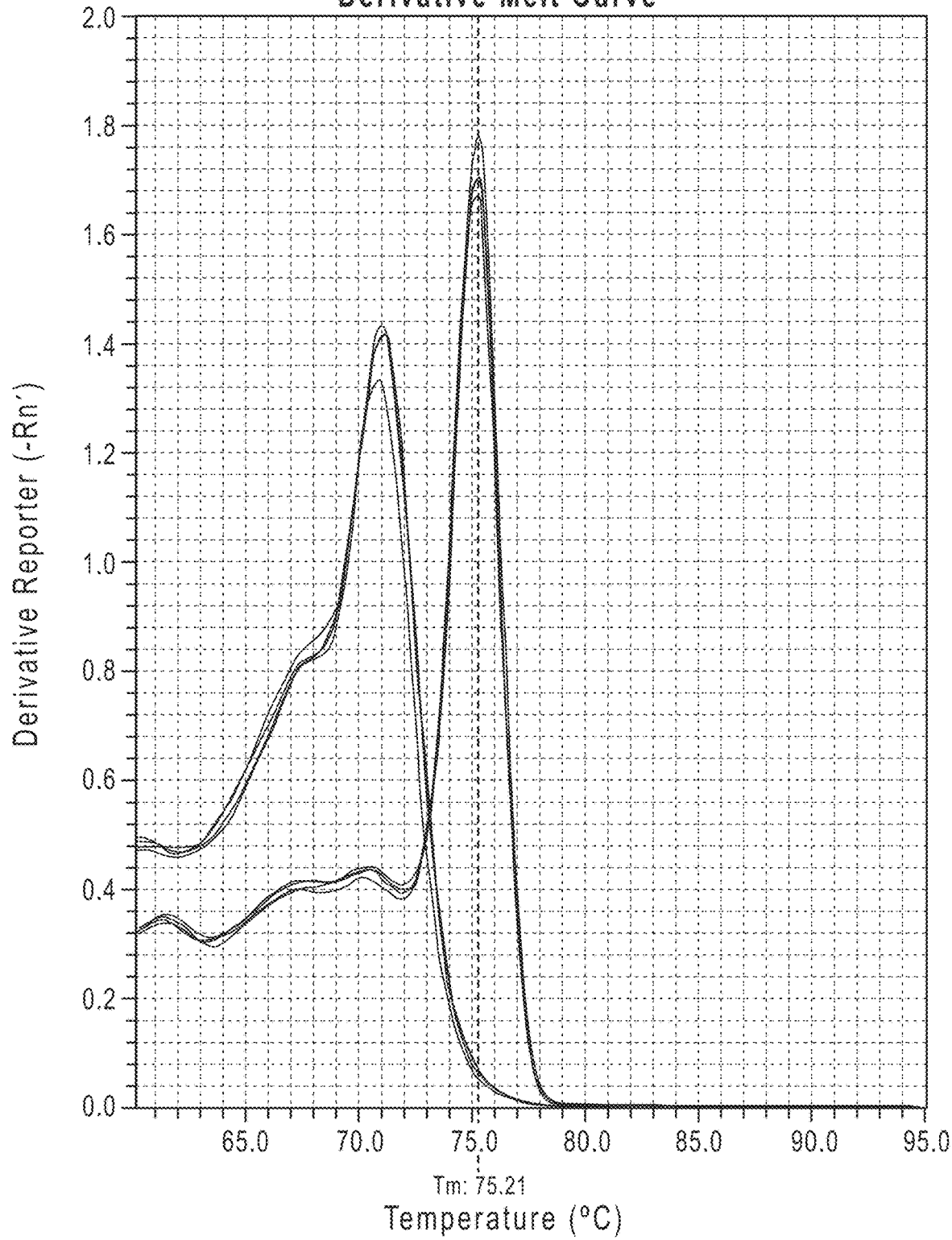
Figures 2, 2J:
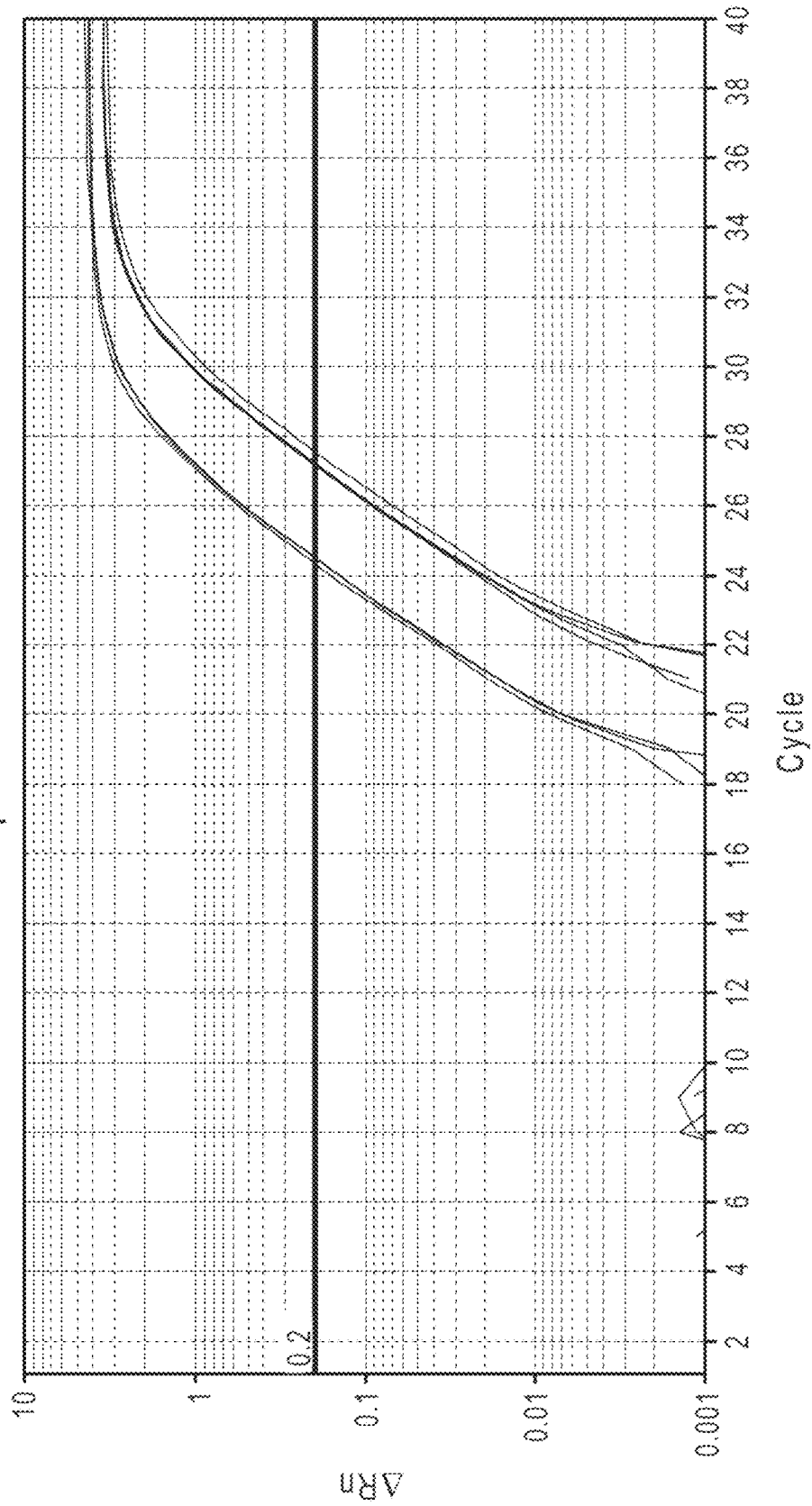
Figures 1, 2K:
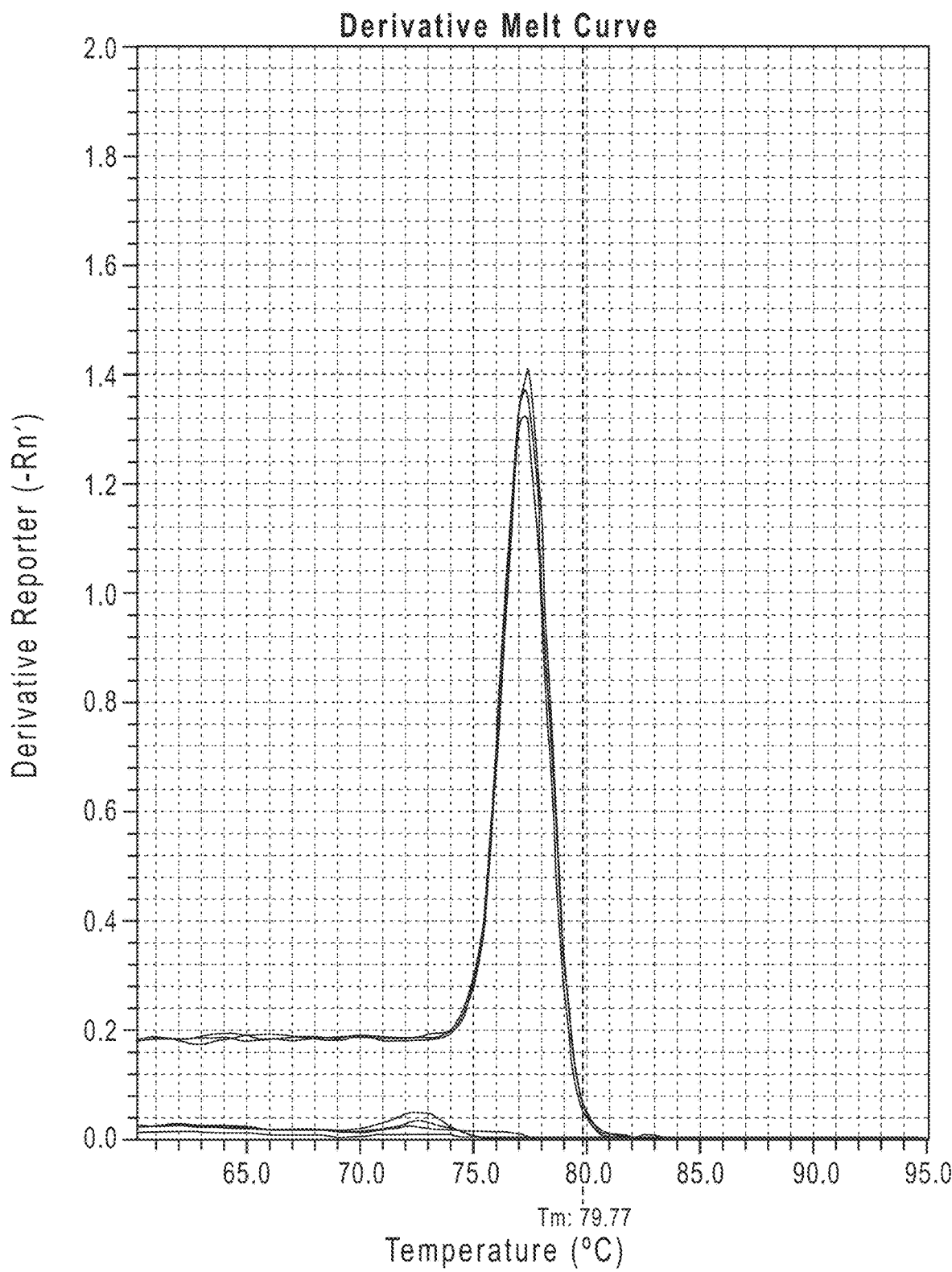
Figures 2, 2K:
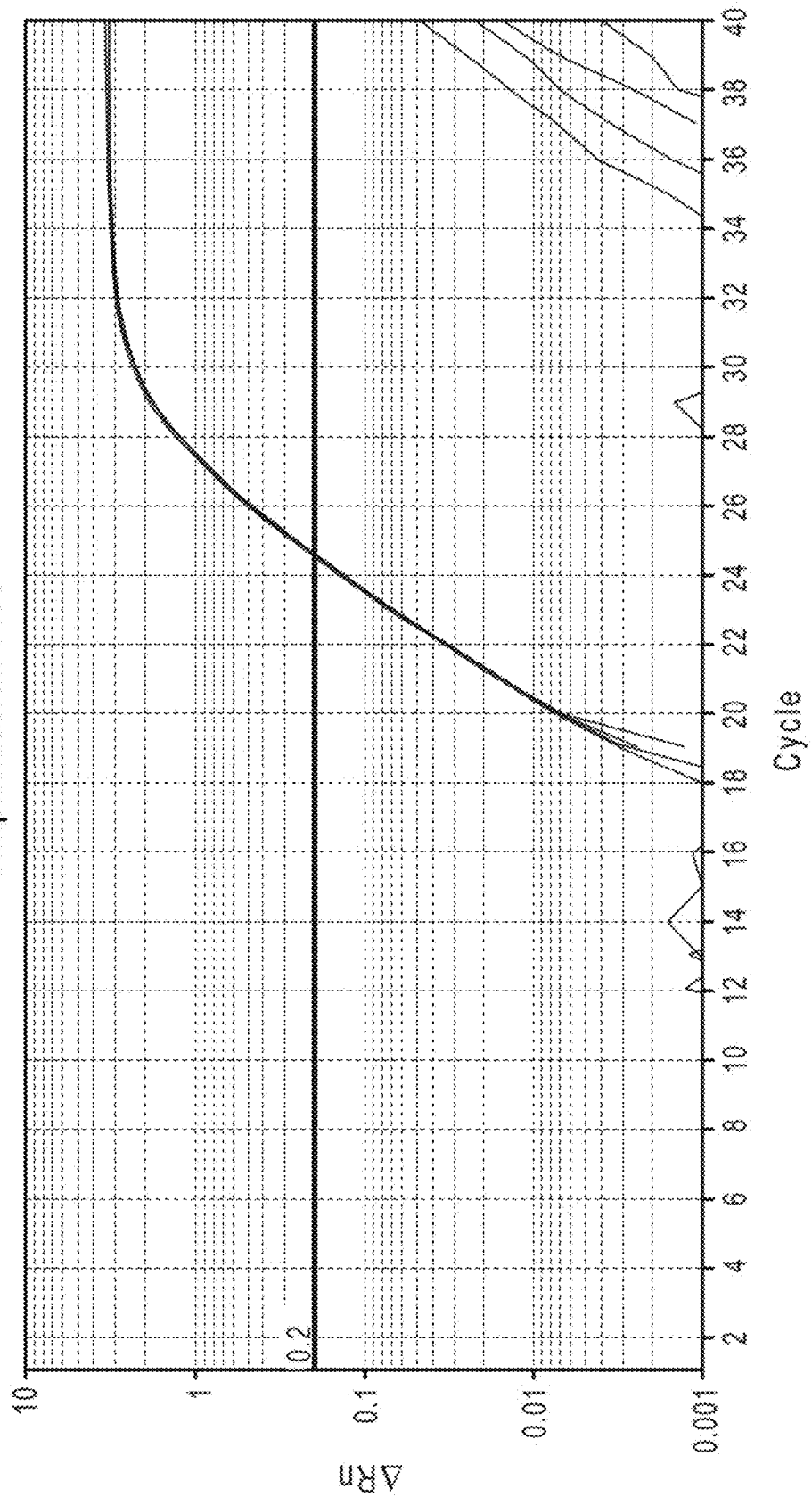
Figures 1, 2L:
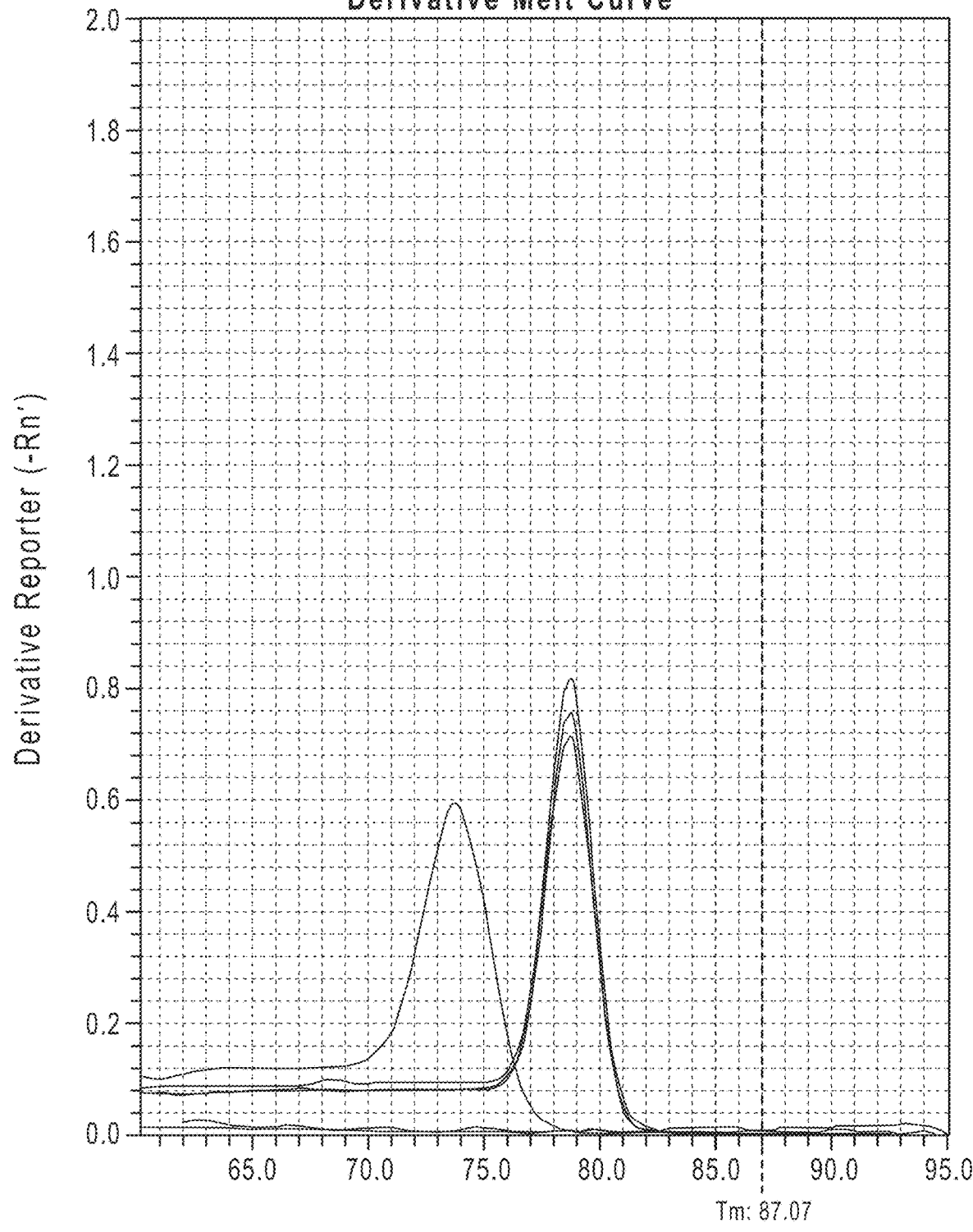
Figures 2, 2L:
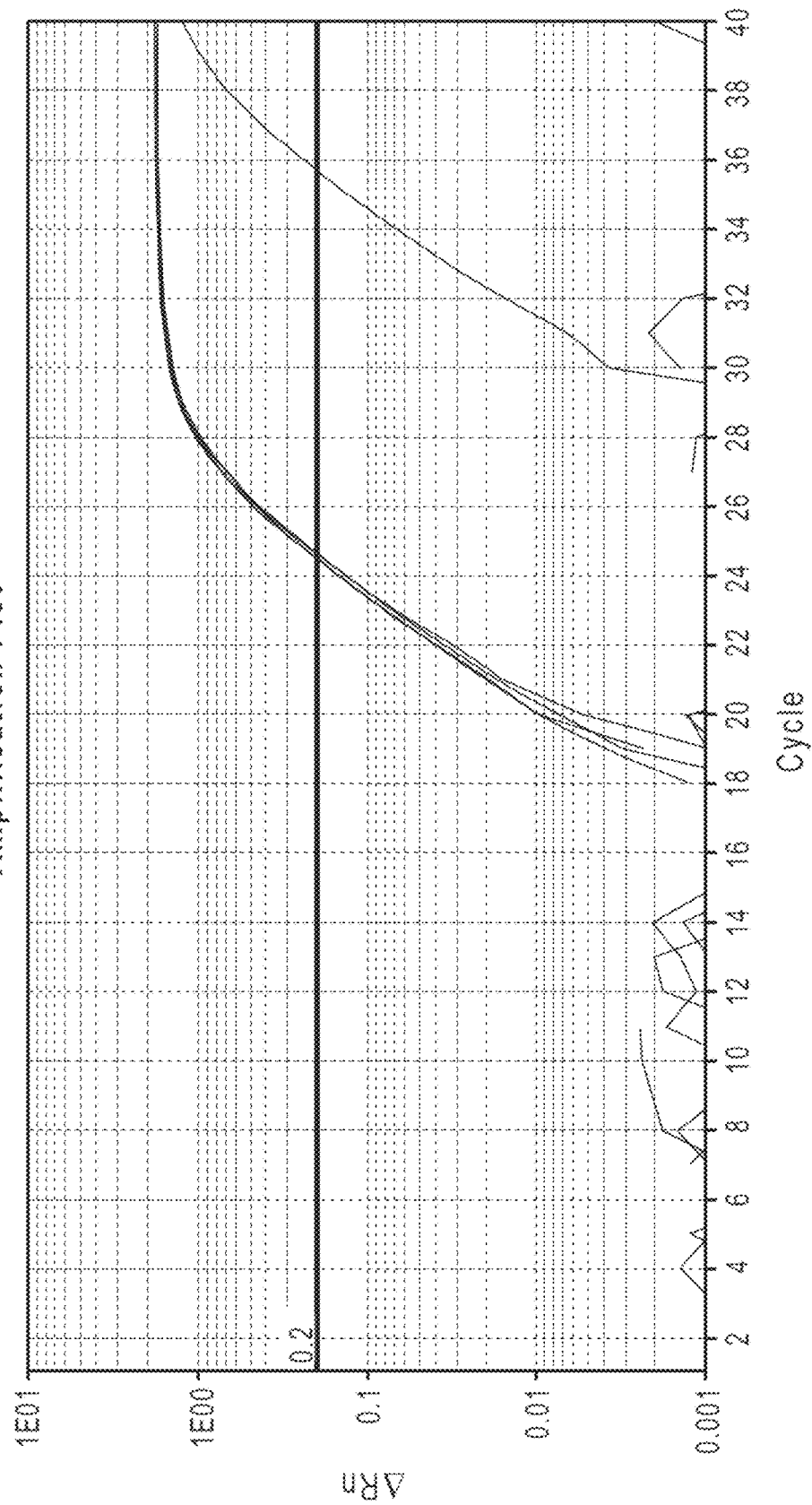
Figure 3A:
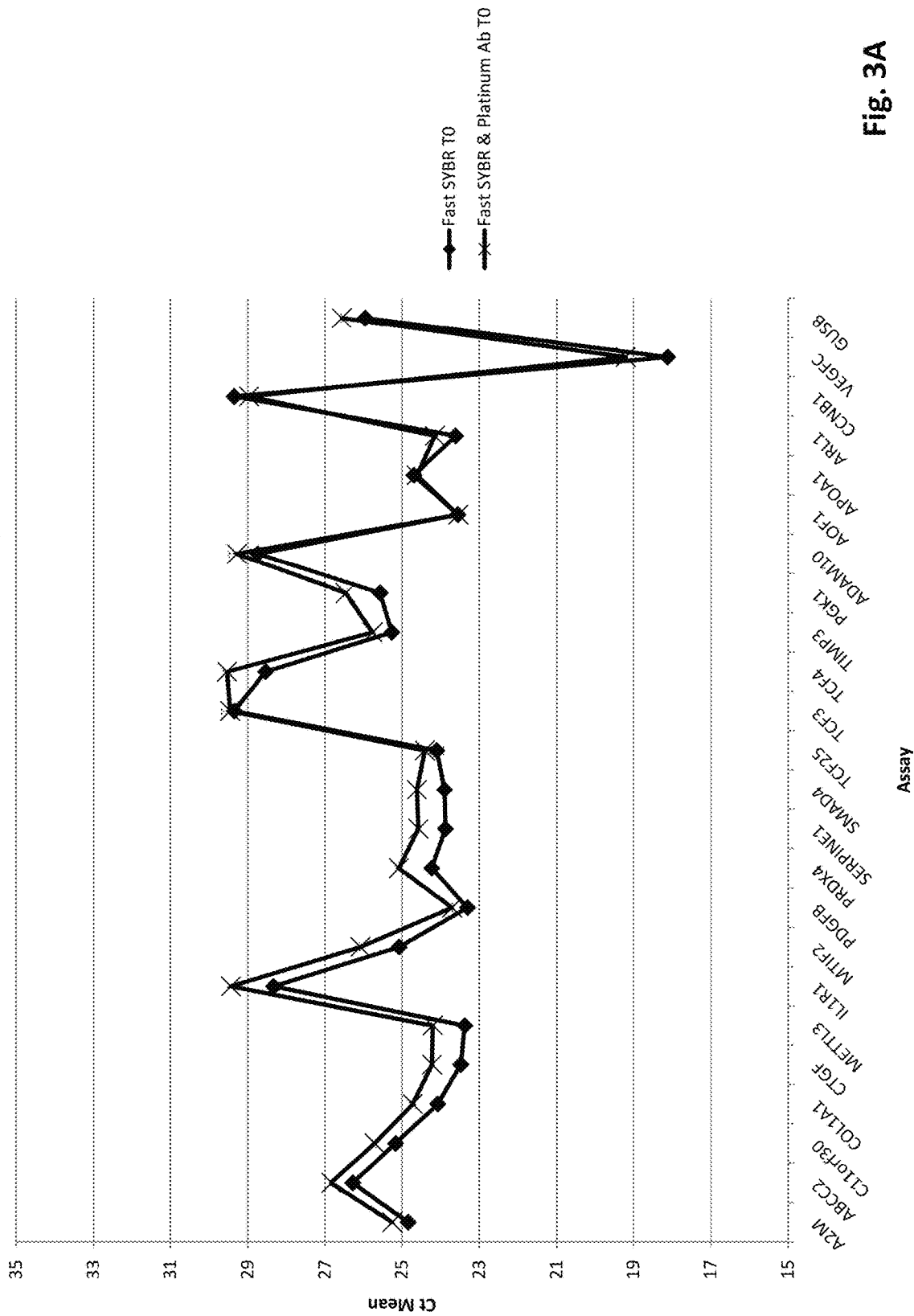
Figure 3B:
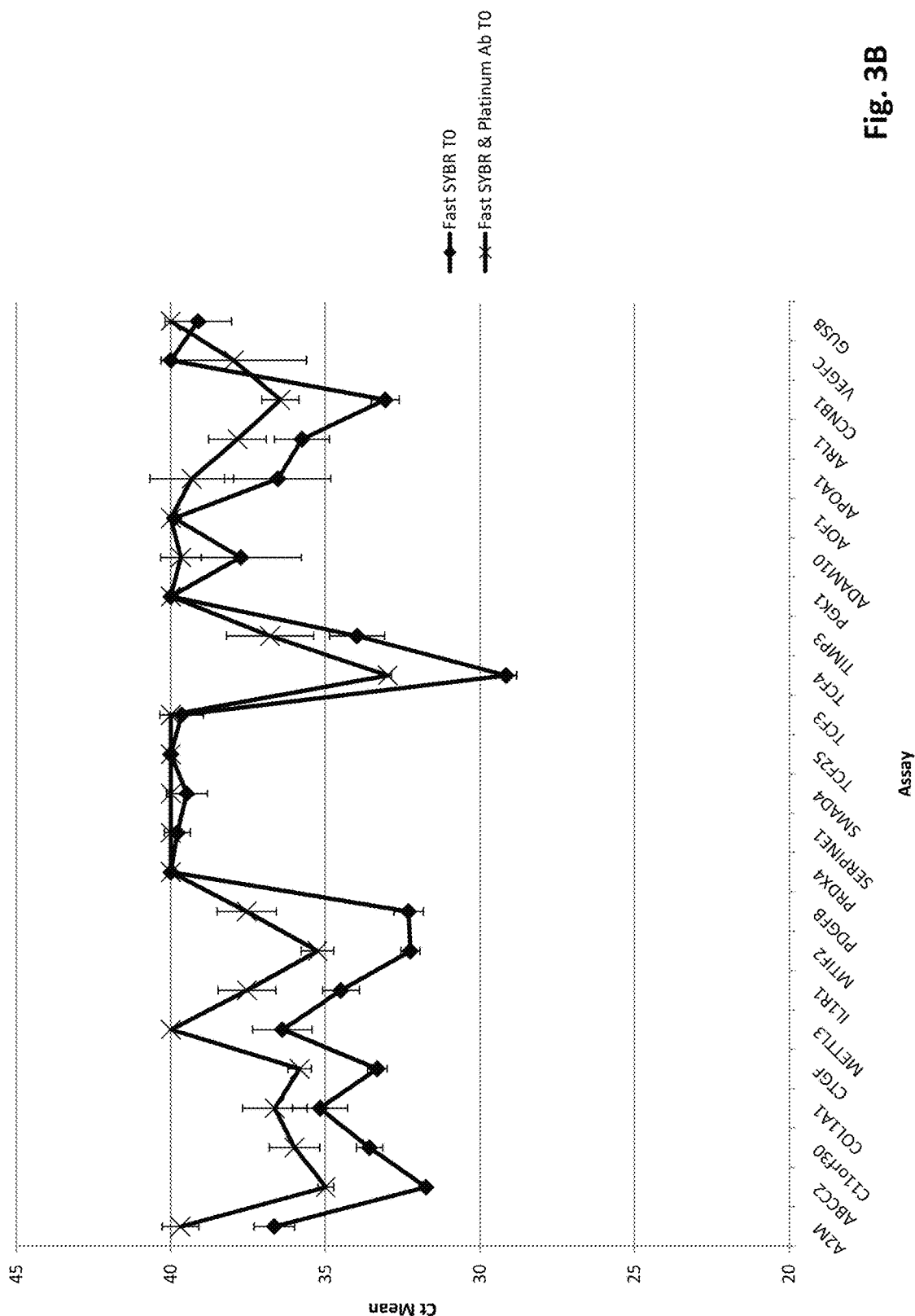
Figure 3D:
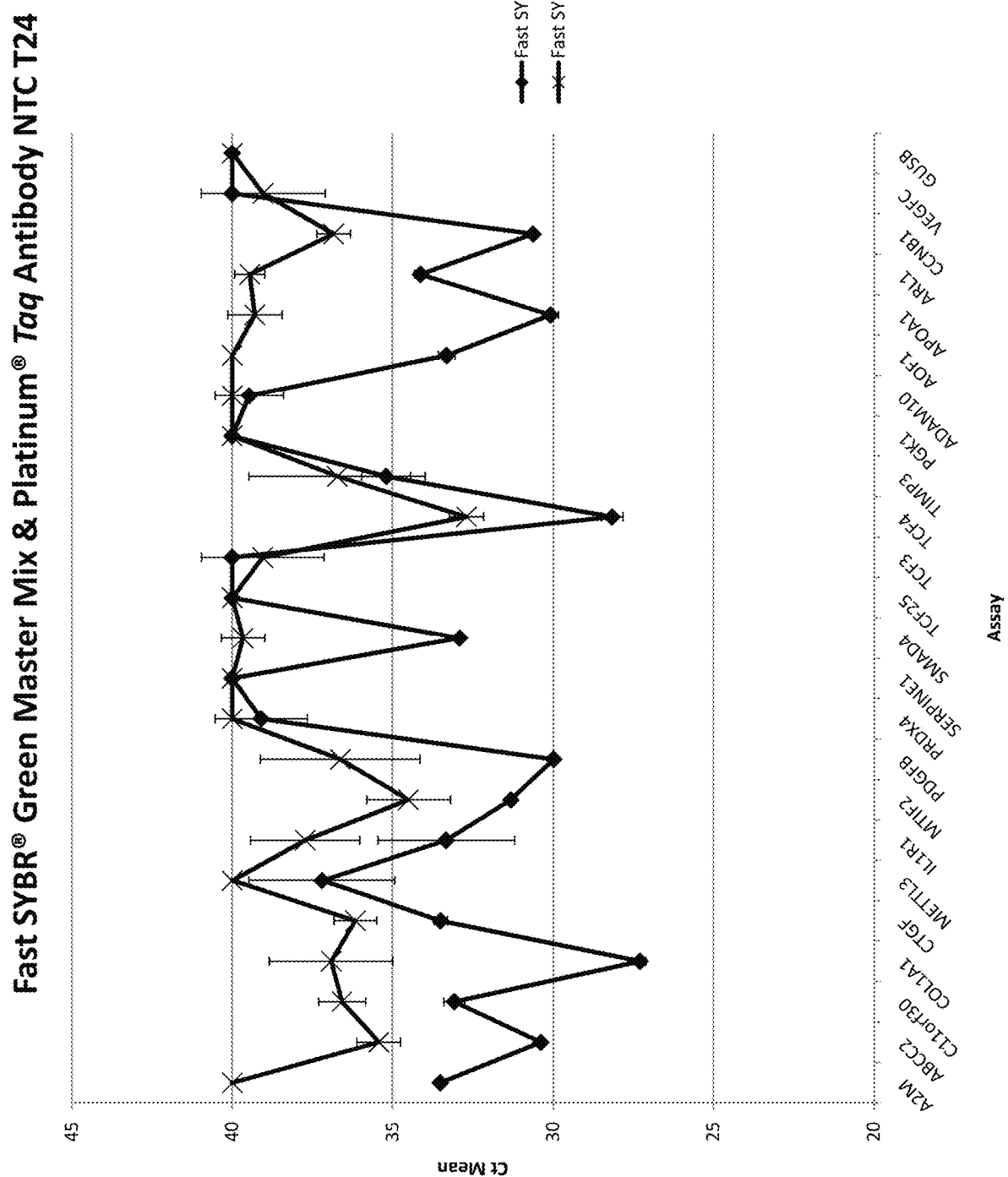
Figures 1, 4A:
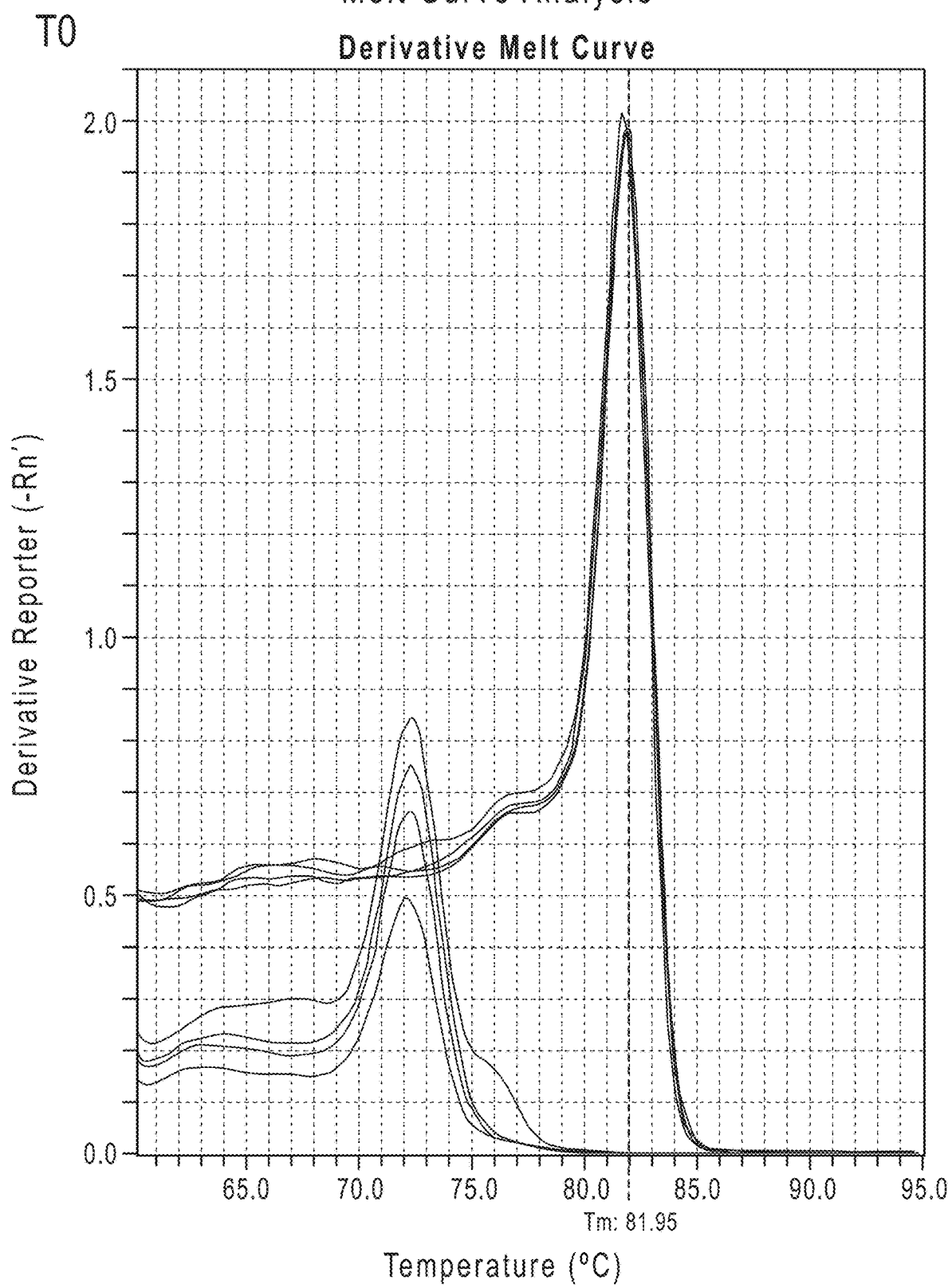
Figures 2, 4A:
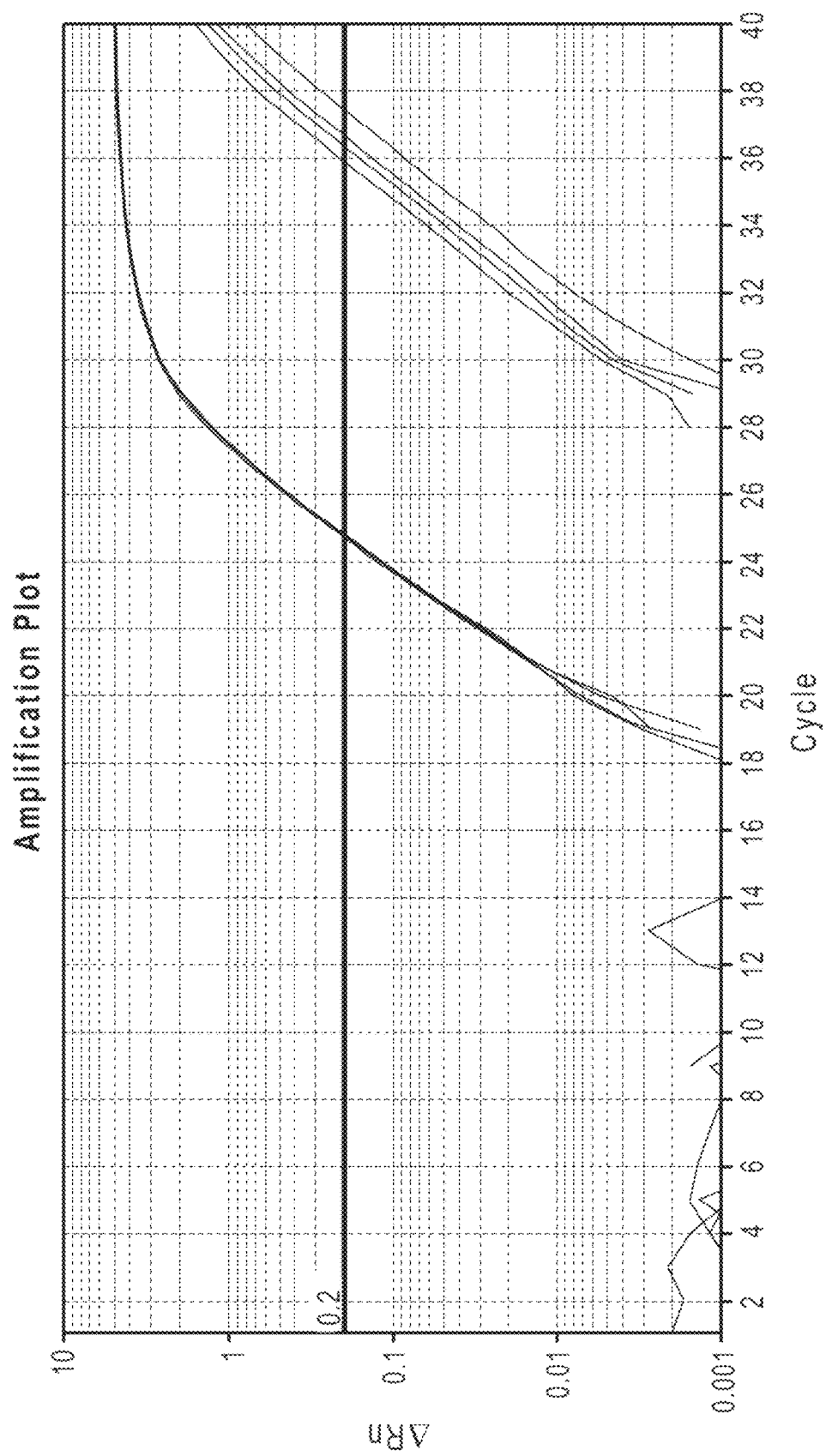
Figures 1, 4B:
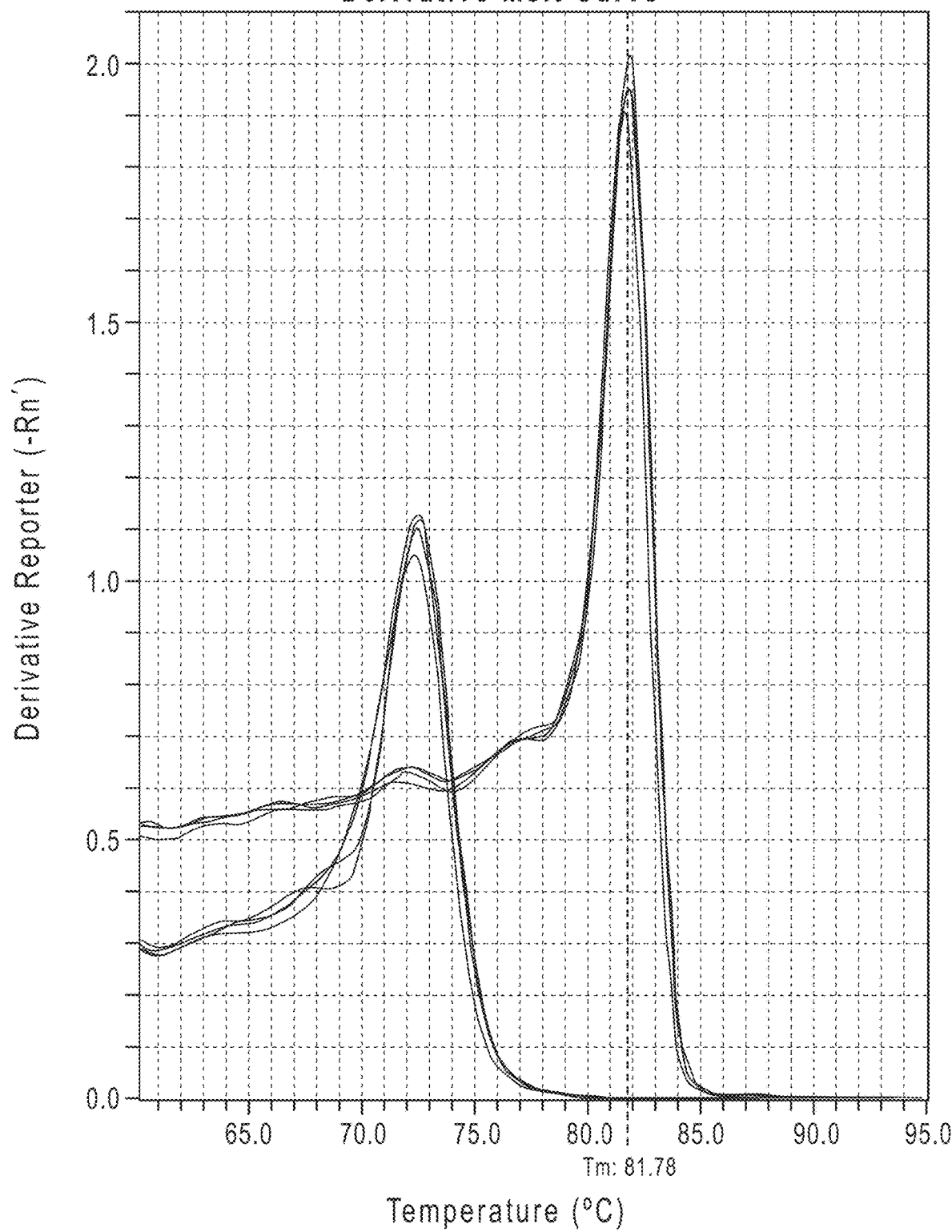
Figures 2, 4B:
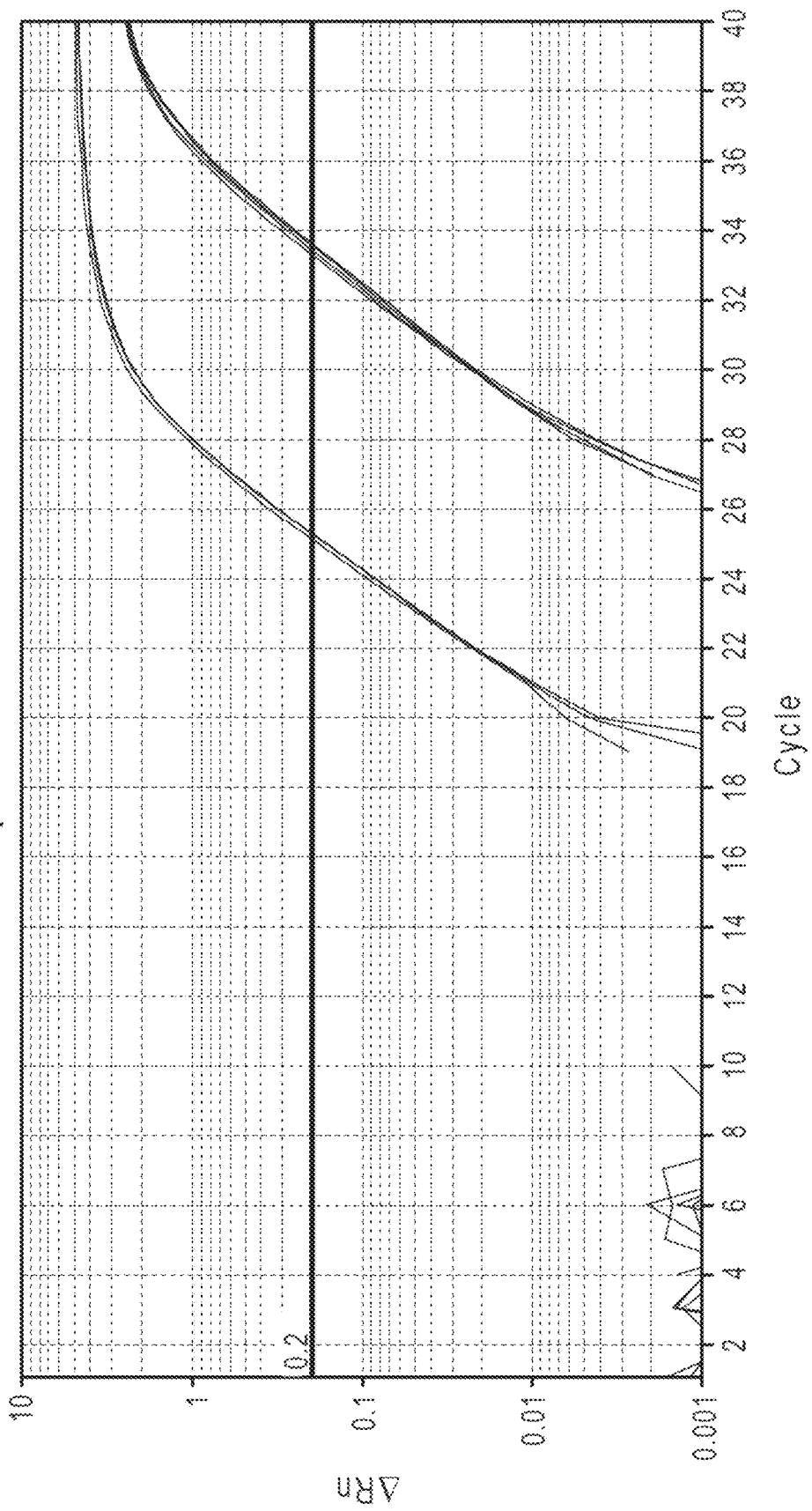
Figures 1, 4C:
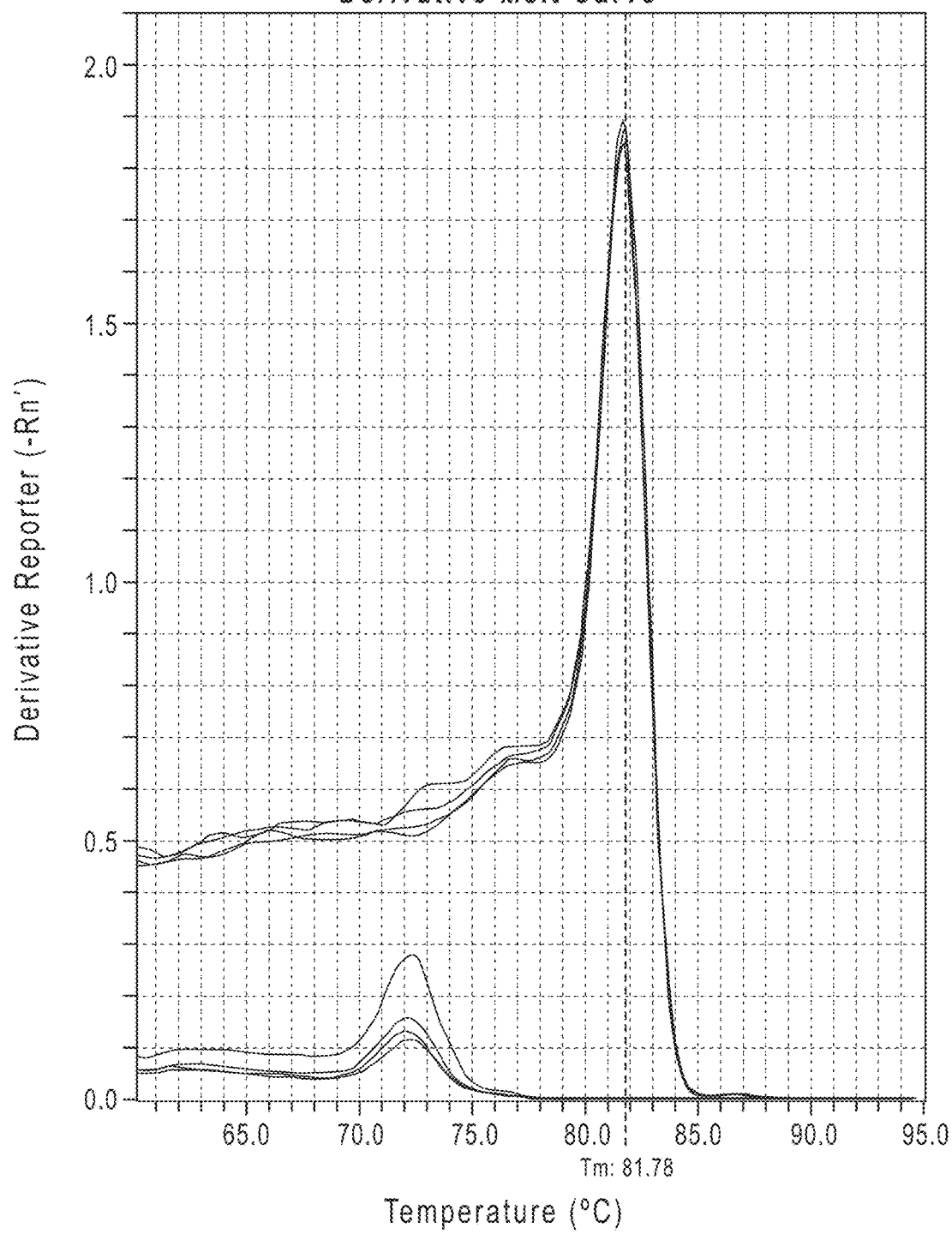
Figures 2, 4C:
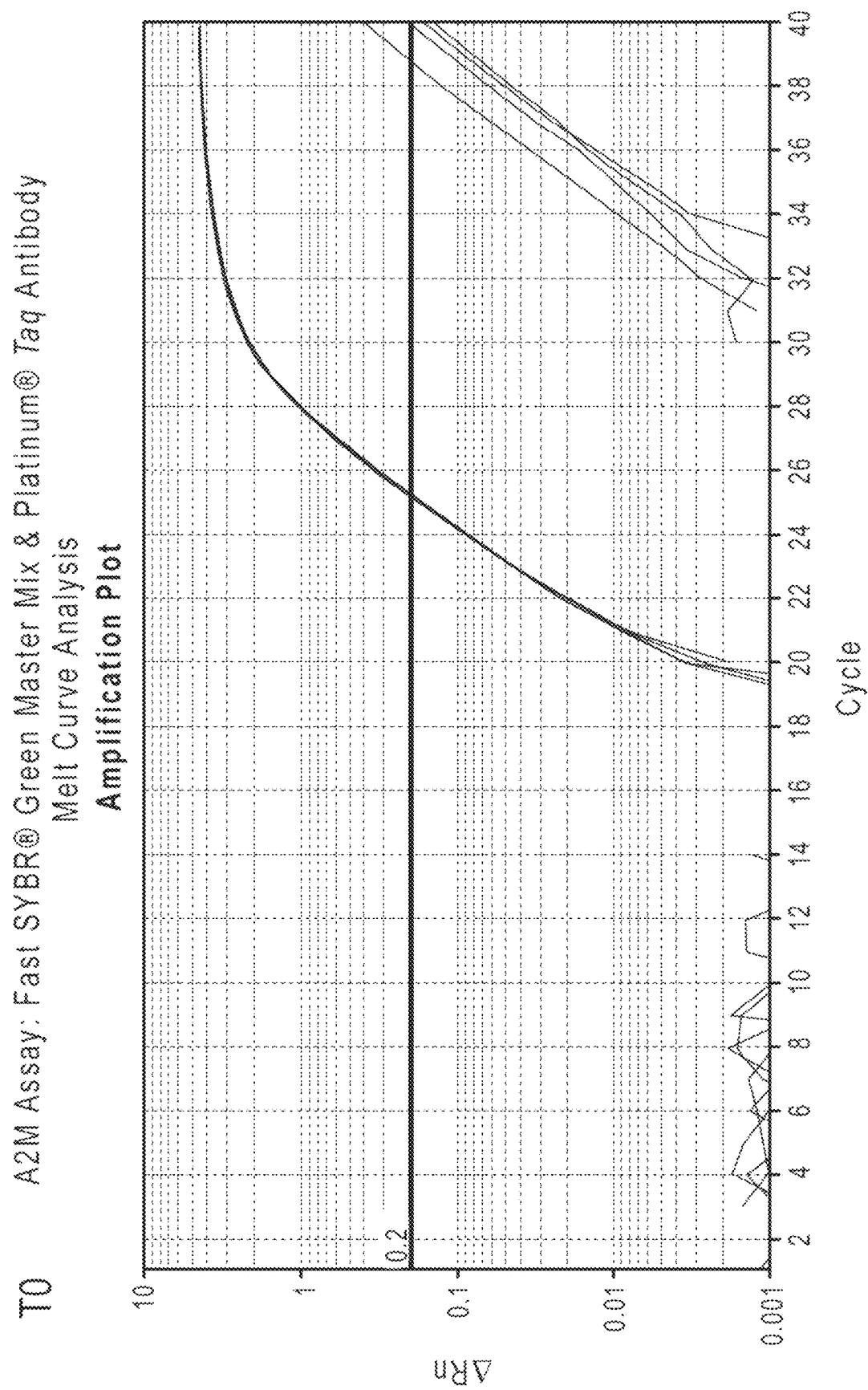
Figures 1, 4D:
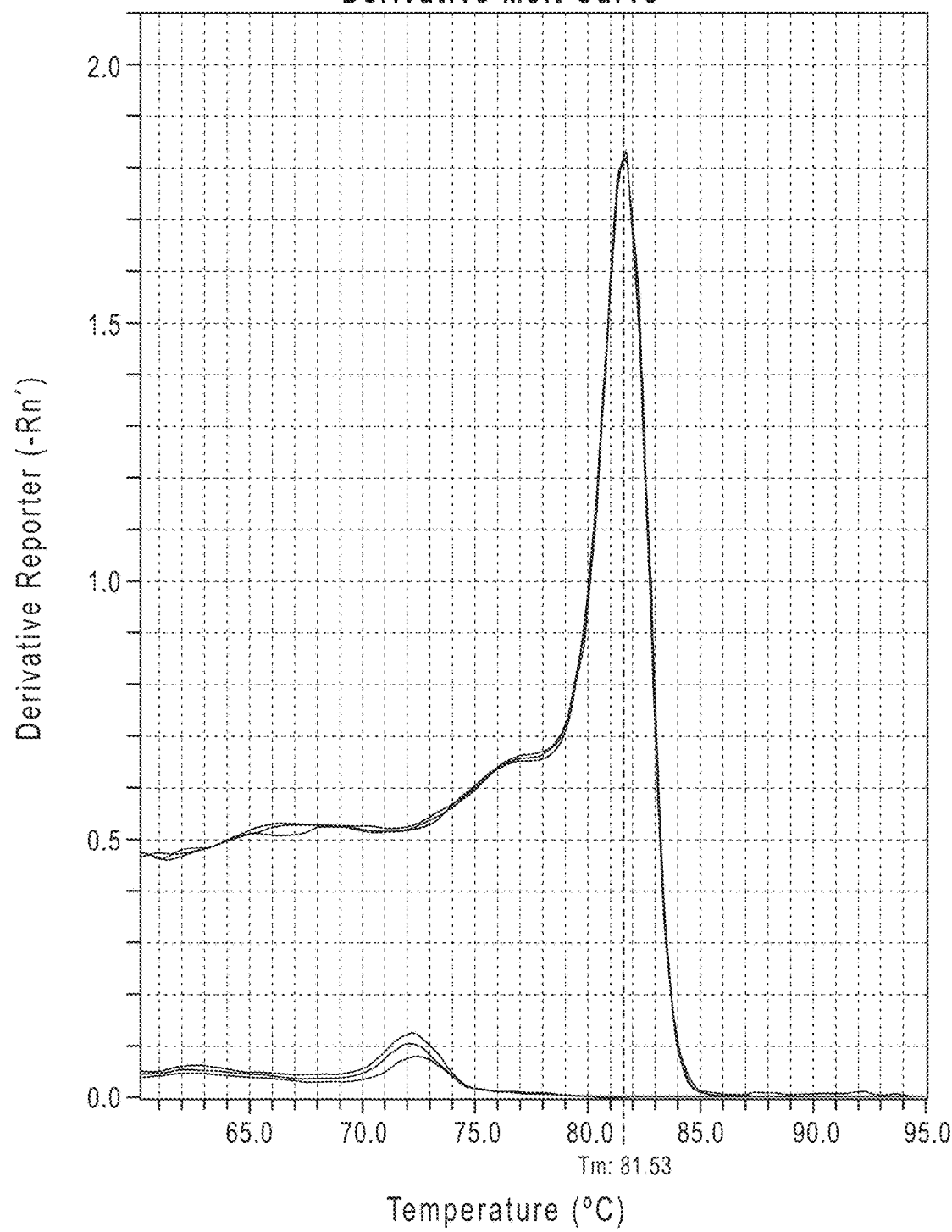
Figures 2, 4D:
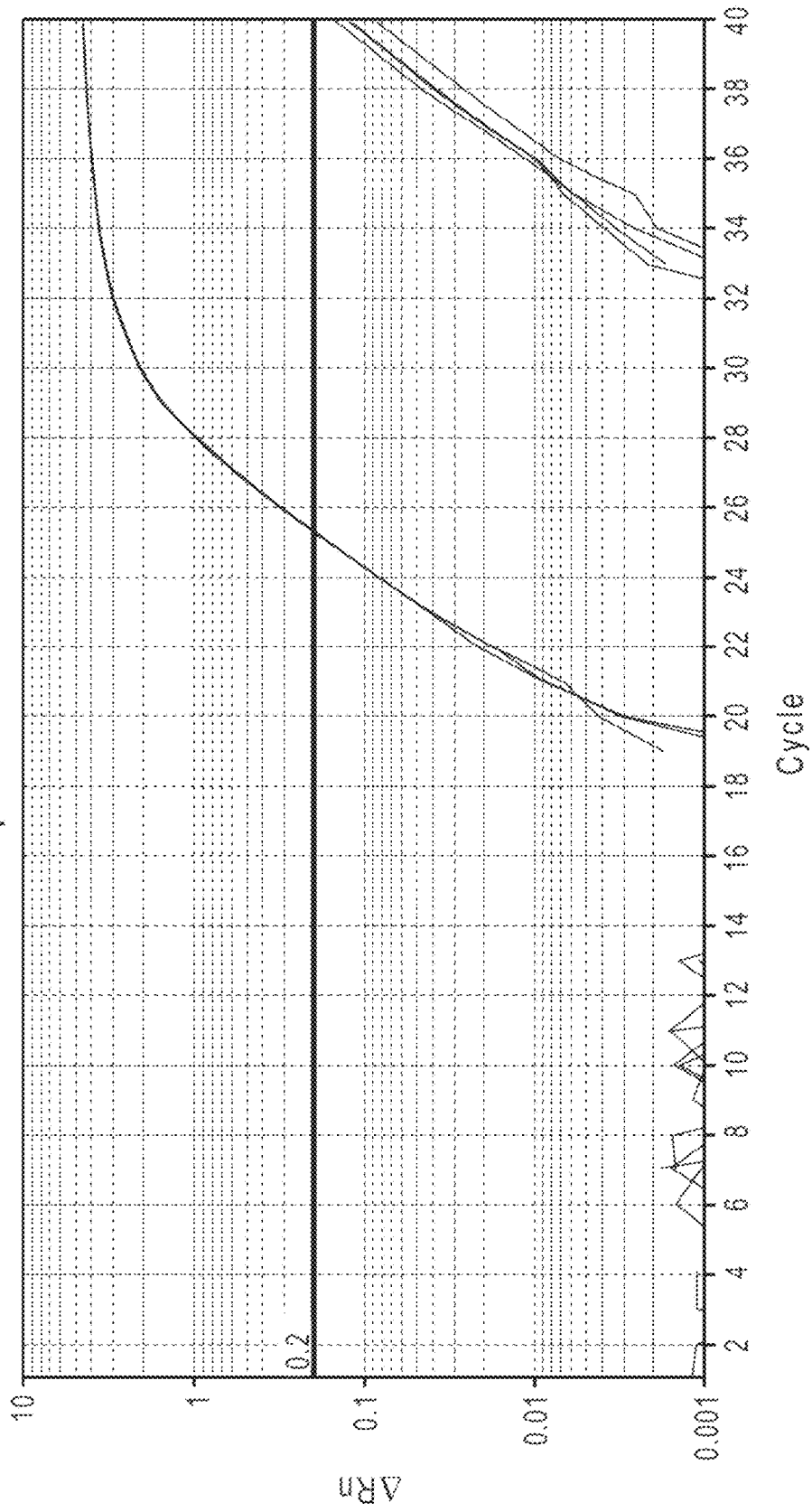
Figure 5A:
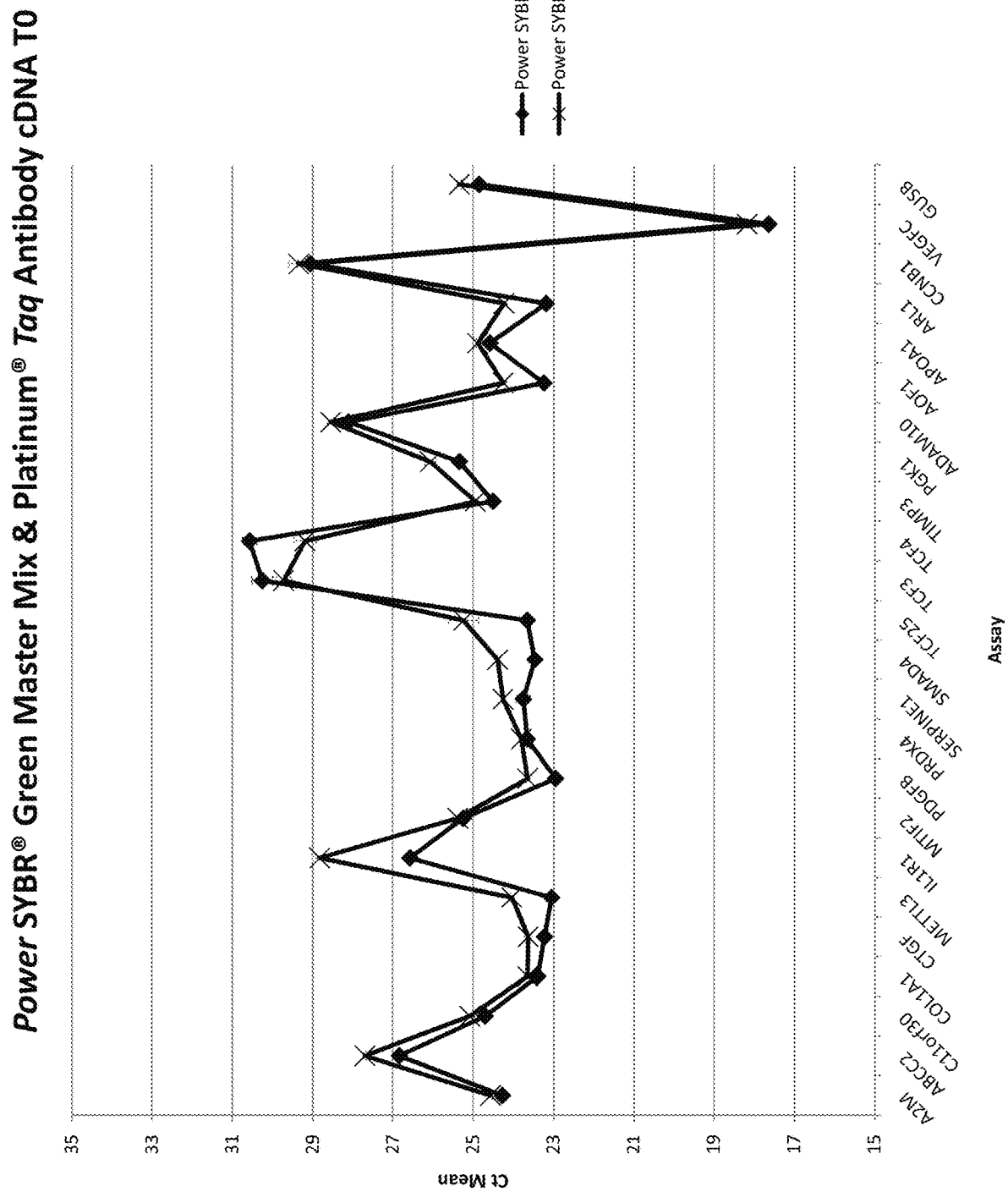
FIGS. 5A through 5D: Comparison of Power SYBR® Green PCR Master Mix alone ("diamond" line) and combination of Power SYBR® Green PCR Mix and Platinum® Taq Antibody ("cross" line).
Figure 5B:
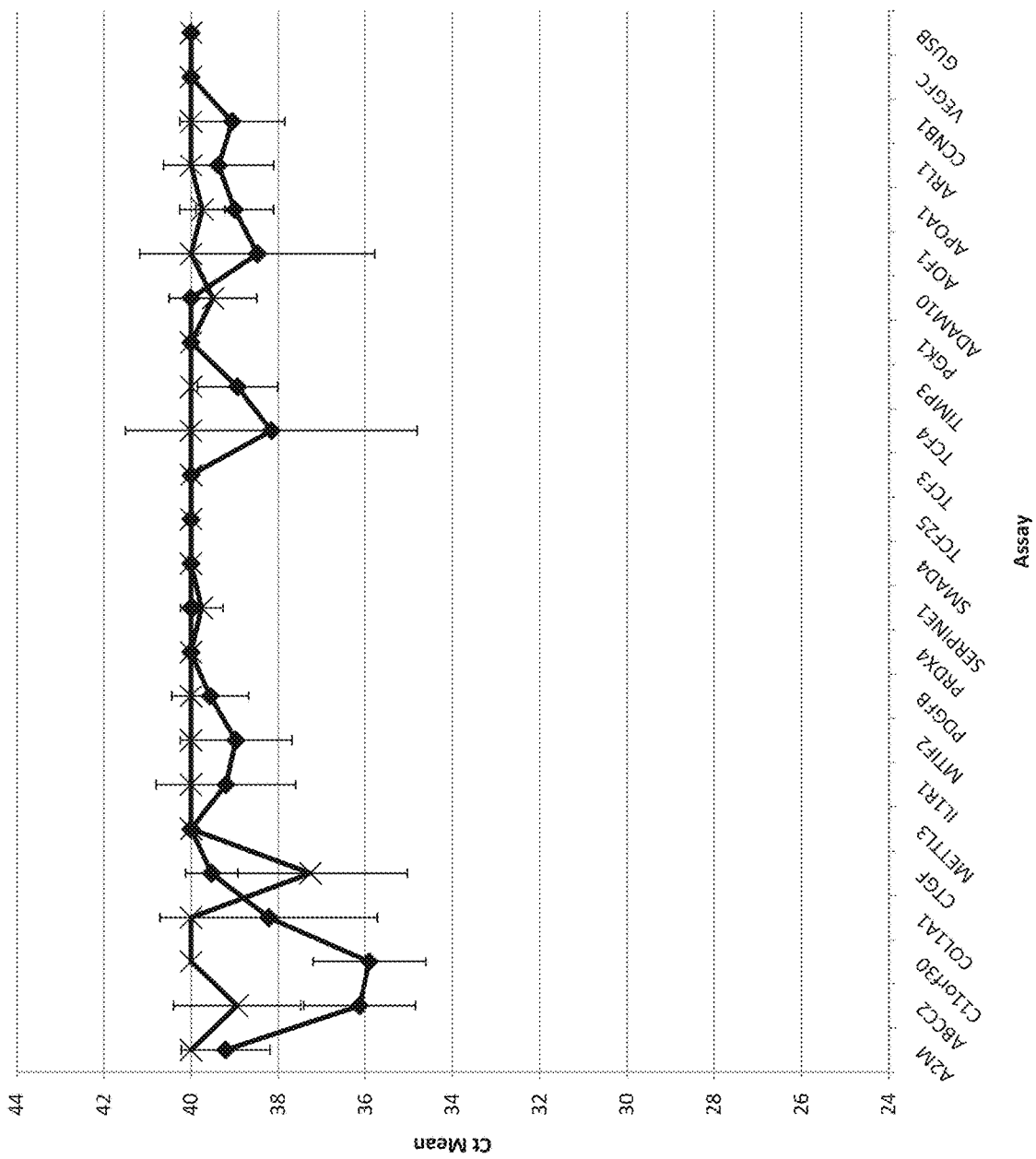
Figure 5C:
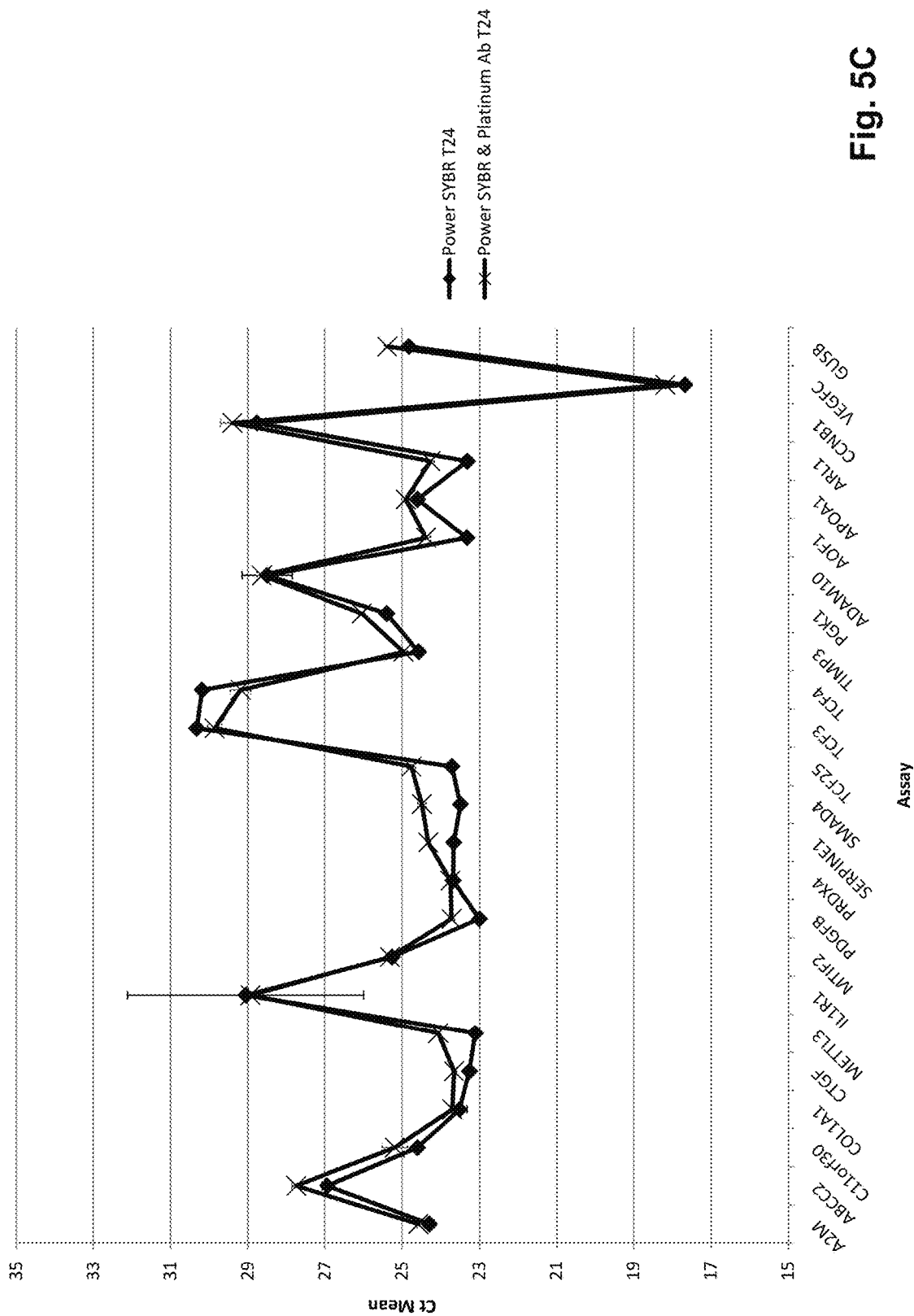
Figure 5D:
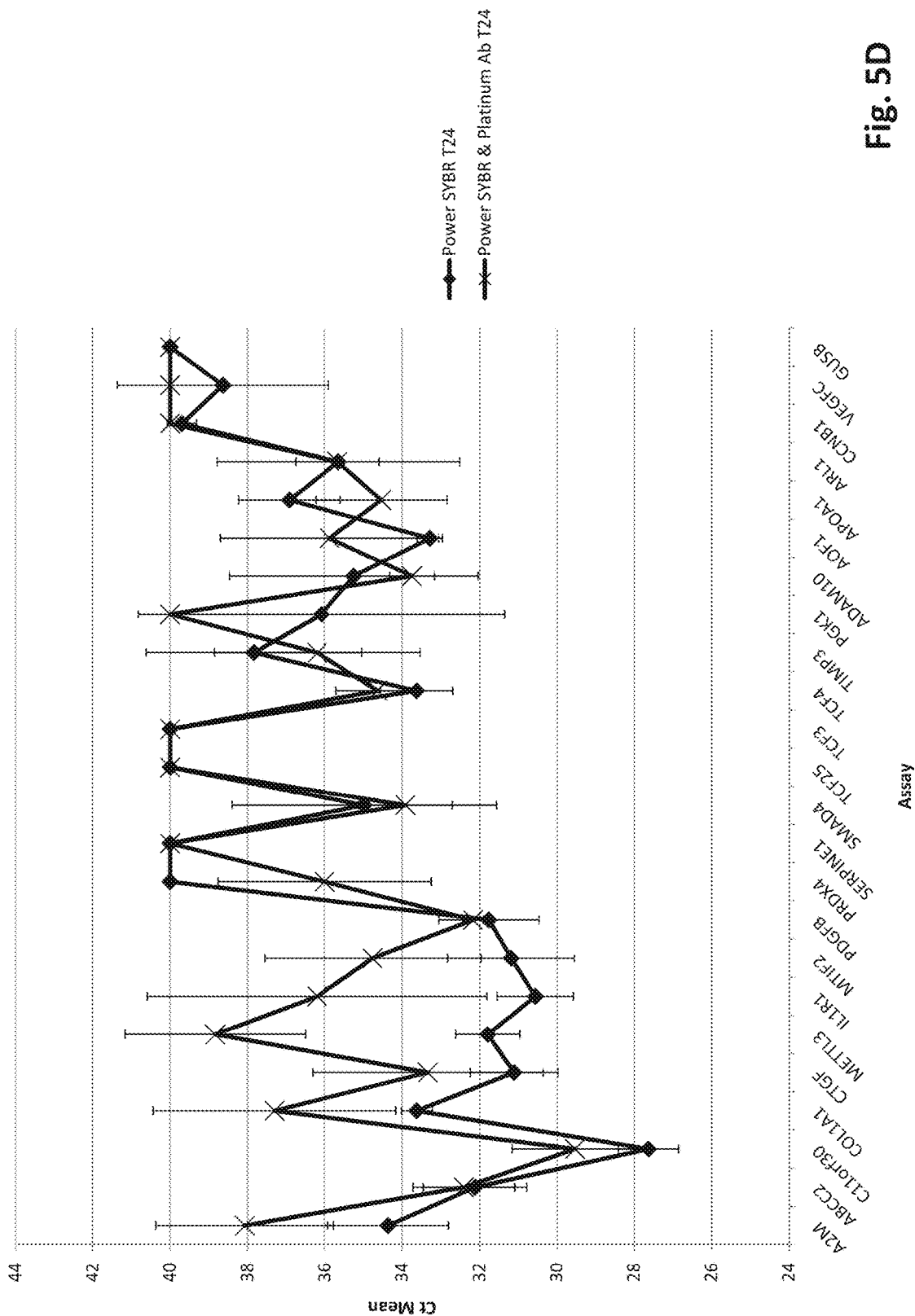

In FIGS. 4A-1 through 4F-2, individual amplicons were selected and analyzed by melt curve analysis. FIG. 4A-1 through 4B-2 demonstrates that the Fast SYBR® Green Master Mix single hot start reaction mixture produces non-specific products, especially after a 24 hour pre-incubation at room temperature. FIG. 4C-1 through 4E demonstrates that the dual hot start reaction mixture results in a 75% reduction in non-specific product formation at T0 and a 100% reduction in non-specific product formation at T24. FIG. 4F demonstrates that the dual hot start reaction mixture reduces the formation of non-specific products at both T0 and T24 and that the dual hot start reaction mixture reduces the formation of non-specific products by 20-25% (depending on the threshold value used).

In FIGS. 5A-5D, the target nucleic acid was amplified with 24 primer sets using either a single or a dual hot start reaction mixture. The single hot start reaction mixtures used either Power SYBR® Green PCR Master Mix alone ("diamond" line) or in combination with Platinum® Taq Antibody ("cross" line). Both reaction sets were incubated at room temperature for either 0 hours ("T0") or 24 hours ("T24") before amplification. In many of the assays, the combination of the two different hot start mechanisms resulted in a decrease in the formation of non-specific products (see, FIGS. 5A (T0, cDNA), 5B (T0, non-specific product ("NTC")), 5C (T24, cDNA), and 5D (T24, NTC)).

Figures 1, 6A:
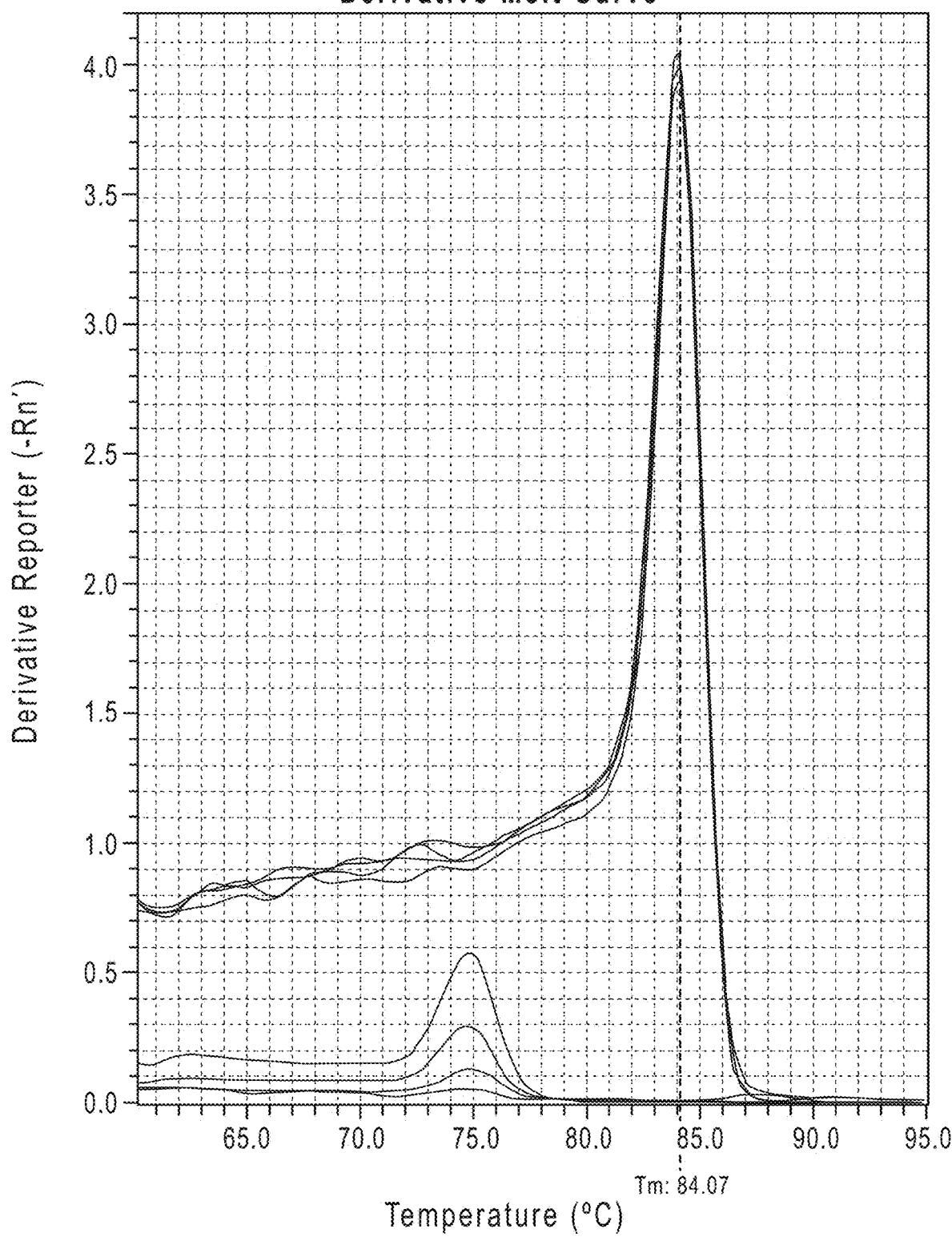
Figures 2, 6A:
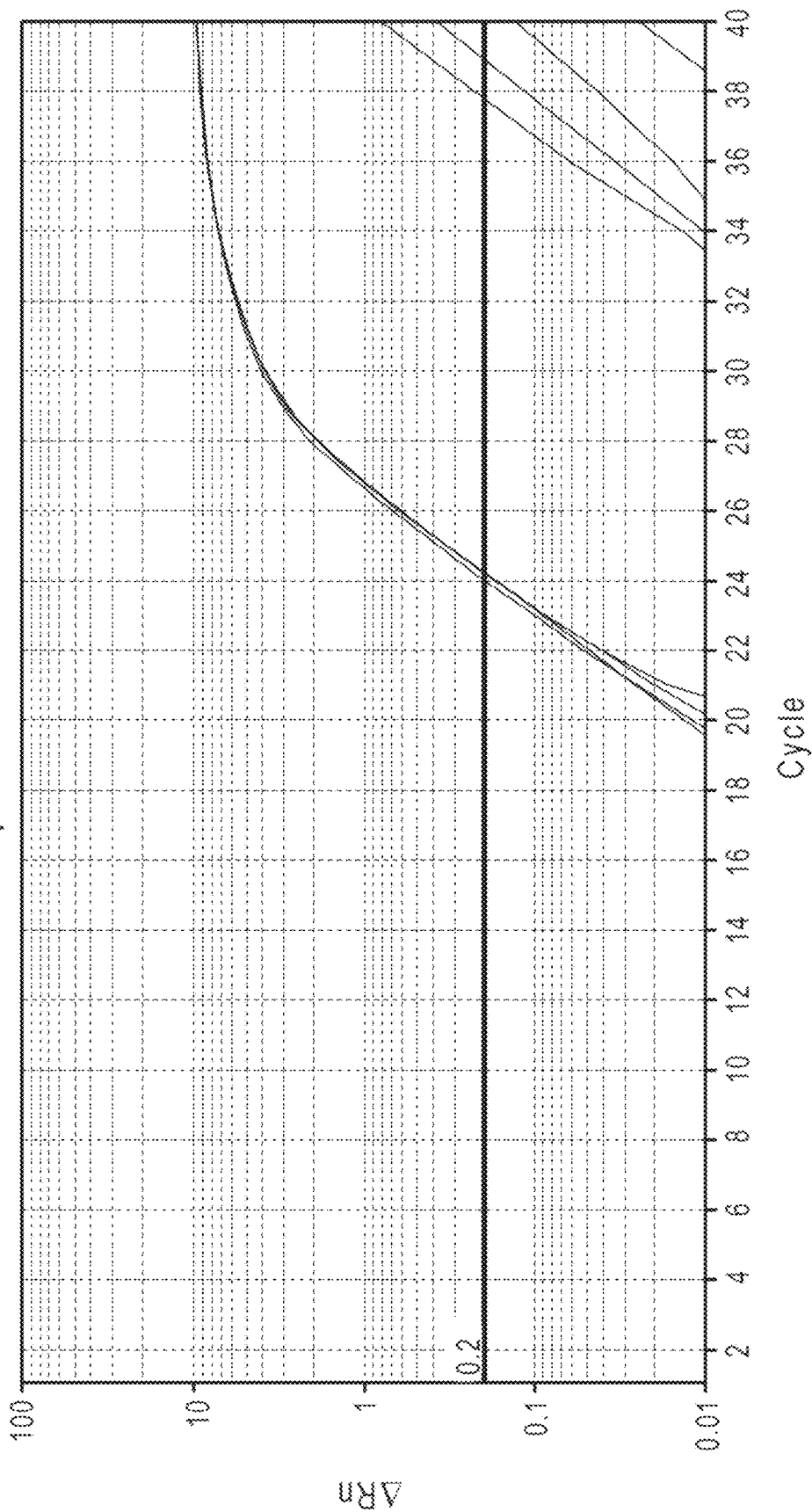
Figures 1, 6B:
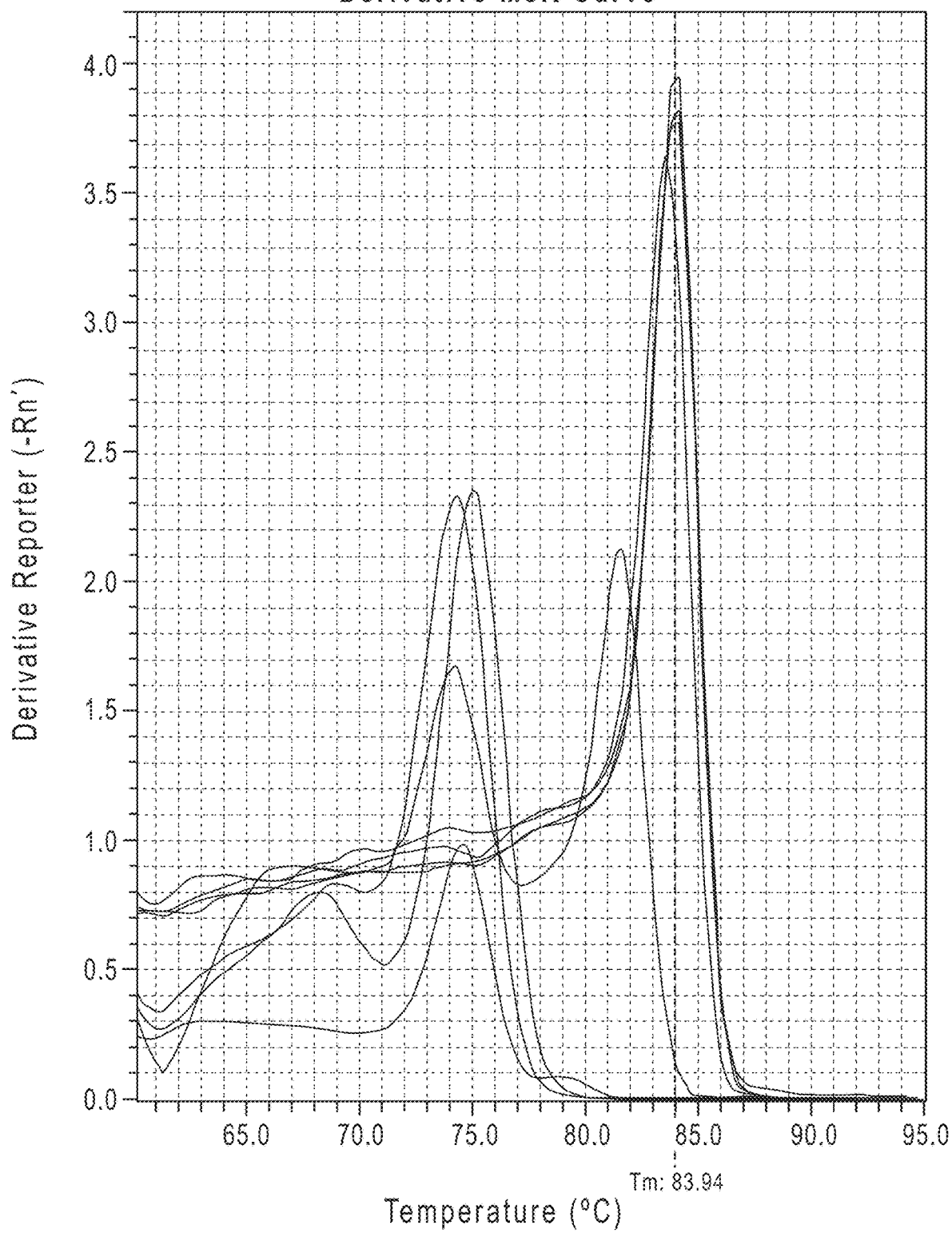
Figures 2, 6B:
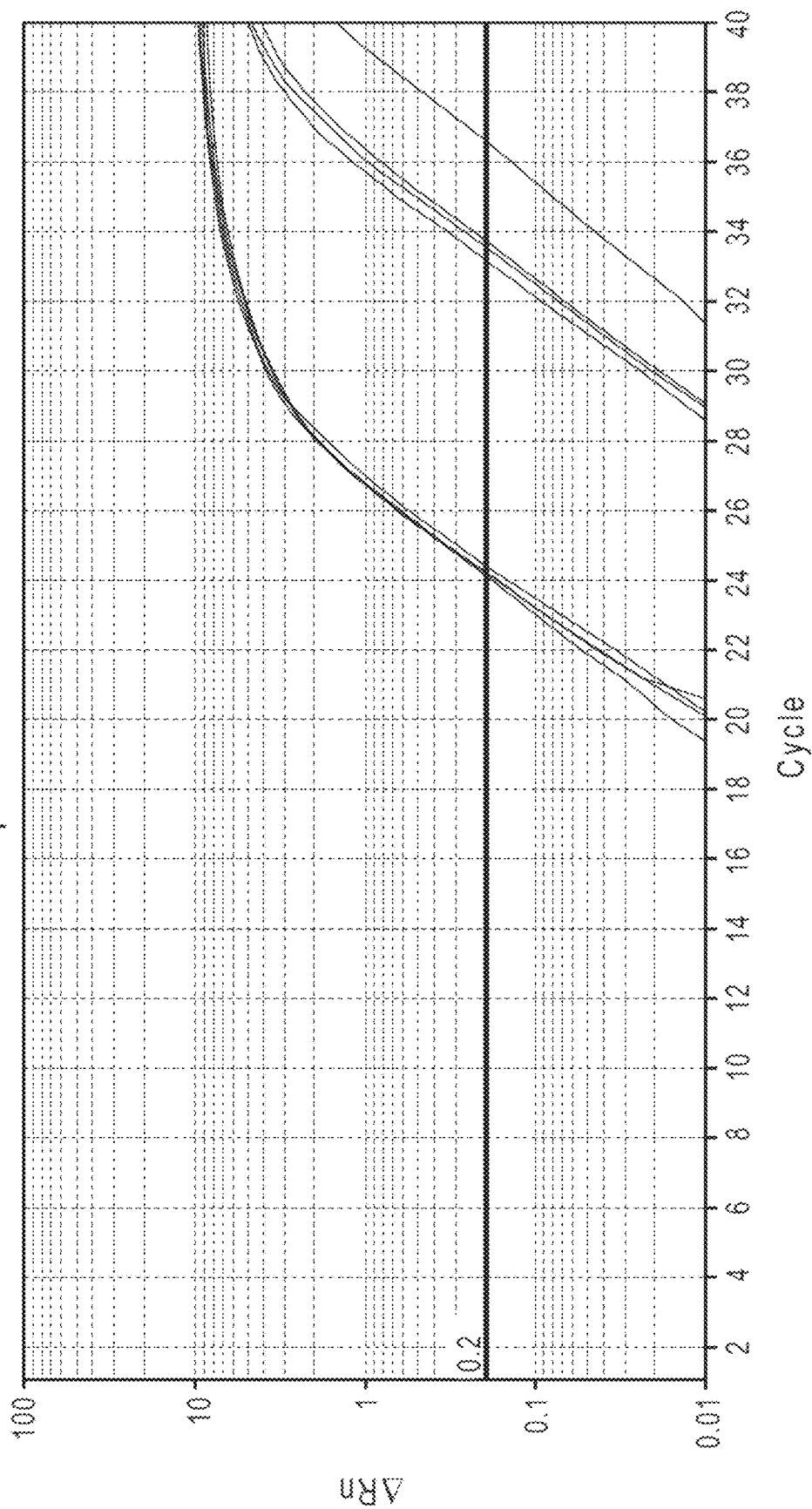
Figures 1, 6C:
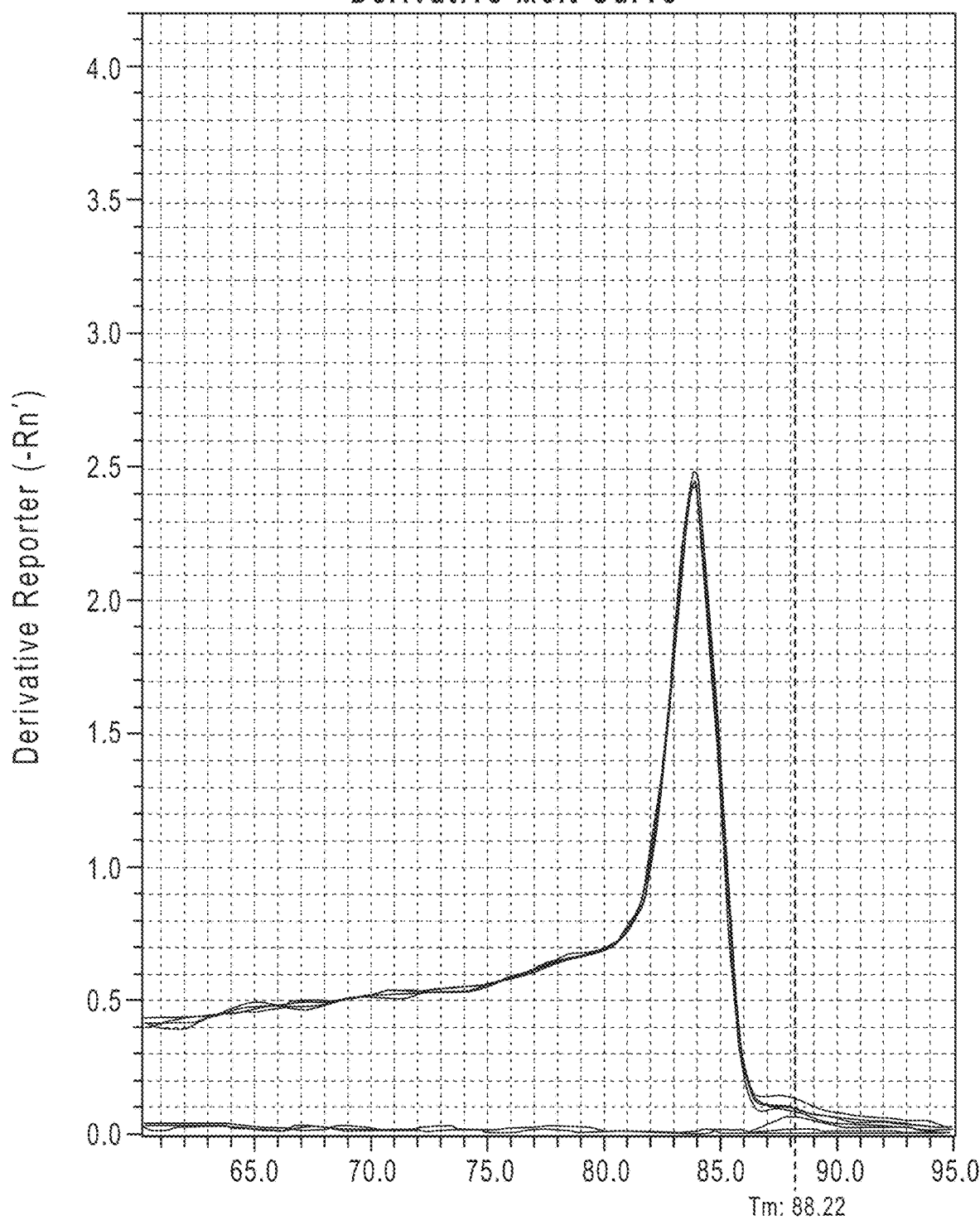
Figures 2, 6C:
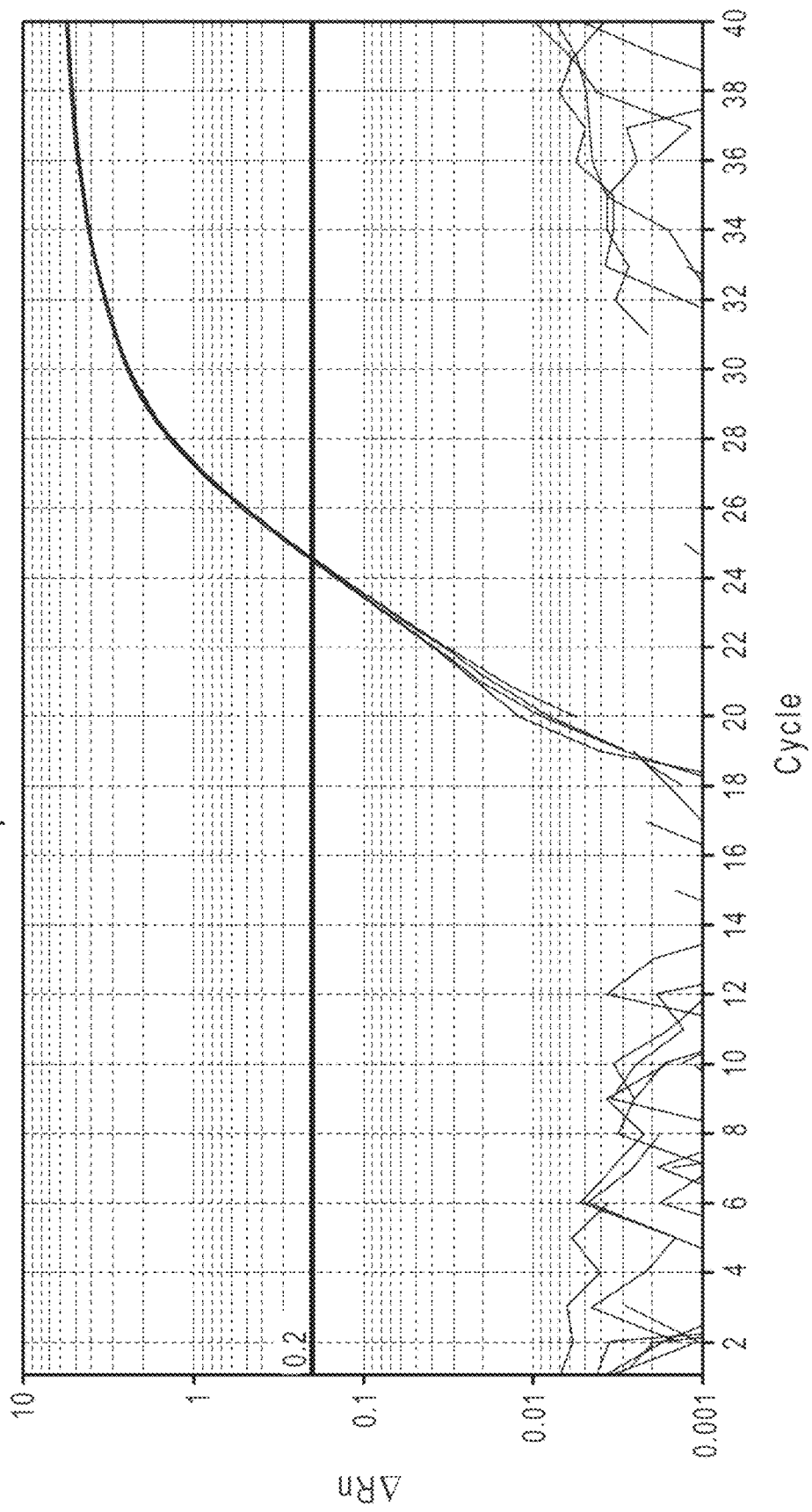
Figures 1, 6D:
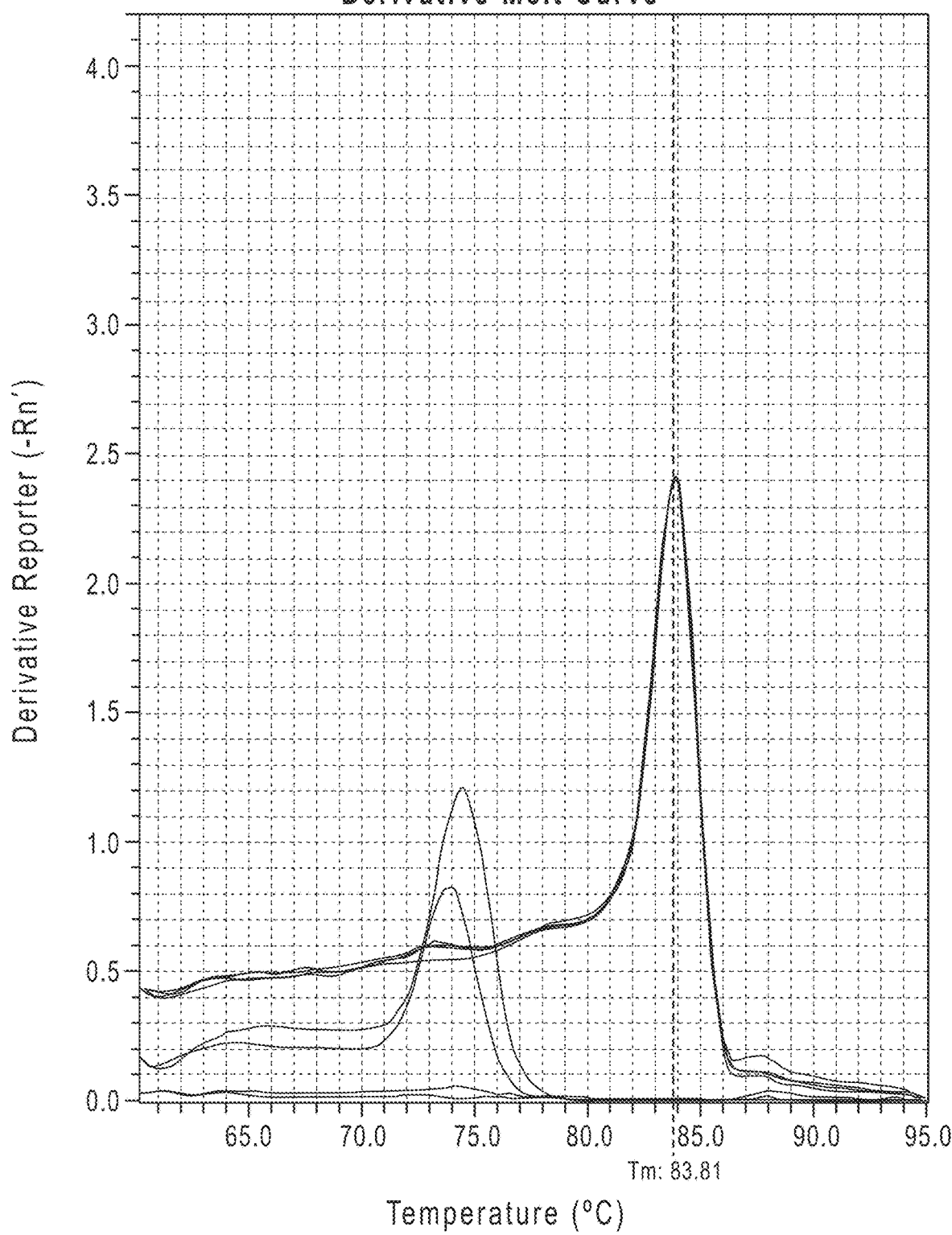
Figures 2, 6D:
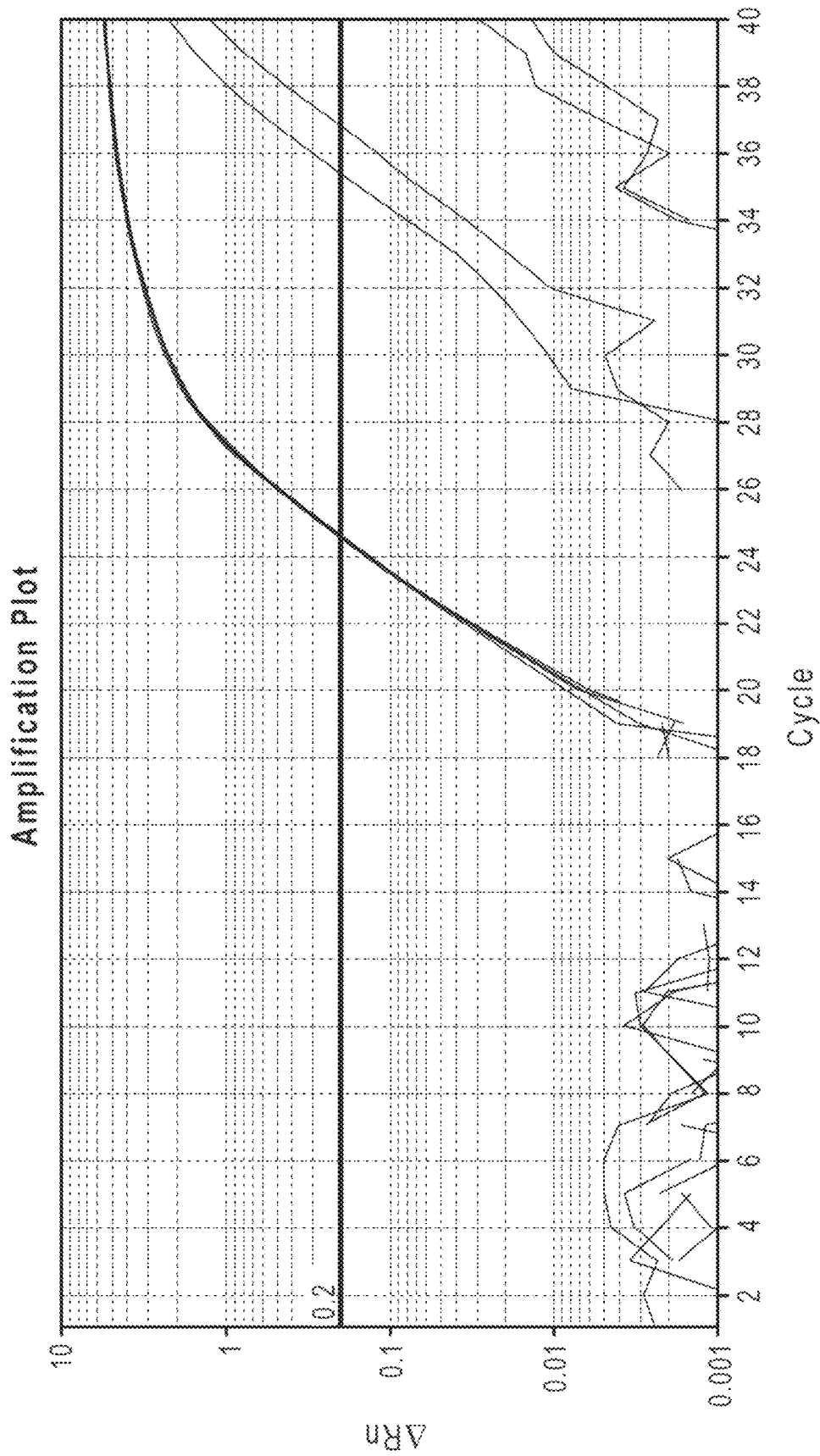

In FIGS. 6A-1 through 6E-2, individual amplicons were selected and analyzed by melt curve analysis. FIG. 6A-1 through 6B-2 demonstrates that the Power SYBR® Green PCR Master Mix single hot start reaction mixture produces non-specific products, especially after a 24 hour pre-incubation at room temperature. FIG. 6C-1 through 6D-2 demonstrates that the dual hot start reaction mixture results in a 50% reduction in non-specific product formation at 24 hours. FIG. 6E demonstrates that the dual hot start reaction mixture reduces the formation of non-specific products at both T0 and T24 (as shown by a drop in Ct values) and that the dual hot start reaction mixture reduces the formation of non-specific products by 3-fold at T0 and by 10% at T24.

We claim:

1. A method for amplifying a target nucleic acid comprising:
    a) contacting the target nucleic acid with a first nucleic acid polymerase, a dual hot start reaction mixture, at least one primer and at least one dNTP at a first temperature, thereby forming a reaction composition, wherein the dual hot start reaction mixture comprises at least two hot start mechanisms that, together, both inhibit activity of the first nucleic acid polymerase;
    b) heating the reaction composition to a second temperature; and
    c) amplifying the target nucleic acid in the reaction composition.

2. The method of claim 1, wherein the first nucleic acid polymerase is thermostable.

3. The method of claim 1, wherein the first nucleic acid polymerase is a DNA-dependent DNA polymerase or an RNA-dependent DNA polymerase.

4. The method of claim 1, wherein the first nucleic acid polymerase is selected from the group consisting of Taq DNA polymerase, Tfl DNA polymerase, Tfi DNA polymerase, and Pfu DNA polymerase.

5. The method of claim 1, wherein the at least two hot start mechanisms are different.

6. The method of claim 5, wherein the at least two different hot start mechanisms are selected from the group consisting of antibodies or combinations of antibodies that block DNA polymerase activity at lower temperatures, oligonucleotides that block DNA polymerase activity at lower temperatures, reversible chemical modifications of the DNA polymerase that dissociate at elevated temperatures, amino acid modifications of the DNA polymerase that provide reduced activity at lower temperatures, fusion proteins that include hyperstable DNA binding domains and topoisomerase, temperature dependent ligands that inhibit the DNA polymerase, single stranded binding proteins that sequester primers at lower temperatures, modified primers, or modified dNTPs.

7. The method of claim 1, wherein the reaction composition further comprises a nucleic acid binding dye.

8. The method of claim 1, wherein the reaction composition further comprises a reporter probe.

9. The method of claim 4, wherein the reaction composition further comprises a reverse transcriptase.

10. The method of claim 1, wherein the at least two different hot start mechanisms inhibit activity of the first nucleic acid polymerase by binding to the first nucleic acid polymerase.

11. The method of claim 9, wherein binding to the first nucleic acid polymerase is reversible.

12. The method of claim 1, wherein binding to the first nucleic acid polymerase is temperature-dependent.

13. The method of claim 11, wherein the at least two different hot start mechanisms bind to the first nucleic acid polymerase at a temperature less than about 40° C. and do not bind to the first nucleic acid polymerase at a temperature greater than about 40° C.

14. The method of claim 1, wherein the method further comprises a step for detecting the amplified target nucleic acid.

* * * * *